United States Patent [19]
Cho et al.

[11] Patent Number: 5,719,155
[45] Date of Patent: Feb. 17, 1998

[54] CHROMAN DERIVATIVE AND PHARMACEUTICAL USE THEREOF

[75] Inventors: Hidetsura Cho; Shinsuke Sayama; Susumu Katoh; Kazuo Aisaka; Itsuo Uchida, all of Takatsuki, Japan

[73] Assignee: Japan Tobacco Inc., Tokyo, Japan

[21] Appl. No.: 495,424

[22] PCT Filed: Nov. 10, 1994

[86] PCT No.: PCT/JP94/01901

§ 371 Date: Jul. 10, 1995

§ 102(e) Date: Jul. 10, 1995

[87] PCT Pub. No.: WO95/13272

PCT Pub. Date: May 18, 1995

[30] Foreign Application Priority Data

| Nov. 10, 1993 | [JP] | Japan | 5-281397 |
| Dec. 27, 1993 | [JP] | Japan | 5-354386 |
| Sep. 7, 1994 | [JP] | Japan | 6-240654 |

[51] Int. Cl.⁶ ............................ C07D 311/22; A61K 31/35
[52] U.S. Cl. .............. 514/253; 514/230.5; 514/247; 514/248; 514/259; 514/269; 514/309; 514/337; 514/383; 514/397; 514/406; 514/414; 514/459; 514/460; 544/105; 544/236; 544/237; 544/238; 544/239; 544/285; 544/319; 546/141; 546/283.1
[58] Field of Search .................... 549/401; 544/238; 514/253

[56] References Cited

U.S. PATENT DOCUMENTS

| 4,782,083 | 11/1988 | Cassidy et al. | 514/255 |
| 4,971,982 | 11/1990 | Attwood et al. | 514/337 |
| 5,013,853 | 5/1991 | Gericke | 549/401 |
| 5,071,871 | 12/1991 | Blarer et al. | 549/401 |
| 5,112,839 | 5/1992 | Gericke et al. | 514/337 |
| 5,112,972 | 5/1992 | Gericke et al. | 544/238 |
| 5,130,322 | 7/1992 | Gericke et al. | 514/330 |
| 5,143,924 | 9/1992 | Gericke et al. | 549/401 |
| 5,238,937 | 8/1993 | Gericke et al. | 514/253 |
| 5,318,969 | 6/1994 | Yamanaka | 514/247 |
| 5,387,587 | 2/1995 | Hausler et al. | 214/253 |
| 5,500,425 | 3/1996 | Larsson | 514/233.5 |
| 5,519,023 | 5/1996 | Payard | 514/253 |

FOREIGN PATENT DOCUMENTS

| 0 632 033 | 1/1995 | European Pat. Off. . |
| 3-66681 | 3/1991 | Japan . |
| 4-300880 | 10/1992 | Japan . |
| 5-294954 | 11/1993 | Japan . |

*Primary Examiner*—Donald G. Daus
*Attorney, Agent, or Firm*—Wenderoth, Lind & Ponack

[57] ABSTRACT

Chroman derivatives of the formula [I]

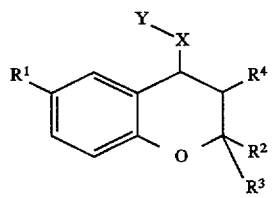

wherein $R^1$ is a cyano, a nitro, a trihalomethyl, a trihalomethoxy or a halogen atom; $R^2$ is a lower alkoxyalkyl, an aryloxyalkyl or a dialkoxyalkyl; $R^3$ is a lower alkoxyalkyl or an aryloxyalkyl; $R^4$ is a hydroxy, a formyloxy or a lower alkanoyloxy; X is N—H, an N—optionally substituted lower alkyl, an oxygen atom, a sulfur atom or a single bond; and Y is an optionally substituted aromatic ring residue or an optionally substituted heterocyclic residue, pharmaceutically acceptable salts thereof and pharmaceutical use thereof. The compound of the present invention and pharmaceutically acceptable salts thereof have selective and excellent coronary vasodilating action and extremely weak hypotensive action. Accordingly, it is possible to selectively increase the coronary blood flow without causing a sudden hypotention causative of tachycardia which has a detrimental effect on the heart, and they are useful as a coronary vasodilator, in particular, an agent for the prophylaxis and treatment of cardiovascular disorders such as angina pectoris and heart failure.

9 Claims, 2 Drawing Sheets

CHROMAN DERIVATIVE AND PHARMACEUTICAL USE THEREOF

TECHNICAL FIELD

The present invention relates to a chroman derivative and pharmaceutical use thereof. More particularly, the present invention relates to a chroman derivative having a selective and superior vasodilating action on the coronary artery and useful as an agent for the prophylaxis and treatment of cardiovascular disorders such as angina pectoris and heart failure.

BACKGROUND ART

A potassium channel is concerned with a resting membrane potential. Activation of the potassium channel leads to a resting membrane potential having moved toward the negative side (hyperpolarization), approaching the equilibrium potential of the potassium ion. In addition, activation of the potassium channel leads to the inhibition of the activation of a potential-dependent calcium channel to result in suppression of an influx of calcium, as well as promotion of an extracellular flow of the intracellular calcium which is due to a sodium-calcium exchange reaction. The hyperpolarization of the membrane and lowered concentration of the intracellular free calcium which occurs thereafter result in relaxation of smooth muscle, and then dilation of blood vessels, to ultimately achieve hypotensive action and coronary vasodilating action. A potassium channel is widely distributed in other smooth muscles (e.g. trachea, intestine and uterus) and is known to also relax these muscles. Accordingly, a compound having a potassium channel activating action is useful as an agent for the treatment or prophylaxis of hypertension, angina pectoris, heart failure, incontinence of urine, asthma and the like.

There have been already reported some compounds which activate the potassium channel. For example, Japanese Patent Unexamined Publication Nos. 300182/1990 (corresponding to U.S. Pat. No. 5,104,890) and 279377/1991 (corresponding to U.S. Pat. No. 5,095,016) disclose chroman derivatives wherein the 4-position amidino of benzopyran is modified by lower alkyl or phenyl, such as 6-cyano-3,4-dihydro-2,2-dimethyl-trans-4-[(N-cyano-acetimidoyl)amino]-2H-benzo[b]pyran-3-ol and 6-cyano-3,4-dihydro-2,2-dimethyl-trans-4-[(N-cyano-benzimidoyl)amino]-2H-benzo[b]pyran-3-ol; Japanese Patent Unexamined Publication Nos. 178850/1993 (corresponding to U.S. Pat. No. 5,300,511) and 194496/1993 disclose chroman derivatives wherein one of the 2-position methyls of benzopyran is modified by dimethoxy, such as 2-dimethoxymethyl-2-methyl-4-(3'-N-oxopyridyl)-6-cyano-2H-1-benzopyran. Japanese Patent Unexamined Publication No. 294954/1993 (EPO 632 033 A1) (corresponding to EPO 632 033 A1) happens to disclose a chroman derivative having, as one of the 2-position substituents, 2,2-bismethoxymethyl, such as 3-hydroxy-2,2-bismethoxymethyl-N-methyl-6-nitro-2H-1-benzopyran-4-carbothioamide. The invention of said publication is, as is clear from the description therein, mainly characterized by the 4-position substituent of the benzopyran ring and is not the compound of the present invention. Naturally, the publication merely recites conventionally known, ordinary pharmacological actions of potassium channel activating compounds, such as those useful for an anti-asthma agent, a hypotensive agent, an anti-angina pectoris agent and a therapeutic agent for incontinence of urine, and does not include a description indicating that such specific compound has a selective coronary vasodilating action or even a suggestive remark to this effect. Moreover, Japanese Patent Unexamined Publication No. 300880/1992 discloses a chroman derivative having, as a 4-position substituent of benzopyran, an amino group substituted by heterocyclic residue, such as 2,2-dimethyl-4-(1-methyl-1,6-dihydro-6-oxo-3-pyridazinylamino)-6-cyano-3-chromanol. However, the publication does not disclose substitution of the 2-position of benzopyran with 2,2-bismethoxymethyl. Japanese Patent Unexamined Publication No. 66681/1991 discloses, as one of the exemplified compounds, a chroman derivative such as 2-methoxymethyl-2-methyl-4-(1,2-dihydro-2-oxo-1-pyridyl)-6-cyano-3-chromanol wherein one of the 2-position methyls of benzopyran is modified by methoxy, and also exemplifies 1-methyl-1,6-dihydro-6-oxo-3-pyridazinyl-oxy as a 4-position substituent. However, there is no suggestion to modify the 2-position group of benzopyran with 2,2-bismethoxymethyl. Japanese Patent Unexamined Publication Nos. 300880/1992 and 66681/1991 teach that such compounds decrease resistance to blood flow in coronary artery while retaining the influence on the heart rate small, thereby to increase coronary blood flow. These known compounds do not necessarily show sufficient remediable effects against coronary vascular diseases such as heart failure, and a superior drug has been demanded.

DISCLOSURE OF THE INVENTION

The present inventors have conducted intensive studies with the aim of finding a compound having high selectivity and safer and superior coronary vasodilating action, and found that substitution of one of the 2-position groups of benzopyran with lower alkoxyalkyl, aryloxyalkyl or dialkoxyalkyl, and the other with lower alkoxyalkyl or aryloxyalkyl, specifically a substitution of the 2-position groups of benzopyran with two lower alkoxyalkyl groups, in particular, 2,2-bismethoxymethyl, surprisingly results in a chroman derivative and a pharmaceutically acceptable salt thereof, which are effective for the prophylaxis and treatment of the aforementioned cardiovascular diseases such as angina pectoris and heart failure, and which do not cause severe hypotention causative of tachycardia; namely, a chroman derivative and a pharmaceutically acceptable salt thereof having a surprising selectivity and an excellent coronary vasodilating action beyond expectation, which are pharmaceutically highly safe and cause minimum side-effects, which resulted in the completion of the present invention.

That is, the chroman derivative of the present invention and a coronary vasodilating agent containing same as a main ingredient are as follows.

(1) Chroman derivatives of the formula [I]

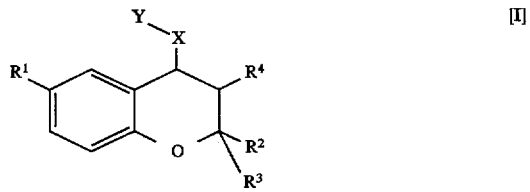

wherein $R^1$ is a cyano, a nitro, a trihalomethyl, a trihalomethoxy or a halogen atom;

$R^2$ is a lower alkoxyalkyl, an aryloxyalkyl or a dialkoxyalkyl;

R³ is a lower alkoxyalkyl or an aryloxyalkyl;

R⁴ is a hydroxy, a formyloxy or a lower alkanoyloxy;

X is N—H, an N-optionally substituted lower alkyl, an oxygen atom, a sulfur atom or a single bond; and Y is an optionally substituted aromatic ring residue or an optionally substituted heterocyclic residue, and pharmaceutically acceptable salts thereof.

(2) Chroman derivatives of the above (1) wherein R¹ is a cyano, a nitro or a halogen atom, R² is a lower alkoxyalkyl, R³ is a lower alkoxyalkyl, R⁴ is a hydroxy and X is N—H or an oxygen atom, and pharmaceutically acceptable salts thereof.

(3) Chroman derivatives of the above (2) wherein X is N—H, and pharmaceutically acceptable salts thereof.

(4) Chroman derivatives of the above (3) wherein R¹ is a cyano, and pharmaceutically acceptable salts thereof.

(5) Chroman derivatives of any one of the above (2) to (4), wherein R² is a methoxymethyl and R³ is a methoxymethyl, and pharmaceutically acceptable salts thereof.

(6) Chroman derivatives of the above (1), wherein the aromatic ring residue at Y is a phenyl or the heterocyclic residue at Y is indolyl, pyrazolyl, imidazolyl, triazolyl, quinazolinyl, dihydrooxoquinazolinyl, isoquinolinyl, dihydrooxoisoquinolyl, pyrimidinyl, dihydrooxopyrimidinyl, pyridazinyl, dihydrooxopyridazinyl, dihydrothioxopyridazinyl, pyridyl, dihydrooxopyridyl, phthalazinyl, dihydrooxophthalazinyl, pyridazinooxazinyl, tetrahydrooxo-2H-pyridazino[4,5-b]-1,4-oxazinyl, pyrazino[2,3-d]pyridazinyl, hexahydrooxopyrazino[2,3-d]pyridazinyl or pyridine-N-oxide, and pharmaceutically acceptable salts thereof.

(7) Chroman derivatives of the above (6) wherein R¹ is a cyano, a nitro or a halogen atom, R² is a lower alkoxyalkyl, R³ is a lower alkoxyalkyl, R⁴ is a hydroxy and X is N—H or an oxygen atom, and pharmaceutically acceptable salts thereof.

(8) Chroman derivatives of the above (7) wherein X is N—H, and pharmaceutically acceptable salts thereof.

(9) Chroman derivatives of the above (8) wherein R¹ is a cyano, and pharmaceutically acceptable salts thereof.

(10) Chroman derivatives of any one of the above (7) to (9), wherein R² is a methoxymethyl and R³ is a methoxymethyl, and pharmaceutically acceptable salts thereof.

(11) Chroman derivatives of the above (10) wherein X is N—H and Y is 1,6-dihydro-1-lower alkyl-6-oxo-3-pyridazinyl or 1,6-dihydro-1-substituted alkyl-6-oxo-3-pyridazinyl, and pharmaceutically acceptable salts thereof.

(12) Chroman derivatives of the above (1) which is selected from the group consisting of (−)-(3S,4R)-6-cyano-3,4-dihydro-4-[(1,6-dihydro-1-methyl-6-oxo-3-pyridazinyl)amino]-2,2-bis(methoxymethyl)-2H-1-benzopyran-3-ol, (−)-(3S,4R)-6-cyano-3,4-dihydro-4-[(1,6-dihydro-1-methyl-6-oxo-3-pyridazinyl)oxy]-2,2-bis(methoxymethyl)-2H-1-benzopyran-3-ol, (−)-(3S,4R)-6-cyano-3,4-dihydro-2,2-bis(methoxymethyl)-4-[3,4-dihydro-4-oxoquinazolin-2-ylthio]-2H-1-benzopyran-3-ol, (−)-(3S,4R)-6-cyano-4-(3-cyano-1H-indol-1-yl)-3,4-dihydro-2,2-bis(methoxymethyl)-2H-1-benzopyran-3-ol, (−)-(3S,4R)-4-[(6-chloro-3-pyridazinyl)amino]-6-cyano-3,4-dihydro-2,2-bis(methoxymethyl)-2H-1-benzopyran-3-ol, (+)-(3S,4R)-6-cyano-4-(3-formyl-1H-indol-1-yl)-3,4-dihydro-2,2-bis(methoxymethyl)-2H-1-benzopyran-3-ol, (−)-(3S,4R)-4-[(6-acetyloxy-3-pyridazinyl)amino]-6-cyano-3,4-dihydro-2,2-bis(methoxymethyl)-2H-1-benzopyran-3-ol, (−)-(3S,4R)-6-cyano-3,4-dihydro-4-[(1,6-dihydro-6-oxo-3-pyridazinyl)amino]-2,2-bis(methoxymethyl)-2H-1-benzopyran-3-ol, (−)-(3S,4R)-6-cyano-3,4-dihydro-2,2-bis(methoxymethyl)-4-[3-(trans-β-nitro)vinyl-1H-indol-1-yl]-2H-1-benzopyran-3-ol, (−)-(Z)-1-[(3S,4R)-6-cyano-3,4-dihydro-2,2-bis(methoxymethyl)-3-hydroxy-2H-1-benzopyran-4-yl]-1H-indole-3-carboxyaldehydoxime, (−)-(E)-1-[(3S,4R)-6-cyano-3,4-dihydro-2,2-bis(methoxymethyl)-3-hydroxy-2H-1-benzopyran-4-yl]-1H-indole-3-carboxyaldehydoxime, (−)-(3S,4R)-6-cyano-3,4-dihydro-4-(4-methoxycarbonyl-1H-pyrazol-1-yl)-2,2-bis(methoxymethyl)-2H-1-benzopyran-3-ol, (−)-(3S,4R)-6-cyano-4-[(1-ethyl-1,6-dihydro-6-oxo-3-pyridazinyl)amino]-3,4-dihydro-2,2-bis(methoxymethyl)-2H-1-benzopyran-3-ol, (−)-(3S,4R)-6-cyano-3,4-dihydro-4-[(1,6-dihydro-1-isopropyl-6-oxo-3-pyridazinyl)amino]-2,2-bis(methoxymethyl)-2H-1-benzopyran-3-ol, (−)-(3S,4R)-6-cyano-4-(5-cyano-1H-indol-1-yl)-3,4-dihydro-2,2-bis(methoxymethyl)-2H-1-benzopyran-3-ol, (+)-(3S,4R)-6-cyano-3,4-dihydro-4-(3,4-dihydro-4-oxopyrimidin-3-yl)-2,2-bis(methoxymethyl)-2H-1-benzopyran-3-ol, (−)-(3S,4R)-6-cyano-3,4-dihydro-2,2-bis(methoxymethyl)-4-phenoxy-2H-1-benzopyran-3-ol, (±)-trans-6-cyano-3,4-dihydro-4-[(1,6-dihydro-1-methyl-6-oxo-3-pyridazinyl)amino]-2,2-bis(methoxymethyl)-2H-1-benzopyran-3-ol, (+)-(3S,4R)-6-cyano-4-[(2-cyanophenyl)amino]-3,4-dihydro-2,2-bis(methoxymethyl)-2H-1-benzopyran-3-ol, (−)-(3S,4R)-6-cyano-4-[(4-cyanophenyl)amino]-3,4-dihydro-2,2-bis(methoxymethyl)-2H-1-benzopyran-3-ol, (−)-(3S,4R)-6-cyano-3,4-dihydro-2,2-bis(methoxymethyl)-4-[(pyrimidin-2-yl)amino]-2H-1-benzopyran-3-ol, (+)-(3S,4R)-6-cyano-3,4-dihydro-4-(1,4-dihydro-4-oxopyridin-1-yl)-2,2-bis(methoxymethyl)-2H-1-benzopyran-3-ol, (−)-(3S,4R)-4-(4-amino-1,2-dihydro-2-oxopyrimidin-1-yl)-6-cyano-3,4-dihydro-2,2-bis(methoxymethyl)-2H-1-benzopyran-3-ol, (−)-(3S,4R)-6-cyano-3,4-dihydro-2,2-bis(methoxymethyl)-4-(4-nitrophenoxy)-2H-1-benzopyran-3-ol, (+)-(3S,4R)-6-cyano-3,4-dihydro-2,2-bis(methoxymethyl)-4-(1H-1,2,4-triazol-3-ylthio)-2H-1-benzopyran-3-ol, (+)-(3S,4R)-6-cyano-3,4-dihydro-2,2-bis(methoxymethyl)-4-(1-methyl-1H-imidazol-2-ylthio)-2H-1-benzopyran-3-ol, (+)-(3S,4R)-4-(3-amino-4H-1,2,4-triazol-4-yl)-6-cyano-3,4-dihydro-2,2-bis(methoxymethyl)-2H-1-benzopyran-3-ol, (−)-(3S,4R)-6-cyano-3,4-dihydro-4-[(1,6-dihydro-1-methyl-6-oxo-3-pyridazinyl)amino]-2,2-bis(methoxymethyl)-2H-1-benzopyran-3-ol hydrate, (+)-(3R,4S)-6-cyano-3,4-dihydro-4-[(1,6-dihydro-1-methyl-6-oxo-3-pyridazinyl)amino]-2,2-bis(methoxymethyl)-2H-1-benzopyran-3-ol, trans-6-fluoro-3,4-dihydro-4-[(1,6-dihydro-1-methyl-6-oxo-3-pyridazinyl)amino]-2,2-bis(methoxymethyl)-2H-1-benzopyran-3-ol, (−)-(3S,4R)-6-bromo-3,4-dihydro-4-[(1,6-dihydro-1-methyl-6-oxo-3-pyridazinyl)amino]-2,2-bis(methoxymethyl)-2H-1-benzopyran-3-ol, trans-4-[(6-chloro-3-pyridazinyl)amino]-3,4-dihydro-2,2-bis(methoxymethyl)-6-nitro-2H-1-benzopyran-3-ol, (−)-(3S,4R)-4-(3-amino-1,6-dihydro-6-oxo-pyridazin-1-yl)-6-cyano-3,4-dihydro-2,2-bis(methoxymethyl)-2H-1-benzopyran-3-ol, (−)-(3S,4R)-6-cyano-3,4-dihydro-4-[(3,4,7,8-tetrahydro-4,7-dimethyl-8-oxo-2H-pyridazino[4,5-b]-1,4-oxazin-5-yl)amino]-2,2-bis(methoxymethyl)-2H-1-benzopyran-3-ol, (−)-(3S,4R)-6-cyano-3,4-dihydro-4-[(3,4,5,6-tetrahydro-4,6-dimethyl-5-oxo-2H-pyridazino[4,5-b]-1,4-oxazin-8-yl)amino]-2,2-bis(methoxymethyl)-2H-1-benzopyran-3-ol, (−)-(3S,4R)-6-cyano-3,4-dihydro-4-[(1,2,3,4,5,6-hexahydro-1,4,6-trimethyl-5-oxopyrazino[2,3-d]-pyridazin-8-yl)amino]-2,2-bis(methoxymethyl)-2H-1-benzopyran-3-ol, (−)-(3S,4R)-6-cyano-3,4-dihydro-4-[(3,4-dihydro-3-methyl-4-oxophthalazin-1-yl)]amino-2,2-bis(methoxymethyl)-2H-1-benzopyran-3-ol, (−)-(3S,4R)-6-cyano-3,4-dihydro-4-[(1,6-dihydro-1-methyl-6-thioxo-3-pyridazinyl)amino]-2,2-bis(methoxymethyl)-2H-1-benzopyran-3-ol, (+)-(3S,4R)-3,4-dihydro-4-[(1,6-dihydro-1-methyl-6-oxo-3-pyridazinyl)amino]-2,2-bis(methoxymethyl)-6-nitro-2H-1-benzopyran-3-ol, trans-4-[(6-chloro-3-pyridazinyl)amino]-6-fluoro-3,4-dihydro-2,2-bis(methoxymethyl)-2H-1-benzopyran-3-ol, trans-6-fluoro-3,4-dihydro-4-[(3,4-dihydro-3-methyl-4-oxophthalazin-1-yl)amino]-2,2-bis(methoxymethyl)-2H-1-benzopyran-3-ol, (−)-(3S,4R)-6-cyano-3,4-dihydro-2,2-bis(methoxymethyl)-4-(2-pyridylamino)-2H-1-benzopyran-3-ol, (−)-(3S,4R)-6-cyano-3,4-dihydro-2,2-bis(methoxymethyl)-4-(3-pyridylamino)-2H-1-benzopyran-3-ol, (−)-(3S,4R)-6-cyano-3,4-dihydro-2,2-bis(methoxymethyl)-4-(4-pyridylamino)-2H-1-benzopyran-3-ol, trans-6-fluoro-3,4-dihydro-4-[(1,6-dihydro-6-oxo-3-pyridazinyl)amino]-2,2-bis(methoxymethyl)-2H-1-benzopyran-3-ol, (3S,4R)-6-cyano-3,4-dihydro-4-[(1,6-dihydro-1-methyl-6-oxo-3-pyridyl)amino]-2,2-bis(methoxymethyl)-2H-1-benzopyran-3-ol, (3S,4R)-6-cyano-3,4-dihydro-4-[(1,6-dihydro-6-oxo-3-pyridyl)amino]-2,2-bis(methoxymethyl)-2H-1-benzopyran-3-ol, (−)-(3S,4R)-6-cyano-3,4-dihydro-4-[(1,6-dihydro-6-oxo-1-n-propyl-3-pyridazinyl)amino]-2,2-bis(methoxymethyl)-2H-1-benzopyran-3-ol, (−)-(3S,4R)-6-cyano-4-[(1-cyclopropylmethyl-1,6-dihydro-6-oxo-3-pyridazinyl)amino]-3,4-dihydro-2,2-bis(methoxymethyl)-2H-1-benzopyran-3-ol, (−)-(3S,4R)-6-cyano-3,4-dihydro-4-[(1,6-dihydro-1-(2-methoxyethyl)-6-oxo-3-pyridazinyl)amino]-2,2-bis(methoxymethyl)-2H-1-benzopyran-3-ol, (−)-(3S,4R)-6-cyano-3,4-dihydro-4-[(1,6-dihydro-1-n-heptyl-6-oxo-3-pyridazinyl)amino]-2,2-bis(methoxymethyl)-2H-1-benzopyran-3-ol, (−)-(3S,4R)-4-[(1-allyl-1,6-dihydro-6-oxo-3-pyridazinyl)-amino]-6-cyano-3,4-dihydro-2,2-bis(methoxymethyl)-2H-1-benzopyran-3-ol, (−)-(3S,4R)-6-cyano-3,4-dihydro-4-[(1,6-dihydro-1-(methoxycarbonylmethyl)-6-oxo-3-pyridazinyl)amino]-2,2-bis-(methoxymethyl)-2H-1-benzopyran-3-ol, (−)-(3S,4R)-6-cyano-3,4-dihydro-4-[(1,6-dihydro-1-(4-nitrophenyl)-6-oxo-3-pyridazinyl)amino]-2,2-bis(methoxymethyl)-2H-1-benzopyran-3-ol, (−)-(3S,4R)-6-cyano-3,4-dihydro-4-[(1,6-dihydro-1-(2-nitrophenyl)-6-oxo-3-pyridazinyl)amino]-2,2-bis(methoxymethyl)-2H-1-benzopyran-3-ol, (3S,4R)-4-[(1-(benzyloxycarbonylmethyl)-1,6-dihydro-6-oxo-3-pyridazinyl)amino]-6-cyano-3,4-dihydro-2,2-bis(methoxymethyl)-2H-1-benzopyran-3-ol, (−)-(3S,4R)-6-cyano-3,4-dihydro-4-[(1,6-dihydro-1-(2-methylthioethyl)-6-oxo-3-pyridazinyl)amino]-2,2-bis(methoxymethyl)-2H-1-benzopyran-3-ol, (3S,4R)-6-cyano-3,4-dihydro-4-[(1,6-dihydro-1-(2-dimethylamino)ethyl)-6-oxo-3-pyridazinyl)amino]-2,2-bis(methoxymethyl)-2H-1-benzopyran-3-ol, (−)-(3S,4R)-6-cyano-4-[(1-cyanomethyl-1,6-dihydro-6-oxo-3-pyridazinyl)amino]-3,4-dihydro-2,2-bis(methoxymethyl)-2H-1-benzopyran-3-ol, (−)-(3S,4R)-4-[(1-benzyl-1,6-dihydro-6-oxo-3-pyridazinyl)-amino]-6-cyano-3,4-dihydro-2,2-bis(methoxymethyl)-2H-1-benzopyran-3-ol, (−)-(3S,4R)-4-[(1-(2-(E)-butenyl)-1,6-dihydro-6-oxo-3-pyridazinyl)amino]-6-cyano-3,4-dihydro-2,2-bis(methoxymethyl)- 2H-1-benzopyran-3-ol, (−)-(3S,4R)-6-cyano-4-[(1-(2-fluoroethyl)-1,6-dihydro-6-oxo-3-pyridazinyl)amino]-3,4-dihydro-2,2-bis(methoxymethyl)-2H-1-benzopyran-3-ol, (−)-(3S,4R)-6-cyano-4-[(1-(2,2,2-trifluoroethyl)-1,6-dihydro-6-oxo-3-pyridazinyl)amino]-3,4-dihydro-2,2-bis(methoxymethyl)-2H-1-benzopyran-3-ol, trans-6-fluoro-3,4-dihydro-4-[(1,6-dihydro-6-oxo-1-n-propyl-3-pyridazinyl)amino]-2,2-bis(methoxymethyl)-2H-1-benzopyran-3-ol, trans-4-[(1-(2-(E)-butenyl)-1,6-dihydro-6-oxo-3-pyridazinyl)amino]-6-fluoro-3,4-dihydro-2,2-bis(methoxymethyl)-2H-1-benzopyran-3-ol, trans-4-[(1-allyl-1,6-dihydro-6-oxo-3-pyridazinyl)amino]-6-fluoro-3,4-dihydro-2,2-bis(methoxymethyl)-2H-1-benzopyran-3-ol, (3S,4R)-6-cyano-4-[(1-ethyl-1,6-dihydro-6-oxo-3-pyridyl)-amino]-3,4-dihydro-2,2-bis(methoxymethyl)-2H-1-benzopyran-3-ol, (−)-(3S,4R)-6-cyano-3,4-dihydro-4-[(1,6-dihydro-1-(2-methylsulfonylethyl)-6-oxo-3-pyridazinyl)amino]-2,2-bis-(methoxymethyl)-2H-1-benzopyran-3-ol, (+)-(3S,4R)-6-cyano-3,4-dihydro-4-[(1,6-dihydro-1-(2-methylsulfinylethyl)-6-oxo-3-pyridazinyl)amino]-2,2-bis-(methoxymethyl)-2H-1-benzopyran-3-ol, (−)-(3S,4R)-6-cyano-4-[(1-(2-cyanoethyl)-1,6-dihydro-6-oxo-3-pyridazinyl)amino]-3,4-dihydro-2,2-bis(methoxymethyl)-2H-1-benzopyran-3-ol, (−)-(3S,4R)-6-cyano-3,4-dihydro-4-[(1,6-dihydro-1-(2-methoxycarbonylethyl)-6-oxo-3-pyridazinyl)amino]-2,2-bis-(methoxymethyl)-2H-1-benzopyran-3-ol, trans-4-[(1-(2-cyanoethyl)-1,6-dihydro-6-oxo-3-pyridazinyl)amino]-6-fluoro-3,4-dihydro-2,2-bis (methoxymethyl)-2H-1-benzopyran-3-ol, trans-6-fluoro-3,4-dihydro-4-[(1,6-dihydro-1-(2-methoxycarbonylethyl)-6-oxo-3-pyridazinyl)amino]-2,2-bis(methoxymethyl)-2H-1-benzopyran-3-ol, (3S,4R)-6-cyano-4-[(1-(2-cyanoethyl)-1,6-dihydro-6-oxo-3-pyridyl)amino]-3,4-dihydro-2,2-bis (methoxymethyl)-2H-1-benzopyran-3-ol, (3S,4R)-6-cyano-3,4-dihydro-4-[(1,6-dihydro-1-(2-methoxycarbonylethyl)-6-oxo-3-pyridyl)amino]-2,2-bis(methoxymethyl)-2H-1-benzopyran-3-ol, (−)-(3S,4R)-6-cyano-3,4-dihydro-4-[(1,6-dihydro-6-oxo-1-(2-nitroethyl)-3-pyridazinyl)amino]-2,2-bis (methoxymethyl)-2H-1-benzopyran-3-ol, (−)-(3S,4R)-6-cyano-4-[(1-(4-diethylamino-2-butyn-1-yl)-1,6-dihydro-6-oxo-3-pyridazinyl)amino]-3,4-dihydro-2,2-bis-(methoxymethyl)-2H-1-benzopyran-3-ol, (−)-(3S,4R)-4-[(1-carboxymethyl-1,6-dihydro-6-oxo-3-pyridazinyl)amino]-6-cyano-3,4-dihydro-2,2-bis (methoxymethyl)-2H-1-benzopyran-3-ol, (−)-(3S,4R)-6-cyano-4-[(4-fluorophenyl)amino]-3,4-dihydro-2,2-bis(methoxymethyl)-2H-1-benzopyran-3-ol, (−)-(3S,4R)-6-cyano-4-[(4-fluoro-3-methylphenyl) amino]-3,4-dihydro-2,2-bis(methoxymethyl)-2H-1-benzopyran-3-ol, (+)-2-[(3S,4R)-6-cyano-3,4-dihydro-2,2-bis (methoxymethyl)-3-hydroxy-2H-1-benzopyran-4-ylamino]-pyridine-N-oxide, (+)-3-[(3S,4R)-6-cyano-3,4-dihydro-2,2-bis (methoxymethyl)-3-hydroxy-2H-1-benzopyran-4-ylamino]-pyridine-N-oxide, (−)-(3S,4R)-6-cyano-3,4-dihydro-4-(1,2-dihydro-1-oxo-isoquinolin-2-yl)-2,2-bis(methoxymethyl)-2H-1-benzopyran-3-ol, (+)-(3S,4R)-6-cyano-3,4-dihydro-4-(2,3-dihydro-3-oxoisoquinolin-2-yl)-2,2-bis(methoxymethyl)-2H-1-benzopyran-3-ol, (−)-(3S,4R)-6-cyano-3,4-dihydro-4-[(3,4-dihydro-3-methyl-4-oxophthalazin-1-yl)oxy]-2,2-bis (methoxymethyl)-2H-1-benzopyran-3-ol, (−)-(3S,4R)-6-cyano-3,4-dihydro-4-[(1,6-dihydro-1,4,5-trimethyl-6-oxo-3-pyridazinyl)oxy]-2,2-bis (methoxymethyl)-2H-1-benzopyran-3-ol, (−)-(3S,4R)-6-bromo-3,4-dihydro-4-[(1,6-dihydro-1-methyl-6-oxo-3-pyridazinyl)oxy]-2,2-bis (methoxymethyl)-2H-1-benzopyran-3-ol and (−)-(3S,4R)-3,4-dihydro-4-[(1,6-dihydro-1-methyl-6-oxo-3-pyridazinyl)oxy]-2,2-bis(methoxymethyl)-6-nitro-2H-1-benzopyran-3-ol, and pharmaceutically acceptable salts thereof.

(13) Chroman derivatives of the above (1) which is selected from the group consisting of (−)-(3S,4R)-6-cyano-3,4-dihydro-4-[(1,6-dihydro-1-methyl-6-oxo-3-pyridazinyl)amino]-2,2-bis (methoxymethyl)-2H-1-benzopyran-3-ol, (−)-(3S,4R)-6-cyano-4-[(1-ethyl-1,6-dihydro-6-oxo-3-pyridazinyl)amino]-3,4-dihydro-2,2-bis (methoxymethyl)-2H-1-benzopyran-3-ol, (−)-(3S,4R)-6-cyano-3,4-dihydro-4-[(1,6-dihydro-1-isopropyl-6-oxo-3-pyridazinyl)amino]-2,2-bis (methoxymethyl)-2H-1-benzopyran-3-ol, (−)-(3S,4R)-6-cyano-3,4-dihydro-4-[(1,6-dihydro-1-methyl-6-oxo-3-pyridazinyl)amino]-2,2-bis (methoxymethyl)-2H-1-benzopyran-3-ol hydrate and (−)-(3S,4R)-6-cyano-4-[(1-cyclopropylmethyl-1,6-dihydro-6-oxo-3-pyridazinyl)amino]-3,4-dihydro-2,2-bis(methoxymethyl)-2H-1-benzopyran-3-ol, and pharmaceutically acceptable salts thereof.

(14) Pharmaceutical compositions comprising a chroman derivative of any one of the above (1) to (12) or a pharmaceutically acceptable salt thereof.

(15) Pharmaceutical compositions comprising a chroman derivative of the above (13) or a pharmaceutically acceptable salt thereof.

(16) Pharmaceutical compositions of the above (14) or (15), which is a coronary vasodilator.

Throughout the present specification, the symbols used for various definitions mean the following.

The lower alkyl represented by X is a straight or branched alkyl having 1 to 5, preferably 1 to 4 carbon atoms, which is exemplified by methyl, ethyl, n-propyl, isopropyl, n-butyl, isobutyl, sec-butyl, tert-butyl, n-pentyl, isopentyl and 1,1-dimethylpropyl.

The lower alkoxyalkyl represented by $R^2$ and $R^3$ is an alkoxyalkyl wherein the total carbon number of the alkoxy moiety and alkyl moiety is 2 to 6, preferably 2 to 5 and the alkoxy moiety and the alkyl moiety may be straight or branched. Specific examples include methoxymethyl, 1-methoxyethyl, 2-methoxyethyl, 3-methoxypropyl, 2-methoxypropyl, 1-methoxypropyl, 1-methoxy-1-methylethyl, ethoxymethyl, propoxymethyl, isopropoxymethyl, butoxymethyl, isobutoxymethyl, sec-butoxymethyl, tert-butoxymethyl and pentoxymethyl, with preference given to methoxymethyl, 1-methoxyethyl and 2-methoxyethyl and particular preference given to methoxymethyl. When the occasion demands, $R^2$ and $R^3$ may combinedly form —CH$_2$—O—CH$_2$—O—CH$_2$—.

The dialkoxyalkyl represented by $R^2$ is a dialkoxyalkyl having 3 to 8, preferably 3 to 5 carbon atoms which is a lower alkyl wherein two lower alkoxy groups are bonded, as mentioned above. Examples thereof include dimethoxymethyl, 1,1-dimethoxyethyl, 1,2-dimethoxyethyl, 2,2-dimethoxyethyl, 1,1-dimethoxypropyl, 1,2-dimethoxypropyl, 1,3-dimethoxypropyl, 2,2-dimethoxypropyl, 2,3-dimethoxypropyl, 3,3-dimethoxypropyl, 1,1-dimethoxybutyl, 1,2-dimethoxybutyl, 1,3-dimethoxybutyl, 1,4-dimethoxybutyl, 2,2-dimethoxybutyl, 2,3-dimethoxybutyl, 2,4-dimethoxybutyl, 3,3-dimethoxybutyl, 3,4-dimethoxybutyl, 4,4-dimethoxybutyl, methoxyethoxymethyl, 1-methoxy-1-ethoxyethyl, 1-methoxy-2-ethoxyethyl, 2-methoxy-1-ethoxyethyl, 2-methoxy-2-ethoxyethyl, 1-methoxy-1-ethoxypropyl, 1-methoxyl-2-ethoxypropyl, 1-methoxy-3-ethoxypropyl, 2-methoxy-1-ethoxypropyl, 2-methoxy-2-ethoxypropyl, 2-methoxy-3-ethoxypropyl, 3-methoxy-1-ethoxypropyl, 3-methoxy-2-ethoxypropyl, 3-methoxy-3-ethoxypropyl, 1-methoxymethyl-2-ethoxyethyl, 1-methoxy-1-ethoxybutyl, 1-methoxy-2-ethoxybutyl, 1-methoxy-3-ethoxybutyl, 1-methoxy-4-ethoxybutyl, 2-methoxy-1-ethoxybutyl, 2-methoxy-2-ethoxybutyl, 2-methoxy-3-ethoxybutyl, 2-methoxy-4-ethoxybutyl, 3-methoxy-1-ethoxybutyl, 3-methoxy-2-ethoxybutyl, 3-methoxy-3-ethoxybutyl, 3-methoxy-4-ethoxybutyl, 4-methoxy-1-ethoxybutyl, 4-methoxy-2-ethoxybutyl, 4-methoxy-3-ethoxybutyl, 4-methoxy-4-ethoxybutyl, diethoxymethyl, 1,1-diethoxyethyl, 1,2-diethoxyethyl, 2,2-diethoxyethyl, 1,1-diethoxypropyl, 1,2-diethoxypropyl, 1,3-diethoxypropyl, 2,2-diethoxypropyl, 2,3-diethoxypropyl, 3,3-diethoxypropyl, 1,1-diethoxybutyl, 1,2-diethoxybutyl, 1,3-diethoxybutyl, 1,4-diethoxybutyl, 2,2-diethoxybutyl, 2,3-diethoxybutyl, 2,4-diethoxybutyl, 3,3-diethoxybutyl, 3,4-diethoxybutyl and 4,4-diethoxybutyl, with preference given to dimethoxymethyl, 1,1-dimethoxyethyl, 1,2-dimethoxyethyl and 2,2-diethoxyethyl and particular preference given to dimethoxymethyl.

The lower alkanoyloxy represented by $R^4$ is an alkanoyloxy having 2 to 6, preferably 2 to 4 carbon atoms, which is exemplified by acetyloxy, propionyloxy, butyryloxy, valeryloxy and hexanoyloxy, with preference given to acetyloxy and propionyloxy and particular preference given to acetyloxy.

The halogen atom represented by $R^1$ is fluorine atom, chlorine atom, bromine atom or iodine atom, with preference given to fluorine atom, chlorine atom and bromine atom.

The trihalomethyl represented by $R^1$ is a methyl substituted by three optional halogen atoms as mentioned above, which is exemplified by trifluoromethyl, trichloromethyl and tribromomethyl, with preference given to trifluoromethyl.

The trihalomethoxy represented by $R^1$ is a methoxy substituted by three optional halogen atoms as mentioned above, which is exemplified by trifluoromethoxy, trichloromethoxy and tribromomethoxy, with preference given to trifluoromethoxy.

The aromatic ring residue represented by Y is, for example, phenyl, naphthyl or biphenyl, with preference given to phenyl and naphthyl and particular preference given to phenyl.

The heterocyclic residue is a 5- or 6-membered heterocyclic residue having 1 to 4 hetero atoms selected from nitrogen atom, oxygen atom and sulfur atom, besides carbon atom, as an atom constituting the ring, and may be a condensed ring residue. Examples thereof include indolyl, pyrazolyl, imidazolyl, triazolyl (e.g. 1,2,3-triazolyl and 1,2,4-triazolyl), quinazolinyl, dihydrooxoquinazolinyl (e.g. 3,4-dihydro-4-oxoquinazolinyl and 1,2-dihydro-2-oxoquinazolinyl), isoquinolyl, dihydrooxoisoquinolyl (e.g. 1,2-dihydro-1-oxoisoquinolyl and 2,3-dihydro-3-oxoisoquinolyl), pyrimidinyl, dihydrooxopyrimidinyl (e.g. 1,2-dihydro-2-oxopyrimidinyl and 3,4-dihydro-4-oxopyrimidinyl), pyridazinyl, dihydrooxopyridazinyl (e.g. 1,6-dihydro-6-oxopyridazinyl), dihydrothioxopyridazinyl (e.g. 1,6-dihydro-6-thioxopyridazinyl), pyridyl, dihydrooxopyridyl (e.g. 1,2-dihydro-2-oxopyridyl and 1,4-dihydro-4-oxopyridyl), phthalazinyl, dihydrooxophthalazinyl (e.g. 1,2-dihydro-1-oxophthalazinyl), pyridazinooxazinyl (e.g. 2H-pyridazino[4,5-b]-1,4-oxazinyl), tetrahydrooxo-2H-pyridazino[4,5-b]-1,4-oxazinyl (e.g. 3,4,5,6-hexahydro-5-oxo-2H-pyridazino[4,5-b]-1,4-oxazinyl and 3,4,7,8-tetrahydro-8-oxo-2H-pyridazino[4,5-b]-1,4-oxazinyl), pyrazino[2,3-d]pyridazinyl, hexahydrooxopyrazino[2,3-d]pyridazinyl (e.g. 1,2,3,4,5,6-hexahydro-5-oxopyrazino[2,3-d]-pyridazinyl), pyridine-N-oxide, thienyl, furyl, pyrrolyl, thiazolyl, isothiazolyl, oxazolyl, isooxazolyl, oxadiazolyl, thiadiazolyl, pyrazinyl, triazinyl, indolinyl, isoindolinyl, oxoindolinyl, dioxoisoindolinyl, oxoindazolyl, dithiazolyl, dioxolanyl, dithiolyl, pyrrolidinyl, dithiadiazinyl, thiadiazinyl, morpholinyl, oxazinyl, thiazinyl, piperazinyl, piperidinyl, piperazinone, tetrahydrodioxopyrimidinyl, tetrahydrooxopyridazinyl, dihydrooxopyrazinyl, dihydrooxopyrazolyl, tetrazolyl, tetrazinyl, pyranyl, thiopyranyl, furoisoxazolyl, imidazothiazolyl, thienoisothiazolyl, thienothiazolyl, imidazopyrazolyl, cyclopentapyrazolyl, pyrrolopyrrolyl, cyclopentathienyl, thienothienyl, oxadiazolopyrazinyl, benzofurazanyl, thiadiazolopyrimidinyl, triazolothiazinyl, triazolopyrimidinyl, triazolopyridinyl, benzotriazolyl, oxazolopyrimidinyl, oxazolopyridinyl, benzoxazolyl, thiazolopyridazinyl, thiazolopyrimidinyl, benzoisothiazolyl, benzothiazolyl, pyrazolotriazinyl, pyrazolothiazinyl, imidazopyrazinyl, purinyl, pyrazolopyridazinyl, pyrazolopyrimidinyl, imidazopyridinyl, pyranopyrazolyl, benzimidazolyl, benzoxathiolyl, benzodioxalyl, dithiolopyrimidinyl, benzodithiolyl, indolizinyl, isoindolyl, furopyrimidinyl, furopyridinyl, benzofuranyl, isobenzofuranyl, thienopyrazinyl, thienopyrimidinyl, thienodioxynyl, thienopyridinyl, benzothienyl, cyclopentaoxazinyl, cyclopentafuranyl, benzothiadiazinyl, benzotriazinyl, pyridoxazinyl, benzoxazinyl, pyrimidothiazinyl, benzothiazinyl, pyrimidopyridazinyl, pyrimidopyrimidinyl, pyridopyridazinyl, pyridopyrimidinyl, cinnolinyl, quinoxalinyl, benzoxathiinyl, benzodioxynyl, benzodithiinyl, naphthylidinyl, quinolyl, benzopyranyl and benzothiopyranyl. Preferred are indolyl, pyrazolyl, imidazolyl, triazolyl (e.g. 1,2,4-triazolyl), quinazolinyl, dihydrooxoquinazolinyl (e.g. 3,4-dihydro-4-oxoquinazolinyl), isoquinolyl, dihydrooxoisoquinolyl (e.g. 1,2-dihydro-1-oxoisoquinolyl, 2,3-dihydro-3-oxoisoquinolyl), pyrimidinyl, dihydrooxopyrimidinyl (e.g. 1,2-dihydro-2-oxopyrimidinyl, 3,4-dihydro-4-oxopyrimidinyl), pyridazinyl, dihydrooxopyridazinyl (e.g. 1,6-dihydro-6-oxopyridazinyl), dihydrothioxopyridazinyl (e.g. 1,6-dihydro-6-thioxopyridazinyl), pyridyl, dihydrooxopyridyl (e.g. 1,2-dihydro-2-oxopyridyl, 1,4-dihydro-4-oxopyridyl), phthalazinyl, dihydrooxophthalazinyl (e.g. 1,2-dihydro-1-oxophthalazinyl), pyridazinooxazinyl (e.g. 2H-pyridazino[4,5-b]- 1,4-oxazinyl), tetrahydrooxo-2H-pyridazino[4,5-b]-1,4-oxazinyl (e.g. 3,4,5,6-hexahydro-5-oxo-2H-pyridazino[4,5-b]-1,4-oxazinyl, 3,4,7,8-tetrahydro-8-oxo-2H-pyridazino[4,5-b]-1,4-oxazinyl), pyrazino[2,3-d]pyridazinyl, hexahydrooxopyrazino[2,3-d]-pyridazinyl (e.g. 1,2,3,4,5,6-hexahydro-5-oxopyrazino[2,3-d]-pyridazinyl) and pyridine-N-oxide.

When X is a single bond, Y is preferably a heterocyclic ring having at least one nitrogen atom. It is desirable that the nitrogen atom on the hetero ring be directly bonded to the 4-position of chroman. When X is N—H, an N-optionally substituted lower alkyl, oxygen atom or sulfur atom, Y is preferably of a type wherein the carbon atom on the heterocyclic ring is directly bonded to X. When a selective coronary vasodilation is considered, X is particularly preferably N—H. Y—X— is preferably 1,6-dihydro-6-oxo-3-pyridazinyl-amino or 1,6-dihydro-6-oxo-3-pyridazinyloxy, with particular preference given to 1,6-dihydro-6-oxo-3-pyridazinylamino.

"Optionally substituted" in the definition of X and Y means that the group may be substituted by 1 to 3 substituents which may be the same or different. Specific examples include alkyl such as methyl, ethyl, n-propyl, isopropyl, n-butyl, isobutyl, sec-butyl, tert-butyl, n-pentyl, hexyl, heptyl and octyl [the alkyl may be substituted by nitro, halogen atom (as defined above), cyano, lower alkoxy (as defined later), cycloalkyl (e.g. cyclopropyl, cyclobutyl, cyclopentyl and cyclohexyl), alkylsulfonyl (as defined later), alkylsulfinyl (e.g. methylsulfinyl, ethylsulfinyl, propylsulfinyl and butylsulfinyl), carboxyl, amino, alkylamino (as defined later), dialkylamino (as defined later), alkylthio (as defined later), aralkyloxycarbonyl (e.g. benzyloxycarbonyl, phenethyloxycarbonyl and phenylpropyloxycarbonyl) and alkoxycarbonyl (as defined later)]; lower alkoxy such as methoxy, ethoxy, propoxy, butoxy and tert-butoxy; halogen atom; nitro; cyano; hydroxy; alkenyl or alkynyl having 2 to 4 carbon atoms such as vinyl, propenyl, butenyl, ethynyl, propinyl and butynyl [these may be substituted by dialkylamino (as defined later)]; acyl such as formyl, acetyl, propionyl, butyryl, isobutyryl, benzoyl and naphthoyl; acyloxy such as formyloxy, acetyloxy, propionyloxy, butyryloxy, isobutyryloxy and benzoyloxy; nitroalkenyl such as nitrovinyl, nitropropenyl and nitrobutenyl; aryl such as phenyl, naphthyl and biphenyl [the aryl may be substituted by nitro, cyano or acyl (as defined above)]; aralkyl such as benzyl; aralkyloxy such as benzyloxy, phenetyloxy and phenylpropyloxy; mercapto; alkylthio such as methylthio, ethylthio, propylthio, butylthio, isobutylthio and tert-butylthio; amino; alkylamino such as methylamino, ethylamino, propylamino, diisopropylamino and butylamino; dialkylamino such as dimethylamino, diethylamino, dipropylamino, isopropylamino and dibutylamino; alkoxycarbonyl such as methoxycarbonyl, ethoxycarbonyl, propyloxycarbonyl, isopropyloxycarbonyl, butoxycarbonyl and tert-butoxycarbonyl; hydroxyiminomethyl; alkoxyiminomethyl; amido; phospholyl; sulfonyl; sulfonyloxy; sulfamoyl; alkylphosphoneamide such as methylphosphoneamide, ethylphosphoneamide, propylphosphoneamide and isopropylphosphoneamide; methylenedioxy; alkoxyphospholyl such as methoxyphospholyl, ethoxyphospholyl, propyloxyphospholyl and isopropyloxyphospholyl; alkylsulfonyl such as methylsulfonyl, ethylsulfonyl, propylsulfonyl, isopropylsulfonyl, butylsulfonyl and tert-butylsulfonyl; and alkylsulfonylamino such as methylsulfonylamino, ethylsulfonylamino, propylsulfonylamino, isopropylsulfonylamino, butylsulfonylamino and tert-butylsulfonylamino. Preferred are alkyl such as methyl, ethyl, n-propyl, isopropyl, n-butyl, tert-butyl, n-pentyl, hexyl and heptyl [the alkyl may be substituted by nitro, halogen atom (e.g. fluorine atom and chlorine atom), cyano, lower alkoxy (as defined later), cycloalkyl (e.g. cyclopropyl and cyclohexyl), alkylsulfonyl (e.g. methylsulfonyl and ethylsulfonyl), alkylsulfinyl (e.g. methylsulfinyl and ethylsulfinyl), carboxyl, dialkylamino (e.g. dimethylamino and diethylamino), alkylthio (e.g. methylthio and ethylthio), aralkyloxycarbonyl (e.g. benzyloxycarbonyl) and alkoxycarbonyl (e.g. methoxycarbonyl and ethoxycarbonyl)]; halogen atom; nitro; cyano; hydroxy; alkenyl or alkynyl having 2 to 4 carbon atoms such as vinyl, propenyl, butenyl, ethynyl, propinyl and butynyl [these may be substituted by dialkylamino (e.g. dimethylamino and diethylamino)]; acyl such as formyl, acetyl, propionyl and benzoyl; acyloxy such as formyloxy and acetyloxy; nitroalkenyl such as nitrovinyl, nitropropenyl and nitrobutenyl; aryl such as phenyl [the aryl may be substituted by nitro, cyano and acyl (e.g. formyl and acetyl)]; aralkyl such as benzyl; amino; alkoxycarbonyl such as methoxycarbonyl and butoxycarbonyl; and hydroxyiminomethyl.

The aryloxyalkyl represented by $R^2$ and $R^3$ is a lower alkyl having aryloxy, such as those mentioned above, which is exemplified by phenyloxymethyl, phenyloxyethyl, phenyoxypropyl, phenyloxyisopropyl, phenyloxybutyl, phenyloxypentyl, 1-naphthyloxymethyl, 1-naphthyloxyethyl, 1-naphthyloxypropyl, 1-naphthyloxyisopropyl, 1-naphthyloxybutyl, 1-naphthyloxypentyl, 2-naphthyloxymethyl, 2-naphthyloxyethyl, 2-naphthyloxypropyl, 2-naphthyloxyisopropyl, 2-naphthyloxybutyl, 2-naphthyloxypentyl, o-biphenyloxymethyl, o-biphenyloxyethyl, o-biphenyloxypropyl, o-biphenyloxyisopropyl, o-biphenyloxybutyl, o-biphenyloxypentyl, m-biphenyloxymethyl, m-biphenyloxyethyl, m-biphenyloxypropyl, m-biphenyloxyisopropyl, m-biphenyloxybutyl, m-biphenyloxypentyl, p-biphenyloxymethyl, p-biphenyloxyethyl, p-biphenyloxypropyl, p-biphenyloxyisopropyl, p-biphenyloxybutyl and p-biphenyloxypentyl, with preference given to phenyloxymethyl and 2-phenyloxyethyl.

As mentioned above, $R^1$ means cyano, nitro, trihalomethyl, trihalomethoxy or halogen atom. It is preferably cyano, nitro or halogen atom and particularly preferably cyano. $R^2$ is lower alkoxyalkyl, aryloxyalkyl or dialkoxyalkyl, with preference given to lower alkoxyalkyl and particular preference given to methoxymethyl. $R^3$ is lower alkoxyalkyl or aryloxyalkyl, with preference given to lower alkoxyalkyl and particular preference given to methoxymethyl. $R^4$ is hydroxy, formyloxy or lower alkanoyloxy, with preference given to hydroxy. X is N—H, N—optionally substituted lower alkyl, oxygen atom, sulfur atom or a single bond, with preference given to N—H, oxygen atom, sulfur atom and single bond, more preference given to N—H and oxygen atom, and particular preference given to N—H. Y is an optionally substituted aromatic ring residue or an optionally substituted heterocyclic residue, which is preferably phenyl, indolyl, pyrazolyl, imidazolyl, triazolyl, quinazolinyl, dihydrooxoquinazolinyl, isoquinolyl, dihydrooxoisoquinolyl, pyrimidinyl, dihydrooxopyrimidinyl, pyridazinyl, dihydrooxopyridazinyl, dihydrothioxopyridazinyl, pyridyl, dihydrooxopyridyl, phthalazinyl, dihydrooxophthalazinyl, pyridazinoxazinyl, tetrahydrooxo-2H-pyridazino[4,5-b]-1, 4-oxazinyl, pyrazino[2,3-d]pyridazinyl, hexahydrooxopyrazino[2,3-d]pyridazinyl or pyridine-N-oxide, with preference given to dihydrooxopyridazinyl and more preference given to 1,6-dihydro-1-lower alkyl-6-oxo-3-pyridazinyl and 1,6-dihydro-1-substituted alkyl-6-oxo-3-pyridazinyl.

The pharmaceutically acceptable salts are exemplified by, but not limited to, acid addition salts of various inorganic acids, such as hydrochloride, hydrobromide, sulfate, phosphate and nitrate; acid addition salts of various organic acids, such as acetate, propionate, succinate, glycolate, lactate, malate, tartrate, citrate, maleate, fumarate, methanesulfonate, p-toluenesulfonate and ascorbate; and acids of various amino acids, such as aspartate and glutamate.

The compound of the formula [I] has two or more asymmetric carbons and there exist optically pure diastereomers, racemates thereof and mixtures thereof at optional combinations and ratios, which are all encompassed in the present invention. In the case of racemates, only one optically active compound can be obtained as necessary by optical resolution. By asymmetric synthesis, only one optically active compound can be directly obtained.

The present invention also encompasses hydrates of the compound of the formula [I].

The production methods for the chroman derivatives (hereinafter also referred to as Compound [I]) of the present invention are described in the following. Needless to say that the production method is not limited to those exemplified in the following.

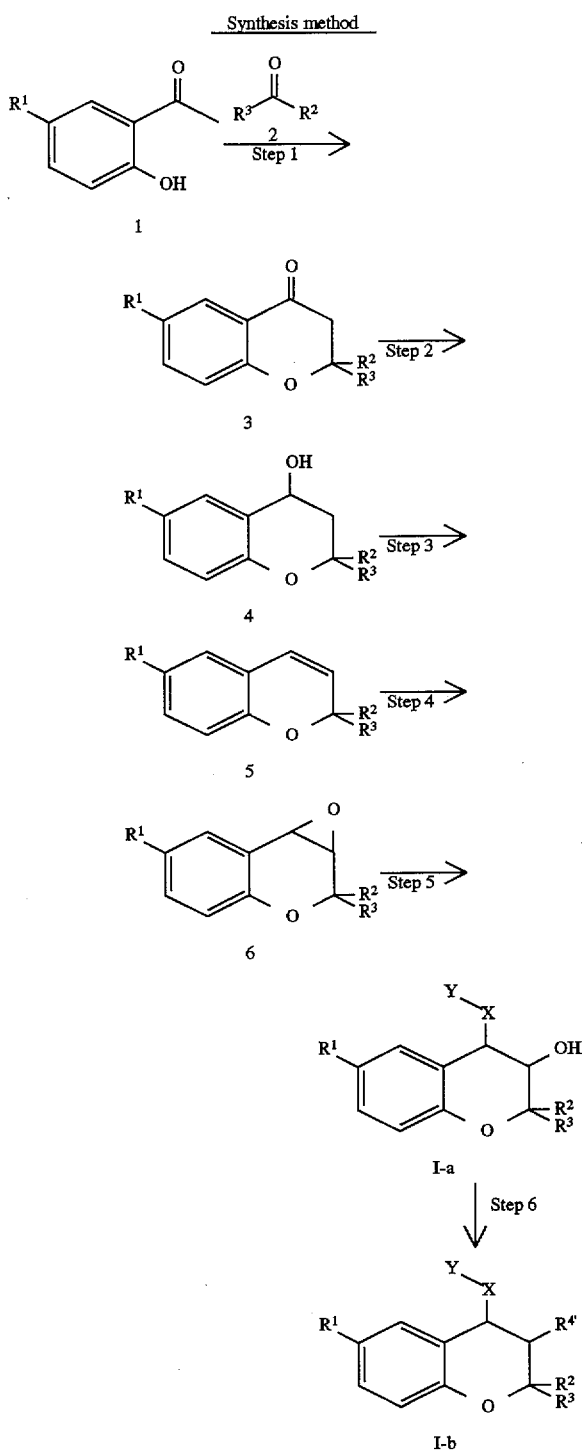

General production method
Step 1

2-Hydroxyacetophenon (compound 1, $R^1$ is as defined above) and compound 2 wherein $R^2$ and $R^3$ are as defined above are refluxed under heating in a solvent such as benzene, chlorobenzene, toluene and xylene, in the presence of a secondary amine such as pyrrolidine, piperidine and morpholine, using a Dean-Stark apparatus, while removing liberated water to give 4-chromanon (compound 3 wherein $R^1$, $R^2$ and $R^3$ are as defined above).

In the present reaction, addition of a small amount of an acid catalyst such as acetic acid, benzoic acid and p-toluenesulfonic acid often leads to preferable results. Alternatively, the compound 3 can be produced by preparing enamine from compound 2 and a secondary amine by a conventional method and reacting the enamine with compound 1. While the compound 1 is mostly a commercially available one, in the contrary case, it can be prepared from p-substituted phenol by acetylation of the ortho-position by Friedel-Crafts reaction or Fries rearrangement.

Step 2

The compound 3 is reduced using a reducing agent such as sodium boron hydride in a solvent such as methanol, ethanol and tetrahydrofuran, preferably in an alcohol solvent such as methanol and ethanol, under cooling to room temperature to give 4-chromanol (compound 4 wherein $R^1$, $R^2$ and $R^3$ are as defined above).

Step 3

The compound 4 is refluxed under heating in a solvent such as benzene, chlorobenzene, toluene and xylene, in the presence of an acid catalyst such as p-toluenesulfonic acid and camphor sulfonic acid, using a Dean-Stark apparatus, while removing liberated water, or the hydroxyl group of compound 4 is activated into acetyl, trifluoroacetyl, methanesulfonyl, trifluoromethanesulfonyl or p-toluenesulfonyl using acetic anhydride, trifluoroacetic acid, methanesulfonyl chloride, trifluoromethanesulfonyl chloride or p-toluenesulfonyl chloride and removing the activated hydroxy using a base such as triethylamine, N-methylmorpholine and diazabicycloundecene, particularly preferably diazabicycloundecene, to give a chromene (compound 5 wherein $R^1$, $R^2$ and $R^3$ are as defined above).

Step 4

The compound 5 is oxidized with an oxidizing agent such as m-chloroperbenzoic acid and peracetic acid in a solvent such as chloroform, methylene chloride and ether, under cooling to room temperature to give 3,4-epoxychroman (compound 6 wherein $R^1$, $R^2$ and $R^3$ are as defined above).

Alternatively, the conversion from compound 5 to compound 6 can be performed in plural steps. That is, compound 5 is converted to bromohydrin compound with N-bromosuccinimide and the like in the mixed solvents of solvents such as methylene chloride, chloroform, ether, dioxane, tetrahydrofuran, acetonitrile, dimethylformamide, dimethyl sulfoxide, methanol and ethanol, and water, and hydrogen bromide is removed from the obtained compound, using a base such as sodium hydroxide to give the compound 6.

Furthermore, the optically active compound 6 can be produced by stereoselectively oxidizing the compound 5 using a Mn(III)-Salen complex as described in J. Am. Chem. Soc., 113, 7063 (1991) and Journal of Synthetic Organic Chemistry, Japan, vol. 51, No. 5, p. 412 (1993).

Step 5

A compound Y—X—H wherein Y and X are as defined above or a derivative thereof, as exemplified by oxodihydropyridazinyl derivative described in J. Med. Chem, 34, 3074 (1991), such as primary or secondary amine compound, alcohol derivative, thioalcohol derivative having various heterocycles, and primary or secondary amine compound, alcohol derivative and thioalcohol derivative having aromatic rings, is reacted with a solution of compound 6 in a polar aprotic solvent (e.g. dimethylformamide and dimethyl sulfoxide), alcohol solvent (e.g. methanol and ethanol) or a mixed solvent thereof, in the presence or absence of a base such as alkali metal hydride (e.g. sodium hydride and potassium hydride), alkaline earth metal hydride (e.g. calcium hydride), alkali metal carbonate (e.g. potassium carbonate and sodium carbonate), metal alcoholate (e.g. potassium tert-butoxide), pyridine, N-methylmorpholine, triethylamine and alkali metal hydroxide (e.g. potassium hydroxide and sodium hydroxide) from room temperature to heating to give a compound I-a (a Compound [I] wherein $R^4$ is hydroxy and $R^1$, $R^2$, $R^3$, X and Y are as defined above).

When a compound wherein Y is 1,6-dihydro-6-oxopyridazinyl is desired, a compound I-a wherein Y is 6-chloropyridazinyl, which is obtained according to the general production method as mentioned above, is reacted in acetic acid as a solvent added with an alcohol solvent such as methanol and ethanol on demand, in the presence of potassium acetate or sodium acetate and, where necessary, in the presence of a base such as potassium hydroxide and sodium hydroxide from room temperature to heating.

When Y is a substituted heterocyclic residue, such as 1,6-dihydro-6-oxopyridazinyl or 1,6-dihydro-6-oxopyridyl substituted by methyl, ethyl, propyl, isopropyl, heptyl, cyclopropylmethyl, allyl, cyanomethyl, cyanoethyl, nitroethyl, methoxycarbonylmethyl, methoxycarbonylethyl, 2-nitrophenyl, 4-nitrophenyl, 2-fluoroethyl, 2,2,2-trifluoroethyl, benzyl, (dimethylamino)ethyl, benzyloxycarbonylmethyl, 2-methylthioethyl, methoxyethyl, 2-butenyl, diethylamino-2-butyn-1-yl, carboxymethyl, methylsulfonylethyl or methylsulfinylethyl, the following method is applied. That is, a compound wherein Y is 1,6-dihydro-6-oxopyridazinyl or 1,6-dihydro-6-oxopyridyl is produced according to the general production method as described above. The compound is reacted with a starting compound corresponding to respective substituents, such as methyl iodide, ethyl iodide, isopropyl bromide, propane bromide, cyclopropylmethyl bromide, heptyl bromide, allyl bromide, bromoacetonitrile, nitroethanol, methyl bromoacetate, methyl acrylate, acrylonitrile, 2-fluoronitrobenzene, 4-fluoronitrobenzene, 1-bromo-2-fluoroethane, 2,2,2-trifluoroethyl iodide, benzyl bromide, 2-dimethylaminoethyl chloride, benzyl bromoacetate, methylthioethyl chloride, methoxyethyl bromide, crotyl bromide and 1,4-dichloro-2-butyn in a polar aprotonic solvent (e.g. dimethylformamide and dimethyl sulfoxide), an alcohol solvent (e.g. methanol and ethanol) or a mixed solvent thereof, in the presence or absence of a base such as alkali metal hydride (e.g. sodium hydride and potassium hydride), alkaline earth metal hydride (e.g. calcium hydride), alkali metal carbonate (e.g. potassium carbonate and sodium carbonate), metal alcoholate (e.g. potassium tert-butoxide), pyridine, N-methylmorpholine, triethylamine and alkali metal hydroxide (e.g. potassium hydroxide and sodium hydroxide) from room temperature to heating to give the desired compound.

When a compound wherein the substituent at the heterocyclic residue is nitroethyl is desired, an alcohol compound such as nitroethanol is reacted with methanesulfonyl chloride or toluenesulfonyl chloride in a solvent such as chloroform and dichloromethane, in the presence of a base such as pyridine and triethylamine to subject the alcohol compound to methanesulfonylation or toluenesulfonylation. The obtained compound is reacted in the presence of a base in the same manner as in the introduction of a substituent to the above-mentioned heterocyclic residue.

In particular, when a compound wherein the substituent at the heterocyclic residue is methylsulfonylethyl or methylsulfinylethyl is desired, for example, 2-methylthioethyl as obtained in the above is oxidized with an oxidizing agent such as m-chloroperbenzoic acid.

When a compound wherein the substituent at the heterocyclic residue is diethylamino-2-butyn-1-yl is desired, for example, a compound wherein Y is 1,6-dihydro-6-oxopyridazinyl is reacted with 1,4-dichloro-2-butyne and then with diethylamine.

When a compound wherein the substituent at the heterocyclic residue is carboxymethyl is desired, for example, the benzyloxycarbonyl obtained in the above reaction is subjected to catalytic reduction by hydrogenation in methanol as a solvent, in the presence of palladium-carbon.

A heteroaryl-N-oxide compound wherein Y is pyridine-N-oxide is obtained by, according to the above-mentioned general production method, producing a compound wherein Y is pyridyl, and oxidizing the compound obtained with an oxidizing agent such as m-chloroperbenzoic acid and peracetic acid, in a solvent such as chloroform, methylene chloride and ether from cooling to heating, particularly preferably from ice-cooling to room temperature.

A heteroarylcarboxyaldehydoxime compound wherein Y is 3-(hydroxyiminomethyl)indolyl is obtained by, according to the above-mentioned general production method, producing a heteroarylcarboxyaldehyde compound wherein Y is 3-formylindolyl, and reacting the said compound in an alcohol solvent such as methanol and ethanol as necessary, in the presence of a base such as pyridine and triethylamine, and hydroxylamine hydrochloride at room temperature to heating.

Step 6

A compound I-b wherein $R^4$ is lower alkanoyloxy or formyloxy and other symbols are as defined above can be produced by converting the 3-position hydroxy of compound I-a to alkanoyl or formyl by a conventional method. Namely, the compound I-a is subjected to alkanoylation by reacting the compound I-a with an acid chloride such as acetic chloride or an acid anhydride such as acetic anhydride, in a solvent such as chloroform and methylene chloride or without solvent, in the presence of a base such as pyridine, lutidine and triethylamine from ice-cooling to room temperature. The compound I-a is subjected to formylation by treating the compound with formic acid or acetic anhydride, under reflux in a solvent which does not inhibit the reaction, such as methylene chloride and chloroform.

The Compound [I] obtained can be isolated and purified by a method conventionally known, such as recrystallization, column chromatography and the like.

The pharmaceutically acceptable salts of Compound [I] can be obtained by treating the Compound [I] with the aforementioned inorganic acid, organic acid or amino acid by a conventional method.

The Compound [I] and pharmaceutically acceptable salts thereof of the present invention have surprising selectivity and excellent coronary vasodilating action beyond expectation and are effective for the prophylaxis and treatment of cardiovascular disorders such as angina pectoris and heart failure. The Compound [I] and pharmaceutically acceptable salts thereof of the present invention exert extremely weak influence on the hypotensive action. Accordingly, coronary blood flow can be increased with surprising selectivity, without causing sudden hypotention causative of tachycardia which has a detrimental effect on the heart. Consequently, they are useful as an agent for the prophylaxis and treatment of cardiovascular disorders such as angina pectoris and heart failure.

In addition, they are expected to show a relaxing action on the smooth muscles other than cardiovascular smooth muscle. Therefore, they are expected to be useful as a therapeutic agent for gastrointestinal tumor, irritable intestinal syndrome and diverticulum disorder, reversible tracheal obliterans and asthma, immature birth, incontinence of urine and cerebrovascular disorders.

It is expected that they are useful for the prevention and treatment of alopecia such as areatic alopecia, when topically applied to the bald scalp.

When the Compound [I] or a pharmaceutically acceptable salt thereof of the present invention is used as a pharmaceutical preparation, it is admixed with a pharmacologically acceptable carrier, excipient, diluent, extender, disintegrator, stabilizer, preservative, buffer, emulsifier, aromatic, coloring agent, sweetener, thickener, flavor, solubilizer and other additives such as water, vegetable oil, alcohol such as ethanol, benzyl alcohol and hydroxypropyl alcohol, carbohydrate such as polyethylene glycol, glycerol triacetate, gelatin, lactose and starch, magnesium stearate, talc, lanolin, petrolatum, lactose, sucrose, glucose, mannit, sorbit, crystalline cellulose, gum arabic, dextrin, pullulan, aluminum silicate, calcium phosphate, waxes, boric acid, DL leucin, fatty acid sodium, magnesium laurylsulfate, dextrin, hydroxypropyl methyl cellulose, polyvinylpyrrolidone, macrogol, carnauba wax, polyoxyethylene, polyoxypropylene, glycol, cacao butter, lauric acid, lecitin, glycerin, sodium p-oxybenzoate, sodium benzoate, salicylic acid and potassium sorbate to give a pharmaceutical composition, which is formed into tablet, pill, powder, granule, suppository, injection, eye drop, liquid, capsule, troche, aerosol, elixir, suspension, emulsion, syrup and the like for oral or parenteral administration.

While the dose varies depending on the kind and severity of diseases, compound to be administered and the administration route, age, sex and body weight of patient and so on, the Compound [I] or a pharmaceutically acceptable salt thereof of the present invention is preferably administered in 0.001–1,000 mg, particularly 0.1–100 mg orally to an adult per day.

Figure 1:
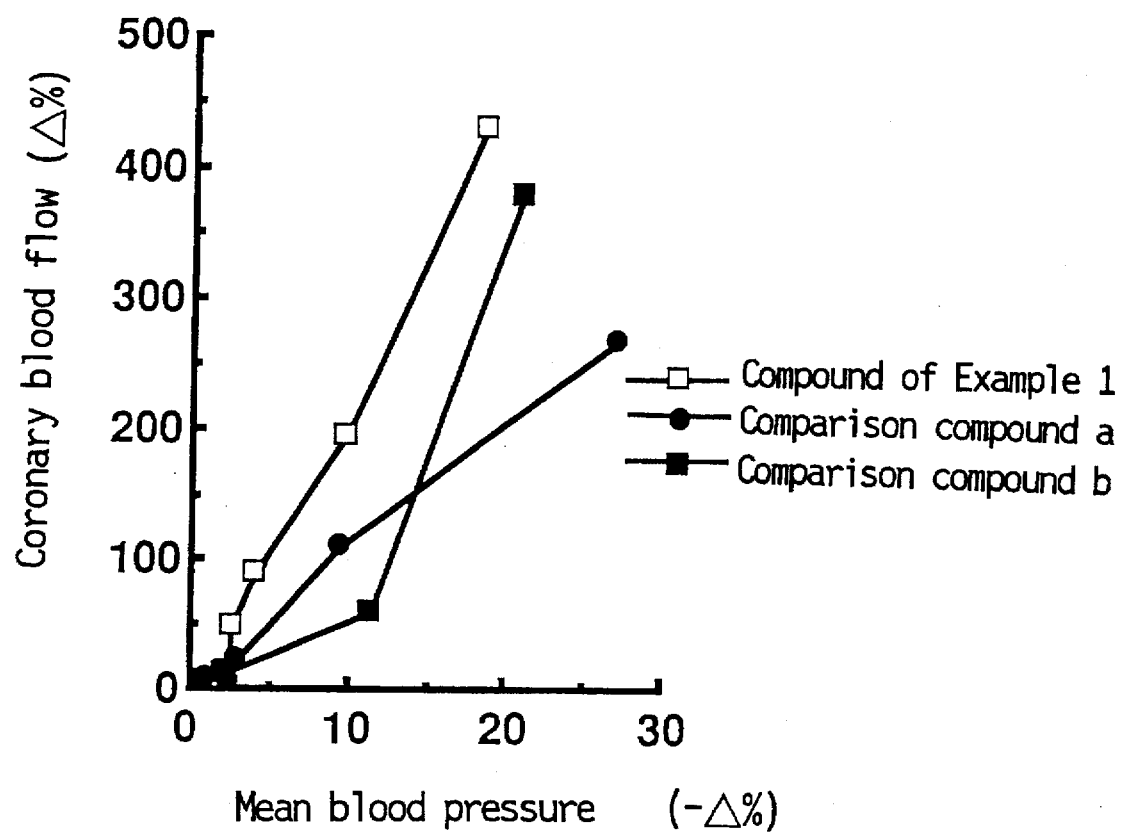
FIG. 1 is a graph showing the relationship among the compound of Example 1, lemakalim [(−)-(3S,4R)-6-cyano-3,4-dihydro-2,2-dimethyl-4-(2-oxopyrrolidin-1-yl)-2H-1-benzopyran-3-ol, reference compound a] and 2-methoxymethyl-2-methyl-4-(1,2-dihydro-2-oxo-1-pyridyl)-6-cyano-3-chromanol (reference compound b) in changes (%) in mean blood pressure (abscissa) and changes (%) in coronary blood flow (ordinate).

The results of the pharmacological evaluation of the compounds of the present invention are shown in the following.

Effect on coronary blood flow

EXPERIMENTAL EXAMPLE 1

Male and female mongrel adult dogs (9.5–15 kg) were anesthetized by intravenous administration of sodium pentobarbital (25 mg/kg). The dogs were fixed on their back and artificially ventilated (20 ml/kg, 18 times/min) with an artificial respirator (SN-408-4, manufactured by Shinano Seisakusho) after tracheal intubation. For continuous anesthesia, a catheter was inserted from the right femoral vein and sodium pentobarbital (3–5 mg/kg/hour) was continuously infused. The blood pressure was measured via a KIFA catheter (17-867-1, manufactured by Siemens Elema, Sweden) inserted from the left femoral artery to abdominal aorta, which was connected to a pressure transducer (TP-400T, manufactured by Nippon Koden). The coronary blood flow changes induced by arterial administration and intravenous administration of compound were tested. The coronary blood flow was measured respectively by an electromagnetic flow probe (FF-030T, manufactured by Nippon Koden) placed in an extracorporeal circulation system from the femoral artery to the coronary artery, when a drug was intraarterially administered, and when a drug was intravenously administered, the coronary blood flow was measured by an electromagnetic flowmeter via electromagnetic flow probes (FJ-020T and FJ-025T, manufactured by Nippon Koden) which were set at the left coronary circumflex after thoracotomy at left fifth costa. These parameters were recorded on a recticorder (RJG-4128, manufactured by Nippon Koden).

The test solution was prepared by dissolving a sample in a mixed solution of N,N-dimethylformamide (30%) and physiological saline (70%) and diluting with physiological saline as appropriate. The test solution was administered into the extracorporeal circulation system or the right femoral vein. The test compounds were the compound of Example 1 to be mentioned later, lemakalim ((−)-(3S,4R)-6-cyano-3,4-dihydro- 2,2-dimethyl-4-(2-oxopyrrolidin-1-yl)-2H-1-benzopyran-3-ol (reference compound a) and 2-methoxymethyl-2-methyl-4-(1,2-dihydro-2-oxo-1-pyridyl)-6-cyano-3-chromanol (low polarity isomer, reference compound b) disclosed in Japanese Patent Unexamined Publication No. 66681/1991).

When the compound of Example 1 of the present invention was administered into the coronary artery, the coronary blood flow increased. Based on the blood flow increase by the coronary arterial administration of nifedipine (1 µg) as 100%, the amount of the compound necessary to achieve 50% increase thereof, namely, $ED_{50}$, was 0.58 µg for the compound of Example 1. At this dose, nifedipine caused marked hypotension, whereas it was not observed in the compound of the present invention. When the compound of Example 1 of the present invention was intravenously administered in a dose of 1–10 µg/kg, the coronary blood flow increased by 15–430%. According to a different test, the compound of Example 1 was superior in duration, in comparison with the reference compound b.

The relationship between the increase in coronary arterial blood flow and decrease in blood pressure induced by intravenous administration of the compounds is shown in FIG. 1. The dose of the intravenous administration was 1, 2, 3, 5 or 10 µg/kg for the compound of Example 1 of the present invention; 0.3, 1, 3 or 10 µg/kg for lemakalim (reference compound a) and 10, 30 or 100 µg/kg for the reference compound b.

As shown in the Figure, the compound of Example 1 of the present invention caused only about 4% hypotension when 100% coronary blood flow increase was intended, whereas the reference compound a caused about 9% hypotention, and the reference compound b caused about 13% hypotension. When 50% coronary blood flow increase was intended, the compound of Example 1 of the present invention caused only about 2.5% hypotension, whereas the reference compound a caused about 5% (more than twice the present invention) and the reference compound b caused about 10% (more than thrice the present invention) hypotension.

EXPERIMENTAL EXAMPLE 2

Male and female beagles (7–14 kg) were anesthetized by intravenous administration of sodium pentobarbital (25 mg/kg). The dogs were fixed on their back and artificially ventilated (20 ml/kg, 18 times/min) with an artificial respirator (SN-408-4, manufactured by Shinano Seisakusho) after tracheal intubation. For continuous anesthesia, a catheter was inserted from the right femoral vein and sodium pentobarbital (5 mg/kg/hour) was persistently injected. The blood pressure was measured via a KIFA catheter (17-867-1, Semens Elema, Sweden) inserted from the femoral artery to the abdominal aorta, which was connected to a pressure transducer (TP-400T, manufactured by Nippon Koden). The coronary blood flow was measured by an electromagnetic flowmeter via electromagnetic flow probes (FJ-020T and FJ-025T, manufactured by Nippon Koden) which were set at the left coronary circumflexus after thoracotomy at the fifth left costa. These parameters were recorded on a stylus recticorder (RJG-4128, manufactured by Nippon Koden).

The test solution was prepared by dissolving a sample in a mixed solution of N,N-dimethylformamide (30%) and physiological saline (70%) and diluting same with physiological saline as appropriate. The test solution was administered into the right femoral vein. The test compounds were the compound of Example 28 to be mentioned later, lemakalim ((−)-(3S,4R)-6-cyano-3,4-dihydro-2,2-dimethyl-4-(2-oxopyrrolidin-1-yl)-2H-1-benzopyran-3-ol), nicorandil and nifedipine (all reference compounds).

When the compound of Example 28 of the present invention was intravenously administered at 0.3–10 μg/kg, the coronary blood flow increased by 6–270%.

Figure 2:
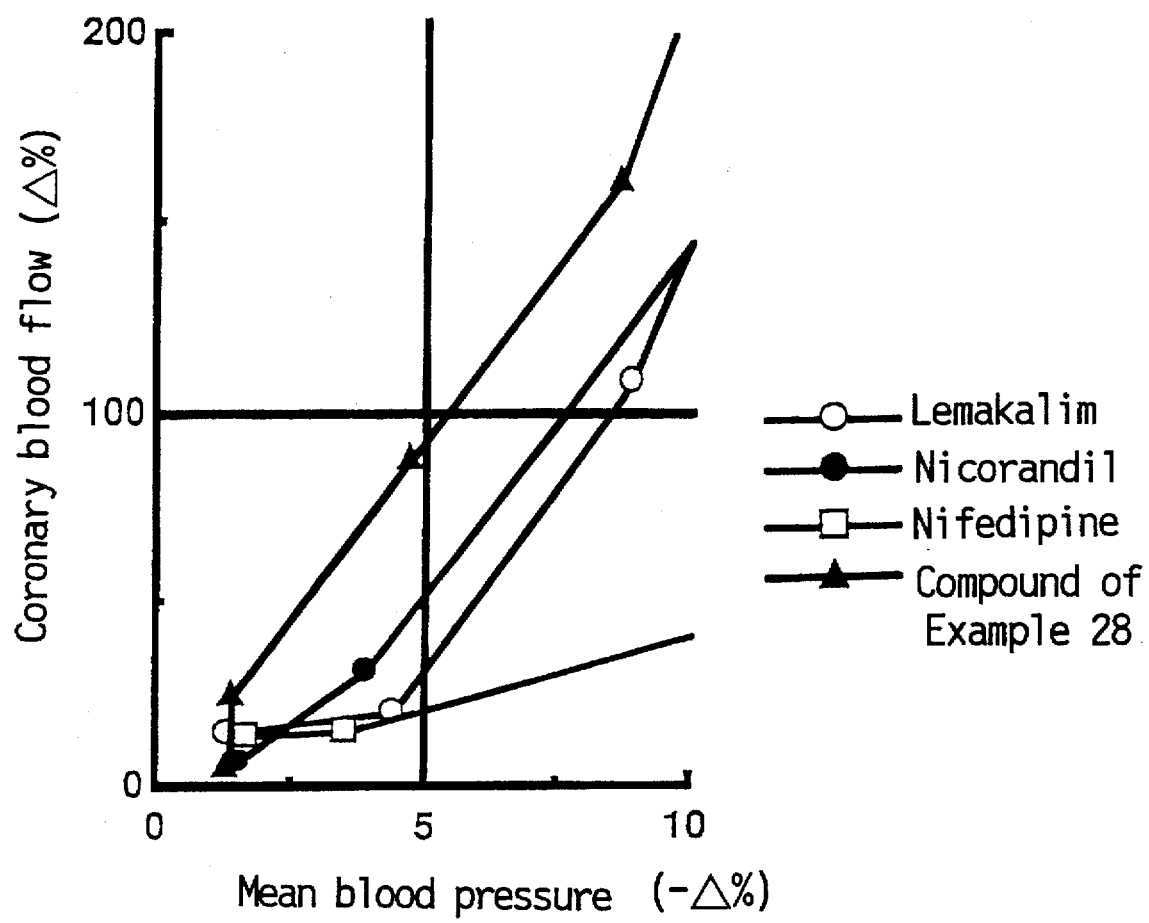
FIG. 2 is a graph showing the relationship among the compound of Example 28, lemakalim ((−)-(3S,4R)-6-cyano-3,4-dihydro-2,2-dimethyl-4-(2-oxopyrrolidin-1-yl)-2H-1-benzopyran-3-ol, nicorandil and nifedipine in changes (%) in mean blood pressure (abscissa) and changes (%) in coronary blood flow (ordinate).

The relationship between the increase in the coronary arterial blood flow and decrease in blood pressure induced by intravenous administration of the compounds is shown in FIG. 2. The doses of the intravenously administered reference compounds were 0.3, 1, 5 or 10 μg/kg for lemakalim, 10, 30, 100 or 300 μg/kg for nicorandil and 0.1, 0.3, 1, 3 or 10 μg/kg for nifedipine.

As shown in the Figure, the compound of Example 28 of the present invention caused only about 6% hypotension when 100% coronary blood flow increase was intended, whereas lemakalim caused about 8.5% hypotension, nicorandil caused 7.5% hypotension and nifedipine caused 23% hypotension. When 50% coronary flow increase was intended, the compound of Example 28 of the present invention caused only about 2.5% hypotension, whereas lemakalim and nicorandil caused about 5% (more than twice the present invention) and nifedipine caused about 12% (more than four times the present invention) hypotension.

The present invention is described in more detail by Preparative Examples and Examples, to which the present invention is not limited.

PREPARATIVE EXAMPLE 1

Production of compound 3 ($R^1$=cyano, $R^2,R^3$=methoxymethyl)

5-Cyano-2-hydroxyacetophenone (13.57 g) was dissolved in toluene (120 ml), and pyrrolidine (6 ml) and 1,3-dimethoxy-2-propanone (15 ml) were added. The mixture was refluxed under heating for 1 hour while removing the generated water. After cooling, the reaction mixture was diluted with ethyl acetate, washed with dilute hydrochloric acid, an aqueous solution of sodium hydrogencarbonate and brine in order, and dried over anhydrous magnesium sulfate. The solvent was distilled away and the residue obtained was purified by silica gel column chromatography (ethyl acetate:hexane=2:8) to give 13.0 g of 6-cyano-3,4-dihydro-2,2-bis(methoxymethyl)-2H-1-benzopyran-4-one.

$^1$H-NMR(CDCl$_3$/ppm) δ2.95(2H, s), 3.35(6H, s), 3.55 (2H, d, J=10.3 Hz), 3.60(2H, d, J=10.3Hz), 7.07(1H, d), 7.68(1H), 8.14(1H).

PREPARATIVE EXAMPLE 2

Production of compound 4 ($R^1$=cyano, $R^2,R^3$=methoxymethyl)

6-Cyano-3,4-dihydro-2,2-bis(methoxymethyl)-2H-1-benzopyran-4-one (12.1 g) obtained in Preparative Example 1 was dissolved in methanol (150 ml), and sodium boron hydride (1.96 g) was portionwise added with stirring under ice-cooling. The mixture was stirred for 1.5 hours and concentrated. Ice and ethyl acetate were added to the residue. The mixture was washed with water, dilute hydrochloric acid, an aqueous solution of sodium hydrogencarbonate and brine in order, and dried over anhydrous magnesium sulfate. The solvent was distilled away to give 11.5 g of 6-cyano-3,4-dihydro-2,2-bis(methoxymethyl)-2H-1-benzopyran-4-ol.

$^1$H-NMR(CDCl$_3$/ppm) δ2.12(1H, dd, J=5.3 Hz, J=14.5 Hz), 2.33(1H, d, J=5.6 Hz, 14.5 Hz), 3.36(3H, s), 3.41(3H, s), 3.4–3.7(4H), 4.77(1H, m), 6.92(1H, d), 7.44(1H, dd), 7.72(1H, d).

PREPARATIVE EXAMPLE 3

Production of compound 5 ($R^1$=cyano, $R^2,R^3$=methoxymethyl)

6-Cyano-3,4-dihydro-2,2-bis(methoxymethyl)-2H-1-benzopyran-4-ol (6.5 g) obtained in Preparative Example 2 was dissolved in toluene (60 ml), and p-toluenesulfonic acid (0.6 g) was added. The mixture was refluxed under heating for 1 hour while removing the generated water. The reaction mixture was concentrated, added with ethyl acetate, washed with water, an aqueous solution of sodium hydrogencarbonate and brine in order, and dried over anhydrous magnesium sulfate. The solvent was distilled away and the residue obtained was purified by silica gel column chromatography (ethyl acetate:hexane=3:17) to give 4.91 g of 6-cyano-2,2-bis(methoxymethyl)-2H-1-benzopyran.

$^1$H-NMR(CDCl$_3$/ppm) δ3.39(6H, s), 3.55(2H, d, J=10.2 Hz), 3.60(2H, d, J=10.2 Hz), 5.76(1H, d, J=10.1 Hz), 6.49(1H, d, J=10.1 Hz), 6.87(1H, d), 7.25(1H, d), 7.39(1H, dd).

PREPARATIVE EXAMPLE 4

Production of compound 6 ($R^1$=cyano, $R^2,R^3$=methoxymethyl)

6-Cyano-2,2-bis(methoxymethyl)-2H-1-benzopyran (4.3 g) obtained in Preparative Example 3 was dissolved in methylene chloride (50 ml), and m-chloroperbenzoic acid (4.75 g) was added under ice-cooling. The mixture was stirred at room temperature. m-Chloroperbenzoic acid was added (2.2 g 1 hour later and 1.5 g 18 hours later) and chloroform was added 21 hours later. The mixture was washed with a 1N aqueous solution of sodium hydroxide, an aqueous solution of sodium hydrogencarbonate and brine. After drying over anhydrous magnesium sulfate, the solvent was distilled away and the residue obtained was purified by silica gel column chromatography (ethyl acetate:hexane= 1:4) to give 4.05 g of 6-cyano-3,4-epoxy-3,4-dihydro-2,2-bis(methoxymethyl)-2H-1-benzopyran.

$^1$H-NMR(CDCl$_3$/ppm) δ3.27(3H, s), 3.48(3H, s), 3.57 (1H, d, J=10.3 Hz), 3.70(1H, d, J=10.3 Hz), 3.71(1H, s), 3.82(1H, d, J=4.4 Hz), 3.94(1H, d, J=4.4 Hz), 6.91(1H, d), 7.53(1H, dd), 7.65(1H, d).

PREPARATIVE EXAMPLE 5

Production of optically active compound of compound 6 ($R^1$=cyano, $R^2,R^3$=methoxymethyl)

6-Cyano-2,2-bis(methoxymethyl)-2H-1-benzopyran (468 mg) obtained in Preparative Example 3 was added to a 0.5M aqueous solution of sodium hypochlorite (8 ml) adjusted to pH 11.5 with a 0.05M phosphate buffer and a 1M aqueous solution of sodium hydroxide, and an Mn(III)-Salen (R,R) complex (25.5 mg) as described in J. Am. Chem. Soc., 113, 7063 (1991) in methylene chloride (2 ml) was added under ice-cooling. The mixture was stirred for 17 hours under ice-cooling, extracted with methylene chloride (3 times), dried, concentrated and subjected to silica gel column chromatography (ethyl acetate:hexane=1:4) to give 398 mg of an optically active compound of the compound of Preparative Example 4, (3R,4R)-6-cyano-3,4-epoxy-3,4-dihydro-2,2-bis(methoxymethyl)-2H-1-benzopyran (89% ee).

In the same manner, 451 mg of 6-cyano-2,2-bis(methoxymethyl)-2H-1-benzopyran was oxidized using an Mn(III)-Salen (S,S) complex as a catalyst to give 370 mg of (3S,4S)-6-cyano-3,4-epoxy-3,4-dihydro-2,2-bis(methoxymethyl)-2H-1-benzopyran (94% ee).

PREPARATIVE EXAMPLE 6

Synthesis of methyl pyrazole-4-carboxylate

4-Pyrazolecarboxylic acid (514 mg) was dissolved in methanol (10 ml) and sulfuric acid (0.25 ml), and the mixture was stirred at room temperature for 2 hours, followed by refluxing under heating for 4 hours. After cooling, a 28% solution (0.95 ml) of sodium methylate in methanol was added to the reaction mixture for neutralization and the solvent was distilled away. Chloroform was added to the residue, and the residue was washed with water and brine and dried over anhydrous magnesium sulfate. The solvent was distilled away to give 433 mg of the title compound.

$^1$H-NMR(CDCl$_3$/ppm) δ3.92(3H, s), 8.08(2H, s), 8.26 (1H, br s)

PREPARATIVE EXAMPLE 7

Production of compound 3 ($R^1$=nitro, $R^2$,$R^3$= methoxymethyl)

By treating 2-hydroxy-5-nitroacetophenone in the same manner as in Preparative Example 1, 3,4-dihydro-2,2-bis(methoxymethyl)-6-nitro-2H-1-benzopyran-4-one was obtained.

$^1$H-NMR(CDCl$_3$/ppm) δ2.97(2H, s), 3.35(6H, s), 3.56 (2H, d), 3.62(2H, d), 7.10(1H, d), 8.31(1H, dd), 8.72(1H, d).

PREPARATIVE EXAMPLE 8

Production of compound 4 ($R^1$=nitro, $R^2$,$R^3$= methoxymethyl)

3,4-Dihydro-2,2-bis(methoxymethyl)-6-nitro-2H-1-benzopyran-4-one obtained in Preparative Example 7 was treated in the same manner as in Preparative Example 2 to give 3,4-dihydro-2,2-bis(methoxymethyl)-6-nitro-2H-1-benzopyran-4-ol.

$^1$H-NMR(CDCl$_3$/ppm) δ2.14(1H, dd, J=5.5 Hz, 14.5 Hz), 2.37(1H, dd, J=5.5 Hz, 14.5 Hz), 3.36(3H, s), 3.40(3H, s), 3.35–3.65(5H, m), 4.80–4.87(1H, m), 6.93(1H, d, J=9.0 Hz), 8.06(1H, dd, J=2.7 Hz, 9.0 Hz), 8.34(1H, d, J=2.7 Hz).

PREPARATIVE EXAMPLE 9

Production of compound 5 ($R^1$=nitro, $R^2$,$R^3$= methoxymethyl)

3,4-Dihydro-2,2-bis(methoxymethyl)-6-nitro-2H-1-benzopyran-4-ol obtained in Preparative Example 8 was treated in the same manner as in Preparative Example 3 to give 2,2-bis(methoxymethyl)-6-nitro-2H-1-benzopyran.

$^1$H-NMR(CDCl$_3$/ppm) δ3.39(6H, s), 3.55–3.63(4H, m), 5.80(1H, d, J=10.1 Hz), 6.55(1H, d, J=10.1 Hz), 6.88(1H, d, J=8.9 Hz), 7.88(1H, d, J=2.7 Hz), 8.02(1H, dd, J=2.7 Hz, 8.9 Hz).

PREPARATIVE EXAMPLE 10

Production of compound 6 ($R^1$=nitro, $R^2$,$R^3$= methoxymethyl)

2,2-bis(Methoxymethyl)-6-nitro-2H-1-benzopyran obtained in Preparative Example 9 was treated in the same manner as in Preparative Example 4 to give 3,4-epoxy-3,4-dihydro-2,2-bis(methoxymethyl)-6-nitro-2H-1-benzopyran.

An optically active compound, (3S,4S)-3,4-epoxy-3,4-dihydro-6-nitro-2,2-bis(methoxymethyl)-2H-1-benzopyran, was obtained by oxidation using an Mn(III)-Salen (S,S) complex as in Preparative Example 5.

$^1$H-NMR(CDCl$_3$/ppm) δ3.26(3H, s), 3.48(3H, s), 3.57–3.76(4H, m), 3.84(1H, d, J=3.0 Hz), 4.02(1H, d, J=3.0 Hz), 6.93(1H, d, J=9.0 Hz), 8.14(1H, dd, J=3.0 Hz, 9.0 Hz), 8.30(1H, d, J=3.0 Hz).

PREPARATIVE EXAMPLE 11

Production of compound 3 ($R^1$=fluoro, $R^2$,$R^3$= methoxymethyl)

By treating 5-fluoro-2-hydroxyacetophenone in the same manner as in Preparative Example 1, 6-fluoro-3,4-dihydro-2,2-bis(methoxymethyl)-2H-1-benzopyran-4-one was obtained.

$^1$H-NMR(CDCl$_3$/ppm) δ2.89(2H, s), 3.36(6H, s), 3.56 (4H, s), 6.90–7.00(1H, m), 7.10–7.25(1H, m), 7.45–7.55 (1H, m).

PREPARATIVE EXAMPLE 12

Production of compound 4 ($R^1$=fluoro, $R^2$,$R^3$= methoxymethyl)

6-Fluoro-3,4-dihydro-2,2-bis(methoxymethyl)-2H-1-benzopyran-4-one obtained in Preparative Example 11 was treated in the same manner as in Preparative Example 2 to give 6-fluoro-3,4-dihydro-2,2-bis(methoxymethyl)-2H-1-benzopyran-4-ol.

$^1$H-NMR(CDCl$_3$/ppm) δ2.06(1H, dd, J=5.5 Hz, 14.4 Hz), 2.28(1H, dd, J=5.5 Hz, 14.4 Hz), 3.08(1H), 3.36(3H, s), 3.39(3H, s), 3.42(1H, d, J=10.0 Hz), 3.48(1H, d, J=10.0 Hz), 3.57(1H, d, J=10.4 Hz), 3.75(1H, d, J=10.4 Hz), 4.70–4.80 (1H, m), 6.75–6.90(2H, m), 7.09(1H, dd, J=2.9 Hz, 8.8 Hz).

PREPARATIVE EXAMPLE 13

Production of compound 5 ($R^1$=fluoro, $R^2$,$R^3$= methoxymethyl)

6-Fluoro-3,4-dihydro-2,2-bis(methoxymethyl)-2H-1-benzopyran-4-ol obtained in Preparative Example 12 was treated in the same manner as in Preparative Example 3 to give 6-fluoro-2,2-bis(methoxymethyl)-2H-1-benzopyran.

$^1$H-NMR(CDCl$_3$/ppm) δ3.39(6H, s), 3.51–3.65(4H, m), 5.73(1H, d, J=10.0 Hz), 6.44(1H, d, J=10.0 Hz), 6.67–6.70 (1H, m), 6.76–6.80(2H, m).

PREPARATIVE EXAMPLE 14

Production of compound 6 ($R^1$=fluoro, $R^2$,$R^3$= methoxymethyl)

6-Fluoro-2,2-bis(methoxymethyl)-2H-1-benzopyran obtained in Preparative Example 13 was treated in the same manner as in Preparative Example 4 to give 3,4-epoxy-6-fluoro-3,4-dihydro-2,2-bis(methoxymethyl)-2H-1-benzopyran.

$^1$H-NMR(CDCl$_3$/ppm) δ3.30(3H, s), 3.48(3H, s), 3.52–3.77(5H, m), 3.86(1H, d, J=6.0 Hz), 6.78–6.83(1H, m), 6.90–6.95(1H, m), 7.04–7.08(1H, m).

PREPARATIVE EXAMPLE 15

Production of compound 3 (R$^1$=bromo, R$^2$,R$^3$=methoxymethyl)

By treating 5-bromo-2-hydroxyacetophenone in the same manner as in Preparative Example 1, 6-bromo-3,4-dihydro-2,2-bis(methoxymethyl)-2H-1-benzopyran-4-one was obtained.

$^1$H-NMR(CDCl$_3$/ppm) δ2.89(2H, s), 3.36(6H, s), 3.55 (4H, s), 6.89(1H, d, J=8.8 Hz), 7.53(1H, dd, J=2.5 Hz, 8.8 Hz), 7.95(1H, d, J=2.6 Hz).

PREPARATIVE EXAMPLE 16

Production of compound 4 (R$^1$=bromo, R$^2$,R$^3$=methoxymethyl)

6-Bromo-3,4-dihydro-2,2-bis(methoxymethyl)-2H-1-benzopyran-4-one obtained in Preparative Example 15 was treated in the same manner as in Preparative Example 2 to give 6-bromo-3,4-dihydro-2,2-bis(methoxymethyl)-2H-1-benzopyran-4-ol.

$^1$H-NMR(CDCl$_3$/ppm) δ2.08(1H, dd), 2.28(1H, dd), 3.20 (1H), 3.36(3H, s), 3.39(3H, s), 3.43(1H, d), 3.47(1H, d), 3.59(1H, d), 3.64(1H, d), 4.73(1H, m), 6.76(1H, d), 7.25(1H, dd), 7.51(1H, d).

PREPARATIVE EXAMPLE 17

Production of compound 5 (R$^1$=bromo, R$^2$,R$^3$=methoxymethyl)

6-Bromo-3,4-dihydro-2,2-bis(methoxymethyl)-2H-1-benzopyran-4-ol obtained in Preparative Example 16 was treated in the same manner as in Preparative Example 3 to give 6-bromo-2,2-bis(methoxymethyl)-2H-1-benzopyran.

$^1$H-NMR(CDCl$_3$/ppm) δ3.39(6H, s), 3.54(2H, d), 3.60 (2H, d), 5.71(1H, d), 6.43(1H, d), 6.72(1H, d), 7.08(1H, d), 7.19(1H, dd).

PREPARATIVE EXAMPLE 18

Production of compound 6 (R$^1$=bromo, R$^2$,R$^3$=methoxymethyl)

6-Bromo-2,2-bis(methoxymethyl)-2H-1-benzopyran obtained in Preparative Example 17 was treated in the same manner as in Preparative Example 5 to give 6.8 g of (3S,4S)-6-bromo-3,4-epoxy-3,4-dihydro-2,2-bis (methoxyethyl)-2H-1-benzopyran.

$^1$H-NMR(CDCl$_3$/ppm) δ3.29(3H, s), 3.48(3H, s), 3.47–3.87(6H, m), 6.75(1H, d, J=8.8 Hz), 7.33(1H, dd, J=2.6 Hz, 8.8 Hz), 7.45(1H, d, J=2.6 Hz).

PREPARATIVE EXAMPLE 19

Production of 3-amino-1-methyl-1,6-dihydropyridazine-6-thione

Pyridine (5 ml) and a Lawesson's reagent (970 mg, 2.4 mmol) were added to 3-amino-1-methyl-1,6-dihydropyridazin-6-one (500 mg, 4 mmol) as described in Journal of Medicinal Chemistry, 34 (10), 3074 (1991), and the mixture was refluxed under heating for 5 hours. The reaction mixture was concentrated and the residue obtained was subjected to silica gel column chromatography (chloroform:methanol=100:1) to give 218 mg of 3-amino-1-methyl-1,6-dihydropyridazine-6-thione.

$^1$H-NMR(DMSO-d$_6$/ppm) δ3.85(3H, s), 6.43(2H, br s), 6.72(1H, d, J=9.0 Hz), 7.42(1H, d, J=9.0 Hz).

PREPARATIVE EXAMPLE 20

Production of 8-amino-1,2,3,4-tetrahydro-1,4,6-trimethylpyrazino[2,3-d]pyridazin-5(6H)-one Water (9 ml) and N,N'-dimethylethylenediamine (0.8 ml, 7.7 mmol) were added to 6-amino-4,5-dichloro-2-methyl-3 (2H)-pyridazinone (500 mg, 2.6 mmol) as described in Chemical Pharmaceutical Bulletin, 30, 832 (1982), and the mixture was refluxed under heating for 3 hours. The reaction mixture was concentrated, added with chloroform, washed with water and brine and dried over anhydrous sodium sulfate. The solvent was distilled away and the residue obtained was subjected to silica gel column chromatography (chloroform:methanol=40:1) to give 448 mg of 8-amino-1,2,3,4-tetrahydro-1,4,6-trimethylpyrazino[2,3-d]pyridazin-5 (6H)-one.

$^1$H-NMR(DMSO-d$_6$/ppm) δ2.53(3H, s), 2.73–2.76(2H, m), 2.96–2.99(2H, m), 3.12(3H, s), 3.36(3H, s), 5.02(2H, br s).

PREPARATIVE EXAMPLE 21

Production of 3-amino-1,6-dihydropyridin-6-one

2-Hydroxy-5-nitropyridine (1 g) was dissolved in methanol (50 ml) and subjected to hydrogenation in the presence of 10% palladium-carbon (600 mg) at room temperature under 1 bar until the termination of hydrogen absorption. The insoluble material was filtered off and the filtrate was concentrated to give 785 mg of the title compound.

$^1$H-NMR(DMSO-d$_6$/ppm) δ4.23(2H, br s), 6.22(1H, d, J=9 Hz), 6.73(1H, s), 7.03(1H, d, J=9 Hz), 10.3–10.8(1H, br s).

PREPARATIVE EXAMPLE 22

Production of 1,6-dihydro-1-methyl-3-nitropyridin-6-one

Ethanol (70 ml), sodium hydroxide (856 mg) and methyl iodide (1.3 ml) were added to 2-hydroxy-5-nitropyridine (1 g) and the mixture was refluxed under heating for 5 hours. The reaction mixture was concentrated and added with chloroform. The insoluble material was filtered off and the filtrate was concentrated to give 1.85 g of the title compound.

$^1$H-NMR(DMSO-d$_6$/ppm) δ3.54(3H, s), 6.46(1H, d), 8.12 (1H, dd), 9.18(1H,d).

PREPARATIVE EXAMPLE 23

Production of 3-amino-1-methyl-1,6-dihydropyridin-6-one

Reduced iron (440 mg) and con. hydrochloric acid (0.02 ml) were added to a mixed solution of ethanol (6 ml) and water (6 ml), and the mixture was heated at 85° C. for 10 minutes. 1,6-Dihydro-1-methyl-3-nitropyridin-6-one (500 mg) obtained in Preparative Example 22 was portionwise added, and the mixture was stirred for 1 hour. A small amount of sodium carbonate was added to make the mixture slightly alkaline. The mixture was filtered while heating and the filtrate was concentrated to give 360 mg of the title compound.

$^1$H-NMR(DMSO-d$_6$/ppm) δ3.31(3H, s), 4.23(2H, br s), 6.23(1H, d, J=9 Hz), 6.83(1H, d, J=3 Hz), 7.04(1H, dd, J=3 Hz, 9 Hz).

PREPARATIVE EXAMPLE 24

Production of 1,6-dihydro-3-hydroxy-1,4,5-trimethylpyridazin-6-one 2,3-Dimethylmaleic anhydride (2.5 g) was dissolved in acetic acid (45 ml) and methylhydrazine (960 mg) was added. The mixture was stirred at room temperature for 2 hours. Acetic acid was distilled away and the residue obtained was recrystallized from dichloromethane-hexane to give 2.6 g of the title compound.

$^1$H-NMR(DMSO-d$_6$/ppm) δ1.99(3H, s), 2.00(3H, s), 3.44 (3H, s).

EXAMPLE 1

(−)-(3S,4R)-6-Cyano-3,4-dihydro-4-[(1,6-dihydro-1-methyl-6-oxo-3-pyridazinyl)amino]-2,2-bis (methoxymethyl)-2H-1-benzopyran-3-ol (3S,4S)-6-Cyano-3,4-epoxy-3,4-dihydro-2,2-bis (methoxymethyl)-2H-1-benzopyran (4.18 g, 16 mmol) obtained in Preparative Example 5 and 3-amino-1-methyl-1,6-dihydropyridazin-6-one (4.00 g, 32 mmol) as described in Journal of Medicinal Chemistry, 34(10), 3074 (1991) were dissolved in dimethylformamide (40 ml) and 60% sodium hydride (1.92 g, 48 mmol) was added at room temperature in an argon stream. After foaming came to an end, the mixture was allowed to react at 60° C. for 2 hours. Ice-water was poured in the reaction mixture and the mixture was extracted with chloroform. The organic layer was washed with saturated brine and dried over anhydrous sodium sulfate. The solvent was distilled away under reduced pressure to give a residue, which was purified by silica gel column chromatography (ethyl acetate:ethanol= 30:1-5:1) and recrystallized from ethyl acetate to give 4.34 g of the title compound (56%, 99.5% ee).

EXAMPLE 2

(−)-(3S,4R)-6-Cyano-3,4-dihydro-4-[(1,6-dihydro-1-methyl-6-oxo-3-pyridazinyl)oxy]-2,2-bis(methoxymethyl)-2H-1-benzopyran-3-ol (3S,4S)-6-Cyano-3,4-epoxy-3,4-dihydro-2,2-bis (methoxymethyl)-2H-1-benzopyran (280 mg, 1.07 mmol) obtained in Preparative Example 5 and 3-hydroxy-1-methyl-1,6-dihydropyridazin-6-one (142 mg, 1.13 mmol) as described in Journal of Organic Chemistry, 36(22), 3372 (1971) were dissolved in ethanol (2.8 ml), and pyridine (0.13 ml) was added. The mixture was refluxed under heating for 8.5 hours. The solvent was distilled away and the residue was purified by silica gel column chromatography (methanol:chloroform=1:99) to give 228 mg of the title compound (55%).

EXAMPLE 3

(−)-(3S,4R)-6-Cyano-3,4-dihydro-2,2-bis(methoxymethyl)-4-[3,4-dihydro-4-oxoquinazolin-2-ylthio]-2H-1-benzopyran-3-ol A reaction mixture containing 2-mercapto-4(3H) quinazoline (161 mg), 6-cyano-3,4-epoxy-3,4-dihydro-2,2-bis(methoxymethyl)-2H-1-benzopyran (200 mg) and sodium carbonate (241 mg), in methanol (3 ml), was stirred at room temperature for 4 hours. The reaction mixture was dried over anhydrous magnesium sulfate and concentrated, and the residue was purified by silica gel column chromatography (ethyl acetate:hexane:1:5) to give 241 mg of the title compound.

EXAMPLE 4

(−)-(3S,4R)-6-Cyano-4-(3-cyano-1H-indol-1-yl)-3,4-dihydro-2,2-bis(methoxymethyl)-2H-1-benzopyran-3-ol A reaction mixture containing 6-cyano-3,4-epoxy-3,4-dihydro-2,2-bis(methoxymethyl)-2H-1-benzopyran (300 mg), 3-cyanoindole (210 mg) and potassium carbonate (480 mg), in dimethylformamide (3 ml), was stirred at 80° C. for 2.5 hours. The reaction mixture was diluted with ethyl acetate, washed with water, 1N-hydrochloric acid, an aqueous solution of sodium hydrogencarbonate and brine, dried over anhydrous sodium sulfate and concentrated, and the residue was purified by silica gel column chromatography (ethyl acetate:hexane=1:2) to give 298 mg of the title compound.

The following compounds of Examples 5 and 6 were obtained by treating in the same manner as in any one of the above Examples.

EXAMPLE 5

(−)-(3S,4R)-4-[(6-Chloro-3-pyridazinyl)amino]-6-cyano-3, 4-dihydro-2,2-bis(methoxymethyl)-2H-1-benzopyran-3-ol

EXAMPLE 6

(+)-(3S,4R)-6-Cyano-4-(3-formyl-1H-indol-1-yl)-3,4-dihydro-2,2-bis(methoxymethyl)-2H-1-benzopyran-3-ol

EXAMPLES 7, 8

(−)-(3S,4R)-4-[(6-Acetyloxy-3-pyridazinyl)amino]-6-cyano-3,4-dihydro-2,2-bis(methoxymethyl)-2H-1-benzopyran-3-ol (Example 7)
(−)-(3S,4R)-6-Cyano-3,4-dihydro-4-[(1,6-dihydro-6-oxo-3-pyridazinyl)amino]-2,2-bis(methoxymethyl)-2H-1-benzopyran-3-ol (Example 8)

Potassium acetate (380 mg) and acetic acid (6 ml) were added to (−)-(3S,4R)-4-[(6-chloro-3-pyridazinyl)amino]-6-cyano-3,4-dihydro-2,2-bis(methoxymethyl)-2H-1benzopyran-3-ol (750 mg) obtained in Example 5, and the mixture was refluxed with stirring for 5 hours. The reaction mixture was filtered and the residue was washed with acetic acid. The residue obtained by removing the solvent from the filtrate under reduced pressure was purified by silica gel column chromatography (ethyl acetate:ethanol=95:5), whereby (−)-(3S,4R)-4-[(6-acetyloxy-3-pyridazinyl)amino] -6-cyano-3,4-dihydro-2,2-bis(methoxymethyl)-2H-1-benzopyran-3-ol (180 mg, 22.6%) and (−)-(3S,4R)-6-cyano-3,4-dihydro-4-[(1,6-dihydro-6-oxo-3-pyridazinyl)amino]-2, 2-bis(methoxymethyl)-2H-1-benzopyran-3-ol (500 mg, 69.9%) were obtained in the order of elution.

EXAMPLE 9

(−)-(3S,4R)-6-Cyano-3,4-dihydro-2,2-bis(methoxymethyl)-4-[3-(trans-β-nitro)vinyl-1H-indol-1-yl]-2H-1-benzopyran-3-ol Ammonium acetate (22 mg) and nitromethane (3 ml) were added to (+)-(3S,4R)-6-cyano-4-(3-formyl-1H-indol-1-yl)-3,4-dihydro-2,2-bis(methoxymethyl)-2H-1-benzopyran-3-ol (110 mg) obtained in Example 6, and the mixture was refluxed with stirring for 4 hours. Ammonium acetate (22 mg) and nitromethane (2 ml) were added, and the mixture was refluxed with stirring for 3 hours. Chloroform (200 ml) was added to the reaction mixture, and the mixture was washed with water and dried over anhydrous sodium sulfate. The solvent was distilled away under reduced pressure and the residue obtained was separated and purified by silica gel column chromatography (ethyl acetate:hexane= 3:7) to give 90 mg of the title compound (74.0%).

EXAMPLES 10, 11

(−)-(Z)-1-[(3S,4R)-6-Cyano-3,4-dihydro-2,2-bis (methoxymethyl)-3-hydroxy-2H-1-benzopyran-4-yl]-1H-indol-3-carboxyaldehydoxime (Example 10)

(−)-(E)-1-[(3S,4R)-6-Cyano-3,4-dihydro-2,2-bis(methoxymethyl)-3-hydroxy-2H-1-benzopyran-4-yl]-1H-indol-3-carboxyaldehydoxime (Example 11)

Hydroxylamine hydrochloride (260 mg) and pyridine (10 ml) were added to (+)-(3S,4R)-6-cyano-4-(3-formyl-1H-indol-1-yl)-3,4-dihydro-2,2-bis(methoxymethyl)-2H-1-benzopyran-3-ol (700 mg) obtained in Example 6, and the mixture was stirred at room temperature for 5 hours. Chloroform was added to the reaction mixture and the reaction mixture was washed with water and dried over anhydrous sodium sulfate. The solvent was distilled away under reduced pressure and the residue obtained was separated and purified by silica gel column chromatography (ethyl acetate:hexane=3:7), whereby (−)-(Z)-1-[(3S,4R)-6-cyano-3,4-dihydro-2,2-bis(methoxymethyl)-3-hydroxy-2H-1-benzopyran-4-yl]-1H-indol-3-carboxyaldehydoxime (293 mg, 40.4%) and (−)-(E)-1-[(3S,4R)-6-cyano-3,4-dihydro-2,2-bis(methoxymethyl)-3-hydroxy-2H-1-benzopyran-4-yl]-1H-indol-3-carboxyaldehydoxime (430 mg, 59.2%) were obtained in the order of elution.

The following compounds of Example 12 to Example 27 were obtained by treating in the same manner as in any one of the above Examples.

EXAMPLE 12

Using methyl pyrazol-4-carboxylate obtained in Preparative Example 6, (−)-(3S,4R)-6-cyano-3,4-dihydro-4-(4-methoxycarbonyl-1H-pyrazol-1-yl)-2,2-bis(methoxymethyl)-2H-1-benzopyran-3-ol was obtained.

EXAMPLE 13

(−)-(3S,4R)-6-Cyano-4-[(1-ethyl-1,6-dihydro-6-oxo-3-pyridazinyl)amino]-3,4-dihydro-2,2-bis(methoxymethyl)-2H-1-benzopyran-3-ol

EXAMPLE 14

(−)-(3S,4R)-6-Cyano-3,4-dihydro-4-[(1,6-dihydro-1-isopropyl-6-oxo-3-pyridazinyl)amino]-2,2-bis(methoxymethyl)-2H-1-benzopyran-3-ol

EXAMPLE 15

(−)-(3S,4R)-6-Cyano-4-(5-cyano-1H-indol-1-yl)-3,4-dihydro-2,2-bis(methoxymethyl)-2H-1-benzopyran-3-ol

EXAMPLE 16

(+)-(3S,4R)-6-Cyano-3,4-dihydro-4-(3,4-dihydro-4-oxopyrimidin-3-yl)-2,2-bis(methoxymethyl)-2H-1-benzopyran-3-ol

EXAMPLE 17

(−)-(3S,4R)-6-Cyano-3,4-dihydro-2,2-bis(methoxymethyl)-4-phenoxy-2H-1-benzopyran-3-ol

EXAMPLE 18

(±)-trans-6-Cyano-3,4-dihydro-4-[(1,6-dihydro-1-methyl-6-oxo-3-pyridazinyl)amino]-2,2-bis(methoxymethyl)-2H-1-benzopyran-3-ol

EXAMPLE 19

(+)-(3S,4R)-6-Cyano-4-[(2-cyanophenyl)amino]-3,4-dihydro-2,2-bis(methoxymethyl)-2H-1-benzopyran-3-ol

EXAMPLE 20

(−)-(3S,4R)-6-Cyano-4-[(4-cyanophenyl)amino]-3,4-dihydro-2,2-bis(methoxymethyl)-2H-1-benzopyran-3-ol

EXAMPLE 21

(−)-(3S,4R)-6-Cyano-3,4-dihydro-2,2-bis(methoxymethyl)-4-[(pyrimidin-2-yl)amino]-2H-1-benzopyran-3-ol

EXAMPLE 22

(+)-(3S,4R)-6-Cyano-3,4-dihydro-4-(1,4-dihydro-4-oxopyridin-1-yl)-2,2-bis(methoxymethyl)-2H-1-benzopyran-3-ol

EXAMPLE 23

(−)-(3S,4R)-4-(4-Amino-1,2-dihydro-2-oxopyrimidin-1-yl)-6-cyano-3,4-dihydro-2,2-bis(methoxymethyl)-2H-1-benzopyran-3-ol

EXAMPLE 24

(−)-(3S,4R)-6-Cyano-3,4-dihydro-2,2-bis(methoxymethyl)-4-(4-nitrophenoxy)-2H-1-benzopyran-3-ol

EXAMPLE 25

(+)-(3S,4R)-6-Cyano-3,4-dihydro-2,2-bis(methoxymethyl)-4-(1H-1,2,4-triazol-3-ylthio)-2H-1-benzopyran-3-ol

EXAMPLE 26

(+)-(3S,4R)-6-Cyano-3,4-dihydro-2,2-bis(methoxymethyl)-4-(1-methyl-1H-imidazol-2-ylthio)-2H-1-benzopyran-3-ol

EXAMPLE 27

(+)-(3S,4R)-4-(3-Amino-4H-1,2,4-triazol-4-yl)-6-cyano-3,4-dihydro-2,2-bis(methoxymethyl)-2H-1-benzopyran-3-ol

EXAMPLE 28

(−)-(3S,4R)-6-Cyano-3,4-dihydro-4-[(1,6-dihydro-1-methyl-6-oxo-3-pyridazinyl)amino]-2,2-bis(methoxymethyl)-2H-1-benzopyran-3-ol ½ $H_2O$ (3S,4S)-6-Cyano-3,4-epoxy-3,4-dihydro-2,2-bis(methoxymethyl)-2H-1-benzopyran (56.75 g, 0.22 mol) obtained in Preparative Example 5 and 3-amino-1-methyl-1,6-dihydropyridazin-6-one (30.00 g, 0.24 mol) as described in Journal of Medicinal Chemistry, 34(10), 3074 (1991) were dissolved in dimethylformamide (300 ml), and 60% sodium hydride (17.4 g, 0.44 mol) were added at room temperature in an argon stream. After foaming came to an end, the mixture was allowed to react at 40° C. for 3 hours. Ice-water was poured in the reaction mixture and the mixture was extracted with chloroform. The organic layer was washed with saturated brine and dried over anhydrous sodium sulfate. The solvent was distilled away under reduced pressure to give a residue, which was purified by silica gel column chromatography (ethyl acetate:ethanol= 9:1), recrystallized from ethyl acetate, and recrystallized from water:ethanol (2:1) to give 32.0 g of the title compound (38%, 99.8% ee).

Elemental analysis Found:C (%) 57.59, H (%) 5.89, N (%) 14.11

Ultraviolet absorption spectrum (in methanol solution) $\lambda_{MAX}$:205.6 nm ($\epsilon$=31000), 245.6 nm ($\epsilon$=32000), 350 nm ($\epsilon$=1800)

The compounds of the following Examples 29–33 were obtained by treating in the same manner as in Example 1.

EXAMPLE 29

(3R,4R)-6-Cyano-3,4-epoxy-3,4-dihydro-2,2-bis(methoxymethyl)-2H-1-benzopyran obtained in Preparative Example 5 was treated in the same manner as in Example 1 to give (+)-(3R,4S)-6-cyano-3,4-dihydro-4-[(1,6-dihydro-1-methyl-6-oxo-3-pyridazinyl)amino]-2,2-bis(methoxymethyl)-2H-1-benzopyran-3-ol.

EXAMPLE 30

3,4-Epoxy-6-fluoro-3,4-dihydro-2,2-bis(methoxymethyl)-2H-1-benzopyran obtained in Preparative Example 14 was treated in the same manner as in Example 1 to give trans-6-fluoro-3,4-dihydro-4-[(1,6-dihydro-1-methyl-6-oxo-3-pyridazinyl)amino]-2,2-bis(methoxymethyl)-2H-1-benzopyran-3-ol.

EXAMPLE 31

(3S,4S)-6-Bromo-3,4-epoxy-3,4-dihydro-2,2-bis(methoxymethyl)-2H-1-benzopyran obtained in Preparative Example 18 was treated in the same manner as in Example 1 to give (−)-(3S,4R)-6-bromo-3,4-dihydro-4-[(1,6-dihydro-1-methyl-6-oxo-3-pyridazinyl)amino]-2,2-bis(methoxymethyl)-2H-1-benzopyran-3-ol.

EXAMPLE 32

3,4-Epoxy-3,4-dihydro-2,2-bis(methoxymethyl)-6-nitro-2H-1-benzopyran obtained in Preparative Example 10 was treated in the same manner as in Example 1 to give trans-4-[(6-chloro-3-pyridazinyl)amino]-3,4-dihydro-2,2-bis(methoxymethyl)-6-nitro-2H-1-benzopyran-3-ol.

EXAMPLE 33

3-Amino-6-pyridazinol described in Chemical Pharmaceutical Bulletin, 10, 580 (1962) was treated in the same manner as in Example 1 to give (−)-(3S,4R)-4-(3-amino-1,6-dihydro-6-oxopyridazin-1-yl)-6-cyano-3,4-dihydro-2,2-bis(methoxymethyl)-2H-1-benzopyran-3-ol.

EXAMPLE 34

(−)-(3S,4R)-6-Cyano-3,4-dihydro-4-[(3,4,7,8-tetrahydro-4,7-dimethyl-8-oxo-2H-pyridazino[4,5-b]-1,4-oxazin-5-yl)amino]-2,2-bis(methoxymethyl)-2H-1-benzopyran-3-ol (3S,4S)-6-Cyano-3,4-epoxy-3,4-dihydro-2,2-bis(methoxymethyl)-2H-1-benzopyran (87 mg, 0.33 mmol) obtained in Preparative Example 5 and 5-amino-3,4-dihydro-4,7-dimethyl-2H-pyridazino[4,5-b]-1,4-oxazin-8(7H)-one (98 mg, 0.5 mmol) as described in Chemical Pharmaceutical Bulletin, 30, 832 (1982) were dissolved in dimethylformamide (3 ml), and potassium t-butoxide (112 mg, 1.0 mmol) was added under ice-cooling in a nitrogen stream. The mixture was reacted for 10 minutes at room temperature and ice-water was added to the reaction mixture. The resulting mixture was extracted with chloroform, and the organic layer was washed with saturated brine and dried over anhydrous sodium sulfate. The solvent was distilled away under reduced pressure to give a residue. The residue was purified by silica gel column chromatography (chloroform: methanol=50:1-20:1) to give 126 mg of the title compound (83%).

The compounds of the following Examples 35–44 were obtained by treating in the same manner as in Example 34.

EXAMPLE 35

8-Amino-3,4-dihydro-4,6-dimethyl-2H-pyridazino[4,5-b]-1,4-oxazin-5(6H)-one as described in Chemical Pharmaceutical Bulletin, 30, 832 (1982) was treated in the same manner as in Example 34 to give (−)-(3S,4R)-6-cyano-3,4-dihydro-4-[(3,4,5,6-tetrahydro-4,6-dimethyl-5-oxo-2H-pyridazino[4,5-b]-1,4-oxazin-8-yl)amino]-2,2-bis(methoxymethyl)-2H-1-benzopyran-3-ol.

EXAMPLE 36

8-Amino-1,2,3,4-tetrahydro-1,4,6-trimethylpyrazino[2,3-d]pyridazin-5(6H)-one obtained in Preparative Example 20 was treated in the same manner as in Example 34 to give (−)-(3S,4R)-6-cyano-3,4-dihydro-4-[(1,2,3,4,5,6-hexahydro-1,4,6-trimethyl-5-oxopyrazino[2,3-d]pyridazin-8-yl)amino]-2,2-bis(methoxymethyl)-2H-1-benzopyran-3-ol.

EXAMPLE 37

4-Amino-2-methylphthalazin-1(2H)-one described in Journal of the Chemical Society; Perkin Transactions I, 2820 (1972) was treated in the same manner as in Example 34 to give (−)-(3S,4R)-6-cyano-3,4-dihydro-4-[(3,4-dihydro-3-methyl-4-oxophthalazin-1-yl)amino]-2,2-bis(methoxymethyl)-2H- 1-benzopyran-3-ol.

EXAMPLE 38

3-Amino-1-methyl-1,6-dihydropyridazine-6-thione obtained in Preparative Example 19 was treated in the same manner as in Example 34 to give (−)-(3S,4R)-6-cyano-3,4-dihydro-4-[(1,6-dihydro-1-methyl-6-thioxo-3-pyridazinyl)amino]-2,2-bis(methoxymethyl)-2H-1-benzopyran-3-ol.

EXAMPLE 39

(3S,4S)-3,4-Epoxy-3,4-dihydro-2,2-bis(methoxymethyl)-6-nitro-2H-1-benzopyran obtained in Preparative Example 10 was treated in the same manner as in Example 34 to give (+)-(3S,4R)-3,4-dihydro-4-[(1,6-dihydro-1-methyl-6-oxo-3-pyridazinyl)amino]-2,2-bis(methoxymethyl)-6-nitro-2H-1-benzopyran-3-ol.

EXAMPLE 40

3,4-Epoxy-6-fluoro-3,4-dihydro-2,2-bis(methoxymethyl)-2H-1-benzopyran obtained in Preparative Example 14 was treated in the same manner as in Example 34 to give trans-4-[(6-chloro-3-pyridazinyl)amino]-6-fluoro-3,4-dihydro-2,2-bis(methoxymethyl)-2H-1-benzopyran-3-ol.

EXAMPLE 41

3,4-Epoxy-6-fluoro-3,4-dihydro-2,2-bis(methoxymethyl)-2H-1-benzopyran obtained in Preparative Example 14 and 4-amino-2-methylphthalazin-1(2H)-one described in Journal of the Chemical Society; Perkin Transactions I, 2820 (1972) were treated in the same manner as in Example 34 to give trans-6-fluoro-3,4-dihydro-4-[(3,4-dihydro-3-methyl-4-oxophthalazin-1-yl)amino]- 2,2-bis(methoxymethyl)-2H-1-benzopyran-3-ol.

EXAMPLE 42

(−)-(3S,4R)-6-Cyano-3,4-dihydro-2,2-bis(methoxymethyl)-4-(2-pyridylamino)-2H-1-benzopyran-3-ol

EXAMPLE 43

(−)-(3S,4R)-6-Cyano-3,4-dihydro-2,2-bis(methoxymethyl)-4-(3-pyridylamino)-2H-1-benzopyran-3-ol

EXAMPLE 44

(−)-(3S,4R)-6-Cyano-3,4-dihydro-2,2-bis(methoxymethyl)-4-(4-pyridylamino)-2H-1-benzopyran-3-ol

EXAMPLE 45 trans-4-[(6-Chloro-3-pyridazinyl)amino]-6-fluoro-3,4-dihydro-2,2-bis(methoxymethyl)-2H-1-benzopyran-3-ol obtained in Example 40 was treated in the same manner as in Example 8 to give trans-6-fluoro-3,4-dihydro-4-[(1,6-dihydro-6-oxo-3-pyridazinyl)amino]-2,2-bis(methoxymethyl)-2H-1-benzopyran-3-ol.

EXAMPLE 46

(3S,4R)-6-Cyano-3,4-dihydro-4-[(1,6-dihydro-1-methyl-6-oxo-3-pyridyl)amino]-2,2-bis(methoxymethyl)-2H-1-benzopyran-3-ol 6-Cyano-3,4-epoxy-3,4-dihydro-2,2-bis(methoxymethyl)-2H-1-benzopyran (380 mg) obtained in Preparative Example 4 was dissolved in dimethylformamide (5 ml) and 3-amino-1-methyl-1,6-dihydropyridin-6-one (90 mg) obtained in Preparative Example 23 and triethylamine (1 ml) were added. The mixture was refluxed under heating for 30 hours. The reaction mixture was concentrated and the residue was purified by silica gel column chromatography (chloroform:methanol=20:1) to give 125 mg of the title compound.

EXAMPLE 47

3-Amino-1,6-dihydropyridin-6-one obtained in Preparative Example 21 was treated in the same manner as in Example 46 to give the following compound.
(3S,4R)-6-Cyano-3,4-dihydro-4-[(1,6-dihydro-6-oxo-3-pyridyl)-amino]-2,2-bis(methoxymethyl)-2H-1-benzopyran-3-ol

EXAMPLE 48

(−)-(3S,4R)-6-Cyano-3,4-dihydro-4-[(1,6-dihydro-6-oxo-1-n-propyl-3-pyridazinyl)amino]-2,2-bis(methoxymethyl)-2H-1-benzopyran-3-ol (−)-(3S,4R)-6-Cyano-3,4-dihydro-4-[(1,6-dihydro-6-oxo-3-pyridazinyl)amino]-2,2-bis(methoxymethyl)-2H-1-benzopyran-3-ol (60 mg, 0.16 mmol) obtained in Example 8 and 1-bromopropane (0.017 ml, 0.19 mmol) were dissolved in dimethylformamide (1.0 ml). Potassium carbonate (45 mg) was added and the mixture was reacted at 70° C. for 3 hours. Water was added to the reaction mixture and the mixture was extracted with ethyl acetate. The organic layer was washed with saturated brine and dried over anhydrous sodium sulfate. The solvent was distilled away under reduced pressure to give a residue. The residue was purified by silica gel column chromatography (methanol:chloroform=4:96) to give 33 mg of the title compound (50%).

The compounds of the following Examples 49–67 were obtained by the treatment in the same manner as in Example 48.

EXAMPLE 49

(−)-(3S,4R)-6-Cyano-4-[(1-cyclopropylmethyl-1,6-dihydro-6-oxo-3-pyridazinyl)amino]-3,4-dihydro-2,2-bis(methoxymethyl)-2H-1-benzopyran-3-ol

EXAMPLE 50

(−)-(3S,4R)-6-Cyano-3,4-dihydro-4-[(1,6-dihydro-1-(2-methoxyethyl)-6-oxo-3-pyridazinyl)amino]-2,2-bis(methoxymethyl)-2H-1-benzopyran-3-ol

EXAMPLE 51

(−)-(3S,4R)-6-Cyano-3,4-dihydro-4-[(1,6-dihydro-1-n-heptyl-6-oxo-3-pyridazinyl)amino]-2,2-bis(methoxymethyl)-2H-1-benzopyran-3-ol

EXAMPLE 52

(−)-(3S,4R)-4-[(1-Allyl-1,6-dihydro-6-oxo-3-pyridazinyl)-amino]-6-cyano-3,4-dihydro-2,2-bis(methoxymethyl)-2H-1-benzopyran-3-ol

EXAMPLE 53

(−)-(3S,4R)-6-Cyano-3,4-dihydro-4-[(1,6-dihydro-1-(methoxycarbonylmethyl)-6-oxo-3-pyridazinyl)amino]-2,2-bis(methoxymethyl)-2H-1-benzopyran-3-ol

EXAMPLE 54

(−)-(3S,4R)-6-Cyano-3,4-dihydro-4-[(1,6-dihydro-1-(4-nitrophenyl)-6-oxo-3-pyridazinyl)amino]-2,2-bis(methoxymethyl)-2H-1-benzopyran-3-ol

EXAMPLE 55

(−)-(3S,4R)-6-Cyano-3,4-dihydro-4-[(1,6-dihydro-1-(2-nitrophenyl)-6-oxo-3-pyridazinyl)amino]-2,2-bis(methoxymethyl)-2H-1-benzopyran-3-ol

EXAMPLE 56

(3S,4R)-4-[(1-Benzyloxycarbonylmethyl)-1,6-dihydro-6-oxo-3-pyridazinyl)amino]-6-cyano-3,4-dihydro-2,2-bis(methoxymethyl)-2H-1-benzopyran-3-ol

EXAMPLE 57

(−)-(3S,4R)-6-Cyano-3,4-dihydro-4-[(1,6-dihydro-1-(2-methylthioethyl)-6-oxo-3-pyridazinyl)amino]-2,2-bis(methoxymethyl)-2H-1-benzopyran-3-ol

EXAMPLE 58

(3S,4R)-6-Cyano-3,4-dihydro-4-[(1,6-dihydro-1-(2-(dimethylamino)ethyl)-6-oxo-3-pyridazinyl)amino]-2,2-bis(methoxymethyl)-2H-1-benzopyran-3-ol

EXAMPLE 59

(−)-(3S,4R)-6-Cyano-4-[(1-cyanomethyl-1,6-dihydro-6-oxo-3-pyridazinyl)amino]-3,4-dihydro-2,2-bis(methoxymethyl)-2H-1-benzopyran-3-ol

EXAMPLE 60

(−)-(3S,4R)-4-[(1-Benzyl-1,6-dihydro-6-oxo-3-pyridazinyl)amino]-6-cyano-3,4-dihydro-2,2-bis(methoxymethyl)-2H-1-benzopyran-3-ol

EXAMPLE 61

(−)-(3S,4R)-4-[(1-(2-(E)-Butenyl)-1,6-dihydro-6-oxo-3-pyridazinyl)amino]-6-cyano-3,4-dihydro-2,2-bis(methoxymethyl)-2H-1-benzopyran-3-ol

EXAMPLE 62

(−)-(3S,4R)-6-Cyano-4-[(1-(2-fluoroethyl)-1,6-dihydro-6-oxo-3-pyridazinyl)amino]-3,4-dihydro-2,2-bis(methoxymethyl)-2H-1-benzopyran-3-ol

EXAMPLE 63

(−)-(3S,4R)-6-Cyano-4-[(1-(2,2,2-trifluoroethyl)-1,6-dihydro-6-oxo-3-pyridazinyl)amino]-3,4-dihydro-2,2-bis(methoxymethyl)-2H-1-benzopyran-3-ol

EXAMPLE 64 trans-6-Fluoro-3,4-dihydro-4-[(1,6-dihydro-6-oxo-3-pyridazinyl)amino]-2,2-bis(methoxymethyl)-2H-1- benzopyran-3-ol obtained in Example 45 was treated in the same manner as in Example 48 to give trans-6-fluoro-3,4-dihydro-4-[(1,6-dihydro-6-oxo-1-n-propyl-3-pyridazinyl) amino]-2,2-bis(methoxymethyl)-2H-1-benzopyran-3-ol.

EXAMPLE 65 trans-6-Fluoro-3,4-dihydro-4-[(1,6-dihydro-6-oxo-3-pyridazinyl)amino]-2,2-bis(methoxymethyl)-2H-1-benzopyran-3-ol obtained in Example 45 was treated in the same manner as in Example 48 to give trans-4-[(1-(2-(E)-butenyl)-1,6-dihydro-6-oxo-3-pyridazinyl)amino]-6-fluoro-3,4-dihydro-2,2-bis(methoxymethyl)-2H-1-benzopyran-3-ol.

EXAMPLE 66 trans-6-Fluoro-3,4-dihydro-4-[(1,6-dihydro-6-oxo-3-pyridazinyl)amino]-2,2-bis(methoxymethyl)-2H-1-benzopyran-3-ol obtained in Example 45 was treated in the same manner as in Example 48 to give trans-4-[(1-allyl-1,6-dihydro-6-oxo-3-pyridazinyl)amino]-6-fluoro-3,4-dihydro-2,2-bis(methoxymethyl)-2H-1-benzopyran-3-ol.

EXAMPLE 67

(3S,4R)-6-Cyano-3,4-dihydro-4-[(1,6-dihydro-6-oxo-3-pyridyl)amino]-2,2-bis(methoxymethyl)-2H-1-benzopyran-3-ol obtained in Example 47 was treated in the same manner as in Example 48 to give (3S,4R)-6-cyano-4-[(1-ethyl-1,6-dihydro-6-oxo-3-pyridyl)amino]-3,4-dihydro-2,2-bis(methoxymethyl)-2H-1-benzopyran-3-ol.

EXAMPLES 68, 69

(−)-(3S,4R)-6-Cyano-3,4-dihydro-4-[(1,6-dihydro-1-(2-methylsulfonylethyl)-6-oxo-3-pyridazinyl)amino]-2,2-bis(methoxymethyl)-2H-1-benzopyran-3-ol (Example 68)
(+)-(3S,4R)-6-Cyano-3,4-dihydro-4-[(1,6-dihydro-1-(2-methylsulfinylethyl)-6-oxo-3-pyridazinyl)amino]-2,2-bis(methoxymethyl)-2H-1-benzopyran-3-ol (Example 69)

(−)-(3S,4R)-6-Cyano-3,4-dihydro-4-[(1,6-dihydro-1-(2-methylthioethyl)-6-oxo-3-pyridazinyl)amino]-2,2-bis(methoxymethyl)-2H-1-benzopyran-3-ol (262 mg) obtained in Example 57 was dissolved in dichloromethane (20 ml), and m-chloroperbenzoic acid (152 mg) was added under ice-cooling. The mixture was reacted for 30 minutes. The reaction mixture was poured in a saturated aqueous solution of sodium hydrogen carbonate and extracted with chloroform. The organic layer was washed with saturated brine and dried over anhydrous sodium sulfate. The solvent was distilled away under reduced pressure to give a residue. The residue was purified by silica gel column chromatography (chloroform:methanol=30:1-20:1) to give 182 mg (65%) and 89 mg (33%) of the title compounds, respectively.

EXAMPLE 70

(−)-(3S,4R)-6-Cyano-4-[(1-(2-cyanoethyl)-1,6-dihydro-6-oxo-3-pyridazinyl)amino]-3,4-dihydro-2,2-bis(methoxymethyl)-2H-1-benzopyran-3-ol (−)-(3S,4R)-6-Cyano-3,4-dihydro-4-[(1,6-dihydro-6-oxo-3-pyridazinyl)amino]-2,2-bis(methoxymethyl)-2H-1-benzopyran-3-ol (150 mg, 0.40 mmol) obtained in Example 8 and acrylonitrile (0.055 ml, 0.806 mmol) were dissolved in dimethylformamide (3 ml). Potassium carbonate (111 mg) was added and the mixture was reacted at 50° C. overnight. Water was added to the reaction mixture and the mixture was extracted with ethyl acetate. The organic layer was washed with saturated brine and dried over anhydrous sodium sulfate. The solvent was distilled away under reduced pressure and the residue was purified by silica gel column chromatography (methanol:chloroform=1:30) to give 99 mg of the title compound (58%).

The compounds of the following Examples 71–75 were obtained by treating in the same manner as in Example 70.

EXAMPLE 71

Methyl acrylate was treated in the same manner as in EXAMPLE 70 to give (−)-(3S,4R)-6-cyano-3,4-dihydro-4-[(1,6-dihydro-1-(2-methoxycarbonylethyl)-6-oxo-3-pyridazinyl)-amino]-2,2-bis(methoxymethyl)-2H-1-benzopyran-3-ol.

EXAMPLE 72 trans-6-Fluoro-3,4-dihydro-4-[(1,6-dihydro-6-oxo-3-pyridazinyl)amino]-2,2-bis(methoxymethyl)-2H-1-benzopyran-3-ol obtained in Example 45 was treated in the same manner as in Example 70 to give trans-4-[(1-(2-cyanoethyl)-1,6-dihydro-6-oxo-3-pyridazinyl)amino]-6-fluoro-3,4-dihydro-2,2-bis(methoxymethyl)-2H-1-benzopyran-3-ol.

EXAMPLE 73 trans-6-Fluoro-3,4-dihydro-4-[(1,6-dihydro-1-(2-methoxycarbonylethyl)-6-oxo-3-pyridazinyl)amino]-2,2-bis(methoxymethyl)-2H-1-benzopyran-3-ol

EXAMPLE 74

(3S,4R)-6-Cyano-3,4-dihydro-4-[(1,6-dihydro-6-oxo-3-pyridyl)amino]-2,2-bis(methoxymethyl)-2H-1-benzopyran-3-ol obtained in Example 47 was treated in the same manner as in Example 70 to give (3S,4R)-6-cyano-4-[(1-(2-cyanoethyl)-1,6-dihydro-6-oxo-3-pyridyl)amino]-3,4-dihydro-2,2-bis(methoxymethyl)-2H-1-benzopyran-3-ol.

EXAMPLE 75

(3S,4R)-6-Cyano-3,4-dihydro-4-[(1,6-dihydro-6-oxo-3-pyridyl)amino]-2,2-bis(methoxymethyl)-2H-1-benzopyran-3-ol obtained in Example 47 was treated in the same manner as in Example 70 to give (3S,4R)-6-cyano-3,4-dihydro-4-[(1,6-dihydro-1-(2-methoxycarbonylethyl)-6-oxo-3-pyridyl) amino]-2,2-bis(methoxymethyl)-2H-1-benzopyran-3-ol.

EXAMPLE 76

(−)-(3S,4R)-6-Cyano-3,4-dihydro-4-[(1,6-dihydro-6-oxo-1-(2-nitroethyl)-3-pyridazinyl)amino]-2,2-bis(methoxymethyl)-2H-1-benzopyran-3-ol Nitroethanol (0.79 ml) was dissolved in anhydrous dichloromethane. Under argon atmosphere, methanesulfonyl chloride (1.02 ml) and pyridine (1.07 ml) were added and the mixture was stirred overnight at room temperature. Ice-water was added and the mixture was extracted with chloroform. The organic layer was washed with saturated brine and dried over anhydrous sodium sulfate. The solvent was distilled away under reduced pressure. The obtained residue (45 mg) and (−)-(3S,4R)-6-cyano-3,4-dihydro-4-[(1,6-dihydro-6-oxo-3-pyridazinyl)-amino]-2,2-bis(methoxymethyl)-2H-1-benzopyran-3-ol (50 mg) obtained in Example 8 were dissolved in dimethylformamide (1.5 ml). Potassium carbonate (37 mg) was added and the mixture was refluxed under heating at 100° C. for 4 hours. Ice-water was added and the mixture was extracted with chloroform. The organic layer was washed with saturated brine and dried over anhydrous sodium sulfate. The solvent was distilled away under reduced pressure and the residue obtained was purified by silica gel column chromatography (chloroform:methanol=20:1) to give 42 mg of the title compound (70%).

EXAMPLE 77

(−)-(3S,4R)-6-Cyano-4-[(1-(4-diethylamino-2-butyn-1-yl)-1,6-dihydro-6-oxo-3-pyridazinyl)amino]-3,4-dihydro- 2,2-bis(methoxymethyl)-2H-1-benzopyran-3-ol (−)-(3S,4R)-6-Cyano-3,4-dihydro-4-[(1,6-dihydro-6-oxo-3-pyridazinyl)amino]-2,2-bis(methoxymethyl)-2H-1-benzopyran-3-ol (556 mg, 1.5 mmol) obtained in Example 8 and 1,4-dichloro-2-butyne (2.9 ml, 30 mmol) were dissolved in dimethylformamide (10 ml). Potassium carbonate (413 mg) was added and the mixture was reacted at 120° C. overnight. Water was added to the reaction mixture and the mixture was extracted with chloroform. The organic layer was washed with saturated brine and dried over anhydrous sodium sulfate. The solvent was distilled away under reduced pressure. The residue obtained was purified by silica gel column chromatography (methanol:chloroform=1:30) to give 171 mg of crude (3S,4R)-6-cyano-4-[(1-(4-chloro-2-butyn-1-yl)-1,6-dihydro-6-oxo-3-pyridazinyl)amino]-3,4-dihydro-2,2-bis(methoxymethyl)-2H-1-benzopyran-3-ol. The compound was dissolved in dimethylformamide (3 ml), added with diethylamine and stirred at 70° C. for 2.5 hours. Water was added and the mixture was extracted with chloroform. The organic layer was washed with saturated brine and dried over anhydrous sodium sulfate. The solvent was distilled away under reduced pressure. The residue obtained was purified by silica gel column chromatography (chloroform:methanol=20:1) to give 71 mg of the title compound (38%).

EXAMPLE 78

(−)-(3S,4R)-4-[(1-Carboxymethyl-1,6-dihydro-6-oxo-3-pyridazinyl)amino]-6-cyano-3,4-dihydro-2,2-bis(methoxymethyl)- 2H-1-benzopyran-3-ol (−)-(3S,4R)-4-[(1-Benzyloxycarbonylmethyl)-1,6-dihydro-6-oxo-3-pyridazinyl)amino]-6-cyano-3,4-dihydro-2,2-bis(methoxymethyl)-2H-1-benzopyran-3-ol (186 mg) obtained in Example 56 was dissolved in methanol (5 ml) and subjected to hydrogenation on 10% Pd—C (30 mg) at room temperature under 1 bar until the termination of hydrogen absorption. The insoluble material was filtered off and the filtrate was concentrated. Chloroform was added to the residue obtained and the mixture was made alkaline with a 0.1N aqueous solution of sodium hydroxide, and two layers were partitioned. The aqueous layer was made acidic with 1N hydrochloric acid and extracted with chloroform. The organic layer was washed with saturated brine and dried over anhydrous sodium sulfate. The solvent was distilled away under reduced pressure to give 45 mg of the title compound.

EXAMPLE 79

(−)-(3S,4R)-6-Cyano-4-[(4-fluorophenyl)amino]-3,4-dihydro-2,2-bis(methoxymethyl)-2H-1-benzopyran-3-ol (3S,4S)-6-Cyano-3,4-epoxy-3,4-dihydro-2,2-bis(methoxymethyl)-2H-1-benzopyran (200 mg, 0.76 mmol) obtained in Preparative Example 5 and p-fluoroaniline (250 mg, 2.2 mmol) were dissolved in methanol (1 ml), and the mixture was stirred at room temperature for 3 days. Water was added to the reaction mixture and the mixture was extracted with ethyl acetate. The extract was dried over anhydrous magnesium sulfate. The solvent was distilled away and the residue obtained was purified by silica gel column chromatography (ethyl acetate:hexane=1:4) to give 243 mg of the title compound (55%).

EXAMPLE 80

By treating in the same manner as in Example 79, (−)-(3S,4R)-6-cyano-4-[(4-fluoro-3-methylphenyl)amino]-3,4-dihydro-2,2-bis(methoxymethyl)-2H-1-benzopyran-3-ol was obtained.

EXAMPLE 81

(+)-2-[(3S,4R)-6-Cyano-3,4-dihydro-2,2-bis(methoxymethyl)-3-hydroxy-2H-1-benzopyran-4-ylamino]-pyridine-N-oxide (−)-(3S,4R)-6-Cyano-3,4-dihydro-2,2-bis(methoxymethyl)-4-(2-pyridylamino)-2H-1-benzopyran-3-ol (152 mg, 0.43 mmol) obtained in Example 42 was dissolved in dichloromethane (5 ml), and m-chloroperbenzoic acid (150 mg, purity 80%) was added under ice-cooling. The mixture was stirred for 1.5 hours. Dichloromethane was added to the reaction mixture, and the mixture was washed with saturated brine and dried over anhydrous sodium sulfate. The solvent was distilled away and the residue obtained was purified by silica gel column chromatography (methanol:chloroform=5:95) to give 94.5 mg of the title compound (59%).

EXAMPLE 82

(−)-(3S,4R)-6-Cyano-3,4-dihydro-2,2-bis(methoxymethyl)-4-(3-pyridylamino)-2H-1-benzopyran-3-ol obtained in Example 43 was treated in the same manner as in Example 81 to give (+)-3-[(3S,4R)-6-cyano-3,4-dihydro-2,2-bis(methoxymethyl)-3-hydroxy- 2H-1-benzopyran-4-ylamino]-pyridine-N-oxide.

EXAMPLE 83

By treating in the same manner as in Example 4, (−)-(3S,4R)-6-cyano-3,4-dihydro-4-(1,2-dihydro-1-oxoisoquinolin-2-yl)-2,2-bis(methoxymethyl)-2H-1-benzopyran-3-ol was obtained.

EXAMPLE 84

By treating in the same manner as in Example 4, (+)-(3S,4R)-6-cyano-3,4-dihydro-4-(2,3-dihydro-3-oxoisoquinolin-2-yl)-2,2-bis(methoxymethyl)-2H-1-benzopyran-3-ol was obtained.

EXAMPLE 85

(3S,4S)-6-Cyano-3,4-epoxy-3,4-dihydro-2,2-bis(methoxymethyl)-2H-1-benzopyran obtained in Preparative Example 5 and 2,3-dihydro-2-methylphthalazine-1,4-dione described in Journal of the Chemical Society; Perkin Transactions I, 2820 (1972) and Journal of the Chemical Society, 1710 (1960) were treated in the same manner as in Example 34 to give (−)-(3S,4R)-6-cyano-3,4-dihydro-4-[(3,4-dihydro-3-methyl-4-oxophthaladin-1-yl)oxy]-2,2-bis(methoxymethyl)-2H-1-benzopyran-3-ol.

EXAMPLE 86

(3S,4S)-6-Cyano-3,4-epoxy-3,4-dihydro-2,2-bis(methoxymethyl)-2H-1-benzopyran obtained in Preparative Example 5 and 1,6-dihydro-3-hydroxy-1,4,5- trimethylpyridazin-6-one obtained in Preparative Example 24 were treated in the same manner as in Example 2 to give (−)-(3S,4R)-6-cyano-3,4-dihydro-4-[(1,6-dihydro-1,4,5-trimethyl-6-oxo-3-pyridazinyl)oxy]-2,2-bis(methoxymethyl)-2H-1-benzopyran-3-ol.

EXAMPLE 87

(3S,4S)-6-Bromo-3,4-epoxy-3,4-dihydro-2,2-bis(methoxymethyl)-2H-1-benzopyran obtained in Preparative Example 18 was treated in the same manner as in Example 2 to give (−)-(3S,4R)-6-bromo-3,4-dihydro-4-[(1,6-dihydro-1-methyl-6-oxo-3-pyridazinyl)oxy]-2,2-bis(methoxymethyl)-2H-1-benzopyran-3-ol.

EXAMPLE 88

(3S,4S)-3,4-Epoxy-3,4-dihydro-2,2-bis(methoxymethyl)-6-nitro-2H-1-benzopyran obtained in Preparative Example 10 and 1,6-dihydro-3-hydroxy-1-methylpyridazin-6-one were treated in the same manner as in Example 2 to give (−)-(3S,4R)-3,4-dihydro-4-[(1,6-dihydro-1-methyl-6-oxo-3-pyridazinyl)oxy]-2,2-bis(methoxymethyl)-6-nitro-2H-1-benzopyran-3-ol.

The properties of the compounds obtained in Examples 1 to 88 are shown in Tables 1 to 44.

TABLE 1

| Ex. No. | Structural formula | m.p. (rec. from soln.) | IR cm⁻¹ | ¹H NMR (δ) ppm | MS | [α]_D |
|---|---|---|---|---|---|---|
| 1 | | 157.5–158.5° C. (AcOEt) | 2220, 1658, 1574 KBr | CD₃OD 3.37(3H,s), 3.46(3H,s), 3.62(3H,s), 3.65–3.85(4H,m), 4.16(1H,d,J=9.0Hz), 4.36(1H,d,J=9.0Hz), 5.09(1H,t,J=9.0Hz), 6.80–7.00(3H,m), 7.46(1H,dd,9.0Hz,1.0Hz), 7.65(1H,dd,J=9.0Hz,1.0Hz). | 386 (M⁺) | −126° (c=0.49, MeOH) |
| 2 | | 137–138° C. (−) | 2222, 1580, 1658 KBr | DMSO-d₆ 3.24(3H,s),3.28(3H,s), 3.49(1H,d,J=10.3Hz), 3.55–3.65(2H,m),3.58(3H,s), 3.73(1H,d,J=10.3Hz), 4.20(1H,dd), 5.05(1H,d,J=6.0Hz), 6.06(1H,d,J=5.6Hz), 7.02(1H,d,J=9.8Hz), 7.04(1H,d,J=8.5Hz), 7.25(1H,d,J=9.8Hz), 7.69(1H,dd,J=8.5Hz,1.8Hz), 7.80(1H,d,J=1.8Hz). | 387 (M⁺) | −112.6° (c=1.0, MeOH) |

TABLE 2

| Ex. No. | Structural formula | m.p. (rec. from soln.) | IR cm⁻¹ | ¹H NMR (δ) ppm | MS | [α]_D |
|---|---|---|---|---|---|---|
| 3 | | 175.0–176.5° C. (AcOEt) | 2225 1674 film | CDCl₃ 3.31(3H,s), 3.46(3H,s), 3.74–3.89(4H,m), 4.48(1H,d), 5.38(1H,d), 6.99(1H,d), 7.44–7.49(3H,m), 7.57(1H,d), 7.75(1H,t), 7.98(1H,s), 8.27(1H,d). | 439 (M⁺) | −103.8° (c=0.50, MeOH) |

TABLE 2-continued

| Ex. No. | Structural formula | m.p. (rec. from soln.) | IR cm$^{-1}$ | $^1$H NMR ($\delta$) ppm | MS | $[\alpha]_D$ |
| --- | --- | --- | --- | --- | --- | --- |
| 4 | (structure with NC-indole, NC-chromanol, OMe groups) | non-crystalline solid | 2225 film | CDCl$_3$ 3.36(3H,s), 3.43(3H,s), 3.55–4.12(4H,m), 4.58(1H,br s), 6.34–8.00(8H,m). | 341 (M$^+$) | −6.9° (c=0.52, MeOH) |

TABLE 3

| Ex. No. | Structural formula | m.p. (rec. from soln.) | IR cm$^{-1}$ | $^1$H NMR ($\delta$) ppm | MS | $[\alpha]_D$ |
| --- | --- | --- | --- | --- | --- | --- |
| 5 | (Cl-pyridazinyl-NH-chromanol structure) | 197.0~200.0° C. (CH$_2$Cl$_2$-Hexane) | 2225 KBr | CDCl$_3$ 3.31(3H,s), 3.43(3H,s), 3.65–3.85(4H,m), 4.23(1H,d,J=9.4Hz), 4.71(1H,br,s), 5.48(1H,br t,J=9.0Hz), 5.61(1H,br d,J=8.1Hz) 6.87(1H,d,J=9.4Hz), 6.95(1H,d,J=8.5Hz) 7.22(1H,d,J=9.4Hz), 7.43(1H, dd,J=8.5Hz,2.0Hz), 7.59(1H,d,J=2.0Hz). | 390 (M$^+$) | −104.0° (c=0.50, MeOH) |
| 6 | (OHC-indole-chromanol structure) | 216.5~217.5° C. (EtOH) | 2220, 1642 KBr | DMSO-d$_6$ 3.31(3H,s), 3.33(3H,s), 3.50–4.00(4H,m), 4.55(1H,br s), 5.60–8.70(10H,m), 9.97(1H,br s). | 406 (M$^+$) | +30.6° (c=1.02, CHCl$_3$) |

TABLE 4

| Ex. No. | Structural formula | m.p. (rec. from soln.) | IR cm$^{-1}$ | $^1$H NMR ($\delta$) ppm | MS | $[\alpha]_D$ |
| --- | --- | --- | --- | --- | --- | --- |
| 7 | (OAc-pyridazinyl-NH-chromanol structure) | 117.5–120.0° C. (CH$_2$Cl$_2$-Hexane) | 2226, 1749 KBr | CDCl$_3$ 2.05(3H,s), 3.34(3H,s), 3.37(3H,s), 3.55–3.75(4H,m), 4.75(1H,d,J=8.8Hz), 5.24(1H,t,J=8.8Hz), 5.52(1H,d,J=8.8Hz), 6.82(1H,d,J=9.8Hz), 6.90(1H,d,J=9.8Hz), 6.98(1H,d,J=8.5Hz), 7.47(1H,dd,J=8.5 7.63(1H,d,J=2.0Hz). | 414 (M$^+$) | −10.2° (c=0.50, MeOH) |

TABLE 4-continued

| Ex. No. | Structural formula | m.p. (rec. from soln.) | IR cm$^{-1}$ | $^1$H NMR ($\delta$) ppm | MS | $[\alpha]_D$ |
|---|---|---|---|---|---|---|
| 8 | | 138.5~141.5° C. (CH$_2$Cl-Hexane) | 2225, 1673 KBr | CDCl$_3$ 3.24(3H,s), 3.25(3H,s), 3.50–3.95(9H,m), 4.50–4.80(2H,m), 5.55(1H,br d,J=6.0Hz), 5.96(1H,br,s), 6.68(1H,d,J=9.8Hz), 6.90(1H,d,J=8.5Hz), 6.97(1H,d,J=9.8Hz), 7.39(1H,dd,J=8.5,2.0Hz), 7.61(1 J=2.0Hz). | 372 (M$^+$) | −118.0° (c=0.50, MeOH) |

TABLE 5

| Ex. No. | Structural formula | m.p. (rec. from soln.) | IR cm$^{-1}$ | $^1$H NMR ($\delta$) ppm | MS | $[\alpha]_D$ |
|---|---|---|---|---|---|---|
| 9 | | non-crystalline solid | 2224, 1621, 1492, 1315 KBr | DMSO-d$_6$ 3.31(3H,s), 3.33(3H,s), 3.50–4.00(4H,m), 4.50(1H,br s), 5.50–8.60(11H,m). | 449 (M$^+$) | −55.2° (c=0.54, MeOH) |
| 10 | | non-crystalline solid | 2226, 1612 KBr | DMSO-d$_6$(100° C.) 3.27(3H,s), 3.37(3H,s), 3.60–3.95(4H,m), 4.53(1H,dd,J=9.9,6.2Hz), 5.65(1H,d,J=6.2Hz), 5.73(1H,d,J=9.9Hz), 6.78(1H,s), 7.05–7.20(4H,m), 7.55–7.65(2H,m), 8.00–8.10(1H,m), 8.28(1H,s), 10.28(1H,s). | 421 (M$^+$) | −6.1° (c=1.01, MeOH) |

TABLE 6

| Ex. No. | Structural formula | m.p. (rec. from soln.) | IR cm$^{-1}$ | $^1$H NMR ($\delta$) ppm | MS | $[\alpha]_D$ |
|---|---|---|---|---|---|---|
| 11 | | non-crystalline solid | 2227, 1610 KBr | DMSO-d$_6$(100° C.) 3.27(3H,s), 3.37(3H,s), 3.60–3.95(4H,m), 4.54(1H,dd,J=9.9,6.2Hz), 5.67(1H,d,J=6.2Hz), 5.78(1H,d,J=9.9Hz), 6.77(1H,s), 7.00–7.25(4H,m), 7.55–7.65(1H,m), 7.77(1H,s), 7.85–7.95(1H,m), 8.22(1H,br s), 10.98(1H,br s). | 421 (M$^+$) | −3.7° (c=1.01, MeOH) |

TABLE 6-continued

| Ex. No. | Structural formula | m.p. (rec. from soln.) | IR cm$^{-1}$ | $^1$H NMR ($\delta$) ppm | MS | $[\alpha]_D$ |
|---|---|---|---|---|---|---|
| 12 | (structure: chroman with CN, OH, CH₂OCH₃ groups and pyrazole-COOCH₃) | non-crystalline solid | 2226.5, 1718.1 KBr | CDCl₃ 3.32(3H,s), 3.45(3H,s), 3.6–4.0(4H,m), 3.85(3H,s), 4.65(1H,d), 5.56(1H,d), 6.88(1H,s), 6.99(1H,d), 7.46(1H,dd), 8.01(1H,s), 8.13(1H,s). | 387 (M⁺) | −33.0° (c=MeOH) |

TABLE 7

| Ex. No. | Structural formula | m.p. (rec. from soln.) | IR cm$^{-1}$ | $^1$H NMR ($\delta$) ppm | MS | $[\alpha]_D$ |
|---|---|---|---|---|---|---|
| 13 | (structure: chroman with CN, OH, CH₂OCH₃ groups and N-ethyl pyridazinone-NH) | non-crystalline solid | 2224, 1662 KBr | CDCl₃ 1.26(3H,t,J=7.2Hz), 3.35(3H,s), 3.46(3H,s), 3.65–3.85(4H,m), 3.99(2H,q,J=7.2Hz), 4.23(1H,d,J=9.4Hz), 4.70(1H,br s), 5.05(1H,br t,J=8.3Hz), 6.84(2H,s), 6.95(1H,d,J=8.5Hz), 7.44(1H,dd,J=8.5,2.0 Hz), 7.65(1H,d,J=2.0Hz). | 400 (M⁺) | −109.6° (c=0.95, MeOH) |
| 14 | (structure: chroman with CN, OH, CH₂OCH₃ groups and N-isopropyl pyridazinone-NH) | non-crystalline solid | 2224, 1662 KBr | CDCl₃ 1.04(3H,d,J=6.6Hz), 1.22(3H,d,J=6.6Hz), 3.34(3H,s), 3.45(3H,s), 3.65–3.85(4H,m), 4.36(1H,d,J=9.6Hz), 4.83(1H,br d,J=6.9Hz), 4.99(1H,br t,J=7.2Hz), 5.12(1H,septet,J=6.6Hz), 6.81(2H,s), 6.96 (1H,d,J=), 7.43(1H,dd,J=8.5,1.8Hz), 7.65(1H,d,J=1.8Hz). | 414 (M⁺) | −57.6° (c=1.02, MeOH) |

TABLE 8

| Ex. No. | Structural formula | m.p. (rec. from soln.) | IR cm$^{-1}$ | $^1$H NMR ($\delta$) ppm | MS | $[\alpha]_D$ |
|---|---|---|---|---|---|---|
| 15 | (structure: chroman with CN, OH, CH₂OCH₃ groups and CN-indole) | non-crystalline solid | 2224 KBr | CDCl₃ 3.38(3H,s), 3.43(3H,s), 3.65–4.00(4H,m), 4.51(1H,br s), 5.40–8.00(9H,m). | 403 (M⁺) | −0.5° (c=0.98, MeOH) |

TABLE 8-continued

| Ex. No. | Structural formula | m.p. (rec. from soln.) | IR cm⁻¹ | ¹H NMR (δ) ppm | MS | [α]_D |
|---|---|---|---|---|---|---|
| 16 | (structure) | non-crystalline solid | 2228, 1625 KBr | CDCl₃ 3.42(6H,s), 3.58(4H,s), 5.39(1H,d), 6.24(1H,br s), 6.92(1H,d), 7.45–7.53(3H,m), 8.29(1H,s), 11.06(1H,br s). | 357 (M⁺) | +3.02° (c=0.43, MeOH) |

TABLE 9

| Ex. No. | Structural formula | m.p. (rec. from soln.) | IR cm⁻¹ | ¹H NMR (δ) ppm | MS | [α]_D |
|---|---|---|---|---|---|---|
| 17 | (structure) | oily substance | 2225 film | CDC₃ 3.34(6H,s), 3.39(4H,s), 4.42(1H,d), 5.31(1H,d), 6.98–7.10(4H,m), 7.32–7.37(2H,m), 7.48(1H,d), 7.64(1H,s). | 355 (M⁺) | −58.6° (c=0.5, MeOH) |
| 18 | (structure) | 244.5–246° C. (EtOH-H₂O) | 2222, 1568 KBr | DMSO-d₆ 3.23(3H,s), 3.28(3H,s), 3.43(3H,s), 3.49–3.70(4H,m), 4.09(1H,dd), 4.83(1H,t), 5.67(1H,d), 6.74–6.83(2H,m), 6.92–7.04(2H,m), 7.55–7.62(2H,m). | 386 (M⁺) | 0° (c=0.45, MeOH) |

TABLE 10

| Ex. No. | Structural formula | m.p. (rec. from soln.) | IR cm⁻¹ | ¹H NMR (δ) ppm | MS | [α]_D |
|---|---|---|---|---|---|---|
| 19 | (structure) | non-crystalline solid | 2224 film | CDCl₃ 3.37(3H,s), 3.42(3H,s), 3.58–3.92(4H,m), 4.23(1H,d), 4.78–4.94(2H,m), 6.71–6.89(2H,m), 6.98(1H,d), 7.35–7.54(3H,m), 7.59(1H,s). | 379 (M⁺) | +32.4° (c=0.51, MeOH) |

TABLE 10-continued

| Ex. No. | Structural formula | m.p. (rec. from soln.) | IR cm$^{-1}$ | $^1$H NMR (δ) ppm | MS | $[α]_D$ |
|---|---|---|---|---|---|---|
| 20 | (structure with CN-phenyl-NH, NC-chromanol, OH, CH$_2$OCH$_3$ groups) | non-crystalline solid | 2222 KBr | CDCl$_3$ 3.37(3H,s), 3.42(3H,s), 3.50(1H,d), 3.60–3.88(4H,m), 4.17(1H,dd), 4.56(1H,d), 4.80(1H,t), 6.72(2H,d), 6.96(1H,d), 7.41–7.54(3H,m), 7.57(1H,s). | 379 (M$^+$) | −105.6° (c=0.99, MeOH) |

TABLE 11

| Ex. No. | Structural formula | m.p. (rec. from soln.) | IR cm$^{-1}$ | $^1$H NMR (δ) ppm | MS | $[α]_D$ |
|---|---|---|---|---|---|---|
| 21 | (pyrimidinyl-NH-chromanol structure) | non-crystalline solid | 2225 KBr | CDCl$_3$ 3.32(3H,s), 3.45(3H,s), 3.68–3.87(4H,m), 4.21(1H,d), 5.38(1H,t), 5.74(1H,d), 6.66(1H,t), 6.98(1H,d), 7.46(1H,d), 7.66(1H,s), 8.27(2H,d). | 356 (M$^+$) | −4.2° (c=0.64, CHCl$_3$) |
| 22 | (4-pyridone-N-chromanol structure) | non-crystalline solid | 2226, 1639 KBr | CDCl$_3$(60° C.) 3.25(3H,s), 3.49(3H,s), 3.60(1H,d), 3.74(1H,s), 4.02(1H,d), 4.28(1H,d), 5.20(1H,d), 6.20(2H,d), 6.99(1H,s), 7.02(1H,d), 7.29(2H,br d), 7.46(1H,d). | 356 (M$^+$) | +52.9° (c=0.24, MeOH) |

TABLE 12

| Ex. No. | Structural formula | m.p. (rec. from soln.) | IR cm$^{-1}$ | $^1$H NMR (δ) ppm | MS | $[α]_D$ |
|---|---|---|---|---|---|---|
| 23 | (NH$_2$-pyrimidinone-N-chromanol structure) | non-crystalline solid | 2226, 1651 KBr | DMSO-d$_6$(90° C.) 3.19(3H,s), 3.36(3H,s), 3.58(1H,d), 3.63(2H,s) 3.73(1H,d), 4.45(1H,br d), 5.53(1H,br s), 5.79(1H,d), 6.64(2H,br s), 6.97(1H,d), 7.06(1H,t), 7.35(1H,d), 7.51(1H,dd). | 372 (M$^+$) | −37.2° (c=0.50, MeOH) |

TABLE 12-continued

| Ex. No. | Structural formula | m.p. (rec. from soln.) | IR cm⁻¹ | ¹H NMR (δ) ppm | MS | [α]$_D$ |
|---|---|---|---|---|---|---|
| 24 | (4-nitrophenoxy group at chroman C-4; NC on aromatic ring; OH at C-3; 2,2-bis(methoxymethyl) chroman) | non-crystalline solid | 2227.6, 1590.8, 1343.1, 1252.7 KBr | CDCl$_3$ 3.33(3H,s), 3.42(3H,s), 3.61(2H,s), 3.76(1H,d), 3.9–4.1(2H,m), 4.48(1H,d), 5.50(1H,d), 7.01(1H,d), 7.19(2H,d), 7.54(1H,d), 7.58(1H,s), 8.27(2H,d). | 400 (M⁺) | −62.4° (c=1.12, MeOH) |

TABLE 13

| Ex. No. | Structural formula | m.p. (rec. from soln.) | IR cm⁻¹ | ¹H NMR (δ) ppm | MS | [α]$_D$ |
|---|---|---|---|---|---|---|
| 25 | (1H-1,2,4-triazol-3-ylthio substituent) | non-crystalline solid | 3434, 2224 KBr | CDCl$_3$ 3.27(3H,s), 3.48(3H,s), 3.66–3.84(4H,m), 4.48(1H,d), 4.73(1H,d), 6.96(1H,d), 7.45(1H,dd), 8.03(1H,s), 8.15(1H,s). | 362 (M⁺) | +28.3° (c=0.94, MeOH) |
| 26 | (1-methylimidazol-2-ylthio substituent) | non-crystalline solid film | 2224 | CDCl$_3$ 3.19(3H,s), 3.48(3H,s), 3.73(3H,s), 3.62–3.83(4H,m), 4.51(3H,d), 4.62(1H,d), 6.96(1H,d), 7.00(1H,d), 7.02(1H,d), 7.46(1H,dd), 7.99(1H,d). | 375 (M⁺) | +3.0° (c=1.05, MeOH) |

TABLE 14

| Ex. No. | Structural formula | m.p. (rec. from soln.) | IR cm⁻¹ | ¹H NMR (δ) ppm | MS | [α]$_D$ |
|---|---|---|---|---|---|---|
| 27 | (3-amino-1,2,4-triazol-1-yl substituent) | non-crystalline solid | 2226.2 KBr | CDCl$_3$ 3.28(3H,s), 3.45(3H,s), 3.57(1H,d), 3.65(1H,d), 3.80(1H,d), 3.89(1H,d), 4.26(2H,s), 4.54(2H,d), 5.35(2H,d), 5.56(1H,br s), 7.05(1H,s), 7.44(1H,d), 7.90(1H,s). | 345 (M⁺) | +20.0° (c=0.20, MeOH) |

TABLE 14-continued

| Ex. No. | Structural formula | m.p. (rec. from soln.) | IR cm$^{-1}$ | $^1$H NMR ($\delta$) ppm | MS | $[\alpha]_D$ |
|---|---|---|---|---|---|---|
| 28 | (structure) ·1/2H$_2$O | 160.0~161.0° C. (EtOH-H$_2$O) | 2221, 1655, 1572 KBr | CD$_3$OD 3.32(3H,s), 3.38(3H,s), 3.59(3H,s), 3.64(1H,d,J=10.7Hz), 3.65(1H,d,J=10.6Hz), 3.73(1H,d,J=10.7Hz), 3.79(1H,d,J=10.6Hz), 4.25(1H,d,J=8.5Hz), 5.05(1H,d,J=8.5Hz), 6.84(1H,d,J=9.6Hz), 6.95(1H,d,J=8.5Hz), 7.09(1H,d,J=9.6Hz), 7.49(1H,m,J=8.5Hz,2.0Hz, 0.6Hz), 7.59(1H,m,J=2.0Hz,1.0Hz). | 386 (M$^+$) | −126.6° (c=0.99, MeOH) |

TABLE 15

| Ex. No. | Structural formula | m.p. (rec. from soln.) | IR cm$^{-1}$ | $^1$H NMR ($\delta$) ppm | MS | $[\alpha]_D$ |
|---|---|---|---|---|---|---|
| 29 | (structure) | 159.0~160.0° C. (EtOH—H$_2$O) | 3354, 2221, 1576 KBr | DMSO-d$_6$ 3.22(3H, s), 3.27(3H, s), 3.42(3H, s), 3.50–3.68(4H, m), 4.08(1H, dd, J=8.1Hz, 5.5Hz), 4.82(1H, t, J=8.1Hz), 5.66(1H, d, J=5.5Hz), 6.74–6.84(2H, m), 6.92–7.04(2H, m), 7.54–7.62(2H, m). | 386 (M$^+$) | +127.3° (c=1.045, MeOH) |
| 30 | (structure) | non-crystalline solid | 3300, 2926, 2816, 1662 film | DMSO-d$_6$ 3.22(3H, s), 3.26(3H, s), 3.44(3H, s), 3.49–3.64(4H, m), 4.05(1H, dd, J=4.5Hz, 9.0Hz), 4.73(1H, t, J=15.0Hz), 5.48(1H, d, J=6.0Hz), 6.75–6.82(3H, m), 6.93–7.01(3H, m). | 380 (M$^+$) | |

TABLE 16

| Ex. No. | Structural formula | m.p. (rec. from soln.) | IR cm⁻¹ | ¹H NMR (δ) ppm | MS | [α]$_D$ |
|---|---|---|---|---|---|---|
| 31 | (structure: 6-bromo chroman with OH, CH$_2$OCH$_3$ groups, NH linked to 2-methyl-3(2H)-pyridazinone) | non-crystalline solid | 3342, 2928, 1579 KBr | CDCl$_3$ 3.36(3H, s), 3.42(3H, s), 3.58(3H, s), 3.68 (1H, d, J=11.0Hz), 3.72(1H, d, J=10.6Hz), 3.76(1H, d, J=10.6Hz), 3.84(1H, d, J=10.6Hz), 4.14(1H, dd, J=8.8Hz, 5.1Hz), 4.37(1H, d, J= 5.5Hz), 4.88(1H, d, J=8.1Hz), 5.03(1H, t, J= 8.4Hz), 6.76–6.88(3H, m), 7.26(1H, dd, J= 8.4Hz, 2.2Hz), 7.40(1H, d, J=2.2Hz). | 339 (M⁺) 441 (M⁺) | −86.2° (c=1.02, MeOH) |
| 32 | (structure: 6-nitro chroman with OH, CH$_2$OCH$_3$ groups, NH linked to 6-chloropyridazine) | non-crystalline solid | 3300, 2928, 1586, 1516, 1446 film | CDCl$_3$ 3.31(3H, s), 3.44(3H, s), 3.69–3.85(4H, m), 4.25(1H, d, J=12.0Hz), 4.69(1H, br s), 5.31 (1H, d, J=9.0Hz), 5.59(1H, t, J=9.0Hz), 6.90 (1H, d, J=9.0Hz), 6.99(1H, d, J=9.0Hz), 7.24– 7.26(1H, m), 8.04–8.08(1H, dd, J=3.0Hz, 9.0Hz), 8.20–8.21(1H, m). | 411 (M⁺) | |

TABLE 17

| Ex. No. | Structural formula | m.p. (rec. from soln.) | IR cm⁻¹ | ¹H NMR (δ) ppm | MS | [α]$_D$ |
|---|---|---|---|---|---|---|
| 33 | (structure: 6-cyano chroman with OH, CH$_2$OCH$_3$ groups, N-linked to 6-amino-3(2H)-pyridazinone) | 186–189° C. (CHCl$_3$-n-Hexane) | 3353, 2932, 2225, 1611, 1560 KBr | DMSO-d$_6$ 3.18(3H, s), 3.34(3H, s), 3.53–3.73(4H, m), 4.53–4.60(1H, m), 5.75(1H, d, J=6.0Hz), 5.86 (2H, s), 6.08(1H, br s), 6.84(1H, d, J=10.0Hz), 6.94–6.99(3H, m), 7.56(1H, dd, J=8.5Hz, 1.5Hz). | 372 (M⁺) | −51.5° (c=1.31, MeOH) |
| 34 | (structure: 6-cyano chroman with OH, CH$_2$OCH$_3$ groups, NH linked to pyridazinone fused with morpholine-like ring with N-methyl) | non-crystalline solid | 2222, 1640, 1590 film | DMSO-d$_6$ 2.68(3H, s), 3.01(2H, m), 3.22(3H, s), 3.32 (3H, s), 3.40(3H, s), 3.56–3.67(4H, m), 4.12– 4.28(3H, m), 5.02(1H, t, J=8.7Hz), 5.58(1H, d, J=6.0Hz), 6.94(1H, d, J=8.4Hz), 7.48–7.57 (2H, m). | 457 (M⁺) | −90.5° (c= 0.864, MeOH) |

TABLE 18

| Ex. No. | Structural formula | m.p. (rec. from soln.) | IR cm$^{-1}$ | $^1$H NMR (δ) ppm | MS | [α]$_D$ |
|---|---|---|---|---|---|---|
| 35 | | non-crystalline solid | 2223, 1631, 1594, 1520 film | DMSO-d$_6$ 3.02(3H, s), 3.12–3.15(2H, m), 3.20(3H, s), 3.29(3H, s), 3.38(3H, s), 3.53–3.65(4H, m), 4.12–4.21(3H, m), 4.95(1H, t, J=9.0Hz), 5.58 (1H, d, J=6.0Hz), 6.10(1H, d, J=9.0Hz), 6.93 (1H, d, J=9.0Hz), 7.47–7.59(2H, m). | 457 (M$^+$) | −65.5° (c=0.86, MeOH) |
| 36 | | non-crystalline solid | 2223, 1611, 1568 film | DMSO-d$_6$ 2.56(3H, s), 2.77–2.81(2H, m), 3.04–3.07(2H, m), 3.20(3H, s), 3.21(3H, s), 3.30(3H, s), 3.38 (3H, s), 3.54–3.65(4H, m), 4.19–4.24(1H, m), 4.94(1H, t, J=6.0Hz), 5.58(1H, d, J=6.0Hz), 5.73(1H, d, J=6.0Hz), 6.93(1H, d, J=6.0Hz), 7.47–7.56(2H, m). | 470 (M$^+$) | −79.5° (c=0.38, MeOH) |

TABLE 19

| Ex. No. | Structural formula | m.p. (rec. from soln.) | IR cm$^{-1}$ | $^1$H NMR (δ) ppm | MS | [α]$_D$ |
|---|---|---|---|---|---|---|
| 37 | | non-crystalline solid | 2223, 1636, 1577 KBr | CDCl$_3$ 3.78(3H, s), 3.47(3H, s), 3.70(3H, s), 3.75–3.86(4H, m), 4.31(1H, m), 4.43(1H, d, J= 3.5Hz), 4.96(1H, d, J=6.0Hz), 5.37(1H, m), 6.98(1H, d, J=6.4Hz), 7.46(1H, d, J=6.4Hz), 7.60–7.85(4H, m), 8.45–8.55(1H, m). | 436 (M$^+$) | −63.1° (c=1.08, MeOH) |
| 38 | | non-crystalline solid | 3445, 2927, 2224, 1490 KBr | DMSO-d$_6$ 3.22(3H, s), 3.27(3H, s), 3.50–3.69(4H, m), 3.88(3H, s), 4.09(1H, dd, J=9.0Hz, 6.0Hz), 4.94(1H, t, J=9.0Hz), 5.76(1H, d, J=6.0Hz), 6.80(1H, d, J=9.0Hz), 6.97(1H, d, J=9.0Hz), 7.35(1H, d, J=6.0Hz), 7.46(1H, d, J=9.0Hz), 7.58–7.61 (2H, m). | 402 (M$^+$) | −101.9° (c=0.64, MeOH) |

TABLE 20

| Ex. No. | Structural formula | m.p. (rec. from soln.) | IR cm⁻¹ | ¹H NMR (δ) ppm | MS | [α]$_D$ |
|---|---|---|---|---|---|---|
| 39 | (structure: chromane with O$_2$N-phenyl, OH, CH$_2$OCH$_3$ groups, NH linked to N-methyl-pyridazinone) | non-crystalline solid | 3300, 2954, 1573, 1514, 1430 CHCl$_3$ | CDCl$_3$ 3.36(3H, s), 3.45(3H, s), 3.56(3H, s), 3.71–3.83(4H, m), 4.25(1H, br s), 4.60(1H, br s), 5.11(1H, br s), 6.80–6.98(3H, m), 8.03 (1H, dd, J=8.5Hz, 2.1Hz), 8.22(1H, d, J= 2.1Hz). | 406 (M⁺) | +1.25° (c=0.16, CHCl$_3$) |
| 40 | (structure: chromane with F-phenyl, OH, CH$_2$OCH$_3$ groups, NH linked to 6-chloropyridazine) | non-crystalline solid | 3300, 2927, 1692, 1600, 1489 film | CDCl$_3$ 3.34(3H, s), 3.44(3H, s), 3.69–3.83(4H, m), 4.18(1H, d, J=9.3Hz), 4.35(1H, br s), 5.21(1H, d, J=8.2Hz), 5.40(1H, d, J=8.7Hz), 6.79–6.88 (3H, m), 6.96–7.00(1H, m), 7.20(1H, d, J= 9.3Hz). | 383 (M⁺) | |

TABLE 21

| Ex. No. | Structural formula | m.p. (rec. from soln.) | IR cm⁻¹ | ¹H NMR (δ) ppm | MS | [α]$_D$ |
|---|---|---|---|---|---|---|
| 41 | (structure: chromane with F-phenyl, OH, CH$_2$OCH$_3$ groups, NH linked to N-methyl-phthalazinone) | 125.5–127.5° C. (Et$_2$O) | 3346, 2927, 2815, 1633 film | DMSO-d$_6$ 3.23(3H, s), 3.31(3H, s), 3.55(3H, s), 3.57– 3.69(4H, m), 4.30(1H, dd, J=6.0Hz, 9.0Hz), 5.14(1H, t, J=9.0Hz), 5.50(1H, d, J=6.0Hz), 6.79–6.84(1H, m), 6.93–6.98(2H, m), 7.05 (1H, d, J=9.0Hz), 7.80–7.89(2H, m), 8.25– 8.27(2H, m). | 430 (M⁺) | |
| 42 | (structure: chromane with NC-phenyl, OH, CH$_2$OCH$_3$ groups, NH linked to 2-pyridyl) | non-crystalline solid | 2228, 1610 KBr | CDCl$_3$ 3.30(3H, s), 3.47(3H, s), 3.70–3.90(4H, m), 4.18(1H, d, J=9.2Hz), 4.66(1H, d, J=7.3Hz), 5.28(1H, dd, J=7.3Hz, 9.2Hz), 6.60(1H, d, J= 8.4Hz), 6.65–6.75(1H, m), 7.00(1H, d, J=8.4 Hz), 7.40–7.60(2H, m), 7.69(1H, s), 8.05(1H, d, J=3.7Hz). | 355 (M⁺) | −73.2° (c=0.97, MeOH) |

TABLE 22

| Ex. No. | Structural formula | m.p. (rec. from soln.) | IR cm$^{-1}$ | $^1$H NMR ($\delta$) ppm | MS | [$\alpha$]$_D$ |
|---|---|---|---|---|---|---|
| 43 | (structure: 6-cyano-chroman with 3-OH, 4-NH-(pyridin-3-yl), 2,2-bis(methoxymethyl)) | non-crystalline solid | 2223 KBr | CDCl$_3$<br>3.35(3H, s), 3.44(3H, s), 3.68(1H, d, J=8.1Hz), 3.71(1H, d, J=8.1Hz), 3.79(1H, d, J=7.9Hz), 3.83(1H, d, J=7.9Hz), 4.15–4.25(2H, m), 4.65–4.75(1H, m), 6.85–6.92(1H, m), 6.97(1H, d, J=6.4Hz), 7.00–7.08(1H, m), 7.45(1H, d, J=6.4 Hz), 7.63(1H, s), 7.90–7.98(2H, m). | 355 (M$^+$) | −26.2° (c=0.37, MeOH) |
| 44 | (structure: 6-cyano-chroman with 3-OH, 4-NH-(pyridin-3-yl), 2,2-bis(methoxymethyl)) | 195.8~197.9° C. (MeOH) | 2223, 1606 KBr | DMSO-d$_6$<br>3.24(3H, s), 3.28(3H, s), 3.53(1H, d, J=8.0 Hz), 3.56(1H, d, J=8.0Hz), 3.63(1H, d, J=8.0 Hz), 3.74(1H, d, J=8.0Hz), 4.01(1H, dd, J=3.7Hz, 5.9Hz), 4.67(1H, dd, J=5.9Hz, 6.2Hz), 5.80(1H, d, J=3.7Hz), 6.62(1H, d, J=4.5Hz), 6.85(1H, d, J=6.2Hz), 6.99(1H, d, J=6.5Hz), 7.49(1H, d, J=1.5Hz), 7.61(1H, dd, J=1.5Hz, 6.5Hz), 8.06(1H, d, J=4.5Hz). | 355 (M$^+$) | −64.7° (c=0.38, MeOH) |

TABLE 23

| Ex. No. | Structural formula | m.p. (rec. from soln.) | IR cm$^{-1}$ | $^1$H NMR ($\delta$) ppm | MS | [$\alpha$]$_D$ |
|---|---|---|---|---|---|---|
| 45 | (structure: 6-fluoro-chroman with 3-OH, 4-NH-(6-oxo-1,6-dihydropyridazin-3-yl), 2,2-bis(methoxymethyl)) | non-crystalline solid | 3280, 2932, 1674, 1592, 1567 film | CDCl$_3$<br>3.30(3H, s), 3.34(3H, s), 3.67–3.88(4H, m), 4.25(1H, d, J=7.5Hz), 4.42(1H, br, s), 4.69 (1H, d, J=8.0Hz), 4.87(1H, t, J=8.0Hz), 6.79–6.90(4H, m), 6.96–7.01(1H, m), 10.31(1H, br s). | 365 (M$^+$) | |
| 46 | (structure: 6-cyano-chroman with 3-OH, 4-NH-(1-methyl-2-oxo-1,2-dihydropyridin-5-yl), 2,2-bis(methoxymethyl)) | non-crystalline solid | 3316, 2925, 2224, 1668, 1568 film | DMSO-d$_6$<br>3.23(3H, s), 3.25(3H, s), 3.37(3H, s), 3.50–3.68(4H, m), 3.95(1H, d, J=6.0Hz), 4.18(1H, d, J=6.0Hz), 6.36(1H, d, J=9.0Hz), 6.97(1H, d, J=9.0Hz), 7.00(1H, d, J=3.0Hz), 7.20(1H, dd, J=3.0Hz, 9.0Hz), 7.58–7.66(2H, m). | 385 (M$^+$) | |

TABLE 24

| Ex. No. | Structural formula | m.p. (rec. from soln.) | IR cm⁻¹ | ¹H NMR (δ) ppm | MS | $[\alpha]_D$ |
|---|---|---|---|---|---|---|
| 47 | | non-crystalline solid | 2224, 1666, 1606, 1551 film | DMSO-$d_6$ 3.20(3H, s), 3.25(3H, s), 3.49–3.69(4H, m), 3.97(1H, d, J=9.0Hz), 4.20(1H, t, J=6.0Hz), 5.30(1H, d, J=9.0Hz), 6.29(1H, d, J=9.0Hz), 6.72(1H, d, J=3.0Hz), 6.96(1H, d, J=9.0Hz), 7.19(1H, dd, J=9.0Hz, 3.0Hz), 7.58–7.65(2H, m). | 371 (M⁺) | |
| 48 | | non-crystalline solid | 3318, 2933, 2224, 1661 film | DMSO-$d_6$ 0.75(3H, t, J=7.5Hz), 1.49–1.61(2H, m), 3.20 (3H, s), 3.28(3H, s), 3.51–3.66(4H, m), 3.73 (2H, t, J=7.5Hz), 4.22(1H, dd, J=6.0Hz, 6.0Hz), 4.73(1H, t, J=6.0Hz), 5.64(1H, d, J= 6.0Hz), 6.76(1H, d, J=9.0Hz), 6.86(1H, d, J= 6.0Hz), 6.94–7.01 (2H, m), 7.55–7.58(2H, m). | 415 (M⁺) | −112.8° (c=0.83, MeOH) |

TABLE 25

| Ex. No. | Structural formula | m.p. (rec. from soln.) | IR cm⁻¹ | ¹H NMR (δ) ppm | MS | $[\alpha]_D$ |
|---|---|---|---|---|---|---|
| 49 | | non-crystalline solid | 3316, 3009, 2931, 2224, 1660 film | DMSO-$d_6$ 0.18–0.42(4H, m), 1.04–1.15(1H, m), 3.20(3H, s), 3.29(3H, s), 3.53–3.72(6H, m), 4.23(1H, dd, J=5.6Hz, 5.5Hz), 4.76(1H, t, J= 7.8Hz), 5.62(1H, d, J=5.5Hz), 6.77(1H, d, J= 9.7Hz), 6.85(1H, d, J=7.2Hz), 6.94–7.03(2H, m), 7.55–7.59(2H, m). | 427 (M⁺) | −99.4° (c=0.66, MeOH) |
| 50 | | non-crystalline solid | 2223, 1664, 1578 KBr | CDCl₃ 3.34(3H, s), 3.35(3H, s), 3.45(3H, s), 3.62– 3.90(6H, m), 4.05–4.30(3H, m), 4.50–4.70 (1H, m), 5.00–5.10(1H, m), 6.87(2H, s), 6.96 (1H, d, J=8.4Hz), 7.45(1H, d, J=8.4Hz), 7.67 (1H, s). | 430 (M⁺) | −110.1° (c=0.82, MeOH) |

TABLE 26

| Ex. No. | Structural formula | m.p. (rec. from soln.) | IR cm⁻¹ | ¹H NMR (δ) ppm | MS | [α]_D |
|---|---|---|---|---|---|---|
| 51 | (structure) | non-crystalline solid | 2224, 1663, 1577 KBr | CDCl₃ 0.75–0.95(3H, m), 1.15–1.40(10H, m), 3.34 (3H, s), 3.44(3H, s), 3.65–4.00(8H, m), 4.18–4.25(1H, m), 4.50–4.70(1H, m), 5.00–5.10(1, m), 6.84(2H, s), 6.93(1H, d, J=8.5Hz), 7.43 (1H, d, J=8.5Hz), 7.64(1H, s). | 470 (M⁺) | −103.1° (c=0.48, MeOH) |
| 52 | (structure) | non-crystalline solid | 2224, 1664, 1578 KBr | CDCl₃ 3.35(3H, s), 3.46(3H, s), 3.65–3.85(4H, m), 4.03–4.04(1H, m), 4.16–4.24(1H, m), 4.53–4.70(3H, m), 5.00–5.24(3H, m), 5.80–5.95(1H, m), 6.86(2H, s), 6.95(1H, d, J=9.0Hz), 7.45 (1H, d, J=9.0Hz), 7.66(1H, s). | 412 (M⁺) | −131.3° (c=0.77, MeOH) |

TABLE 27

| Ex. No. | Structural formula | m.p. (rec. from soln.) | IR cm⁻¹ | ¹H NMR (δ) ppm | MS | [α]_D |
|---|---|---|---|---|---|---|
| 53 | (structure) | non-crystalline solid | 3378, 2928, 2225, 1752, 1670, 1582, 1511 KBr | DMSO-d₆ 3.20(3H, s), 3.27(3H, s), 3.51–3.65(4H, m), 3.65(3H, s), 4.07(1H, dd, J=9.0Hz, 6.0Hz), 4.50–4.69(2H, m), 4.76(1H, t, J=9.0Hz), 5.67 (1H, d, J=6.0Hz), 6.84(1H, d, J=9.0Hz), 6.92–6.96(2H, m), 7.07(1H, d, J=12.0Hz), 7.56–7.59 (2H, m). | 444 (M⁺) | −127° (c=0.80, MeOH) |
| 54 | (structure) | 164–169° C. (CHCl₃-n-Hexane) | 3374, 2926, 2223, 1611, 1518 KBr | DMSO-d₆ 3.20(3H, s), 3.26(3H, s), 3.52–3.69(4H, m), 4.21–4.25(1H, m), 4.93(1H, t, J=9.0Hz), 5.76 (1H, t, J=6.0Hz), 6.95–7.00(2H, m), 7.18(1H, d, J=6.0Hz), 7.29(1H, d, J=9.0Hz), 7.59(1H, d, J=6.0Hz), 7.68(1H, br s), 8.00(2H, d, J=9.0 Hz), 8.23(2H, d, J=9.0Hz). | 493 (M⁺) | −83.1° (c=0.85, MeOH) |

TABLE 28

| Ex. No. | Structural formula | m.p. (rec. from soln.) | IR cm$^{-1}$ | $^1$H NMR (δ) ppm | MS | [α]$_D$ |
|---|---|---|---|---|---|---|
| 55 | | 165–171° C. (CHCl$_3$-n-Hexane) | 3422, 2926, 2224, 1610, 1534 KBr | DMSO-d$_6$ 3.16(3H, s), 3.28(3H, s), 3.50–3.64(4H, m), 4.13(1H, dd, J=5.5Hz, 9.0Hz), 4.82(1H, t, J=9.0Hz), 5.70(1H, d, J=5.5Hz), 6.90–6.96(2H, m), 7.14(1H, d, J=8.0Hz), 7.19(1H, d, J=10.0 Hz), 7.57–7.62(4H, m),7.77–7.82(1H, m), 7.98(1H, dd, J=8.0Hz, 1.2Hz). | 493 (M$^+$) | −174.5° (c=0.98, MeOH) |
| 56 | | non-crystalline solid | | DMSO-d$_6$ 3.19(3H, s), 3.26(3H, s), 3.51–3.64(4H, m), 4.05–4.10(1H, m), 4.56–4.61(3H, m), 5.11–5.20(2H, m), 5.67(1H, d, J=6.0Hz), 6.85(1H, d, J=9.0Hz), 6.92–6.97(2H, m), 7.08(1H, d, J=9.0Hz), 7.32–7.35(5H, m), 7.56–7.59(2H, m). | 520 (M$^+$) | |

TABLE 29

| Ex. No. | Structural formula | m.p. (rec. from soln.) | IR cm$^{-1}$ | $^1$H NMR (δ) ppm | MS | [α]$_D$ |
|---|---|---|---|---|---|---|
| 57 | | non-crystalline solid | 3342, 2927, 2223, 1663, 1577 KBr | DMSO-d$_6$ 1.99(3H, s), 2.64(2H, t, J=6.0Hz), 3.19(3H, s), 3.28(3H, s), 3.51–3.66(4H, m), 3.88–4.01(2H, m), 4.23(1H, dd, J=9.0Hz, 6.0Hz), 4.73(1H, t, J=9.0Hz), 5.67(1H, d, J=6.0Hz), 6.78(1H, d, J=9.0Hz), 6.92–6.96(2H, m), 7.01(1H, d, J=9.0Hz), 7.54–7.57(2H, m). | 446 (M$^+$) | −105.2° (c=0.56, MeOH) |
| 58 | | non-crystalline solid | 3448, 2224, 1578 KBr | DMSO-d$_6$ 2.11(6H, s), 2.37–2.50(2H, m), 3.19(3H, s), 3.28(3H, s), 3.51–3.66(4H, m), 3.82–3.88(2H, m), 4.20(1H, dd, J=9.0Hz, 6.0Hz), 4.75(1H, t, J=9.0Hz), 5.66(1H, d, J=6.0Hz), 6.75(1H, d, J=12.0Hz), 6.88(1H, d, J=6.0Hz), 6.94–6.97 (1H, m), 7.00(1H, d, J=9.0Hz), 7.55 –7.58(2H, m). | 443 (M$^+$) | |

TABLE 30

| Ex. No. | Structural formula | m.p. (rec. from soln.) | IR cm$^{-1}$ | $^1$H NMR (δ) ppm | MS | [α]$_D$ |
|---|---|---|---|---|---|---|
| 59 | | non-crystalline solid | 2362, 2225, 1670, 1589 film | DMSO-d$_6$ 3.22(3H, s), 3.27(3H, s), 3.51–3.67(4H, m), 4.05–4.10(1H, m), 4.83–4.99(3H, m), 5.70(1H, d, J=6.0Hz), 6.89(1H, d, J=9.0Hz), 6.97(1H, d, J=9.0Hz), 7.08–7.11(2H, m), 7.57–7.60(2H, m). | 411 (M$^+$) | −80.0° (c = 1.05, MeOH) |
| 60 | | non-crystalline solid | 3375, 2928, 2224, 1664, 1577 KBr | CDCl$_3$ 3.32(3H, s), 3.44(3H, s), 3.65–3.85(4H, m), 4.23(1H, dd, J=6.0Hz, 3.0Hz), 4.54(1H, br s), 4.76(1H, d, J=6.0Hz), 4.90–5.10(4H, m), 6.47(1H, d, J=9.0Hz), 6.68(1H, d, J=9.0Hz), 6.95(1H, d, J=9.0Hz), 7.25–7.38(6H, m), 7.41(1H, dd, J=8.5Hz, 3.0Hz), 7.54(1H, br s). | 426 (M$^+$) | −122.9° (c = 1.00, MeOH) |

TABLE 31

| Ex. No. | Structural formula | m.p. (rec. from soln.) | IR cm$^{-1}$ | $^1$H NMR (δ) ppm | MS | [α]$_D$ |
|---|---|---|---|---|---|---|
| 61 | | non-crystalline solid | 3315, 2922, 2223, 1661, 1608, 1574 film | CDCl$_3$ 1.65–1.74(3H, m), 3.34(3H, s), 3.46(3H, s), 3.70–3.82(4H, m), 4.21–4.23(2H, m), 4.22(1H, d, J=6.0Hz), 4.61–4.68(1H, m), 4.85–5.18(1H, m), 5.47–5.76(2H, m), 6.77–6.89(2H, m), 6.96(1H, d, J=9.0 Hz), 7.44(1H, d, J=9.0Hz), 7.66(1H, s). | 426 (M$^+$) | −134.5° (c = 0.47, MeOH) |
| 62 | | non-crystalline solid | 2224, 1789, 1665, 1574 film | DMSO-d$_6$ 3.21(3H, s), 3.29(3H, s), 3.53–3.67(4H, m), 4.05–4.21(3H, m), 4.52–4.80(3H, m), 5.65(1H, d, J=4.2Hz), 6.81(1H, d, J=7.4Hz), 6.93–6.97(2H, m), 7.04(1H, d, J=7.1Hz), 7.56–7.58(2H, m). | 418 (M$^+$) | −89.5° (c = 0.41, MeOH) |

TABLE 32

| Ex. No. | Structural formula | m.p. (rec. from soln.) | IR cm⁻¹ | ¹H NMR (δ) ppm | MS | [α]$_D$ |
|---|---|---|---|---|---|---|
| 63 | | non-crystalline solid | 2225, 1673, 1593 film | DMSO-d$_6$<br>3.20(3H, s),<br>3.29(3H, s),<br>3.53–3.65(4H, m),<br>4.11–4.15(1H, m),<br>4.55–4.70(2H, m),<br>4.81(1H, t, J=6.2Hz),<br>5.64(1H, d, J=4.1Hz),<br>6.89(1H, d, J=7.3Hz),<br>6.96(1H, d, J=6.8Hz),<br>7.03(1H, d, J=5.7Hz),<br>7.11(1H, d, J=7.3Hz),<br>7.56–7.58(2H, m). | 454 (M⁺) | −86.4° (c = 0.14, MeOH) |
| 64 | | 180.0~182.0° C. (Et$_2$O) | 3315, 2933, 1661, 1574, 1504 film | DMSO-d$_6$<br>0.78(3H, t, J=7.5Hz),<br>1.59(2H, dd, J=6.0Hz, 9.0Hz),<br>3.21(3H, s), 3.27(3H, s),<br>3.50–3.64(4H, m),<br>3.75(2H, t, J=6.0Hz),<br>4.13–4.18(1H, m),<br>4.67(1H, t, J=7.5Hz),<br>5.46(1H, d, J=6.0Hz),<br>6.73–6.82(3H, m ),<br>6.92–7.00(3H, m). | 408 (M⁺) | |

TABLE 33

| Ex. No. | Structural formula | m.p. (rec. from soln.) | IR cm⁻¹ | ¹H NMR (δ) ppm | MS | [α]$_D$ |
|---|---|---|---|---|---|---|
| 65 | | 145.5~146.5° C. (Et$_2$O) | 3315, 2921, 1661, 1573, 1488 film | CDCl$_3$<br>1.61–1.77(3H, m),<br>3.36(3H, s),<br>3.47(3H, s),<br>3.69–3.83(4H, m),<br>3.91–3.99(1H, m),<br>4.13–4.19(1H, m),<br>4.45–4.65(3H, m),<br>4.97(1H, t, J=7.5Hz),<br>5.56–5.75(2H, m),<br>6.78–6.91(4H, m),<br>7.03–7.07(1H, m). | 419 (M⁺) | |
| 66 | | non-crystalline solid | 3312, 2926, 1663, 1577, 1509, 1489 film | DMSO-d$_6$<br>3.21(3H, s), 3.28(3H, s),<br>3.51–3.63(4H, m),<br>4.12(1H, dd, J=4.1Hz, 6.4Hz),<br>4.34–4.49(2H, m),<br>4.70(1H, t, J=9.0Hz),<br>5.05–5.12(2H, m),<br>5.43(1H, d, J=4.1Hz),<br>5.83–5.90(1H, m),<br>6.76–6.83(3H, m),<br>6.93–6.97(2H, m),<br>7.02(1H, d, J=7.3Hz). | 405 (M⁺) | |

TABLE 34

| Ex. No. | Structural formula | m.p. (rec. from soln.) | IR cm$^{-1}$ | $^1$H NMR (δ) ppm | MS | [α]$_D$ |
|---|---|---|---|---|---|---|
| 67 | | non-crystalline solid | 3314, 2931, 2224, 1667, 1608, 1567, 1558 film | DMSO-d$_6$ 1.19(3H, t, J=5.2Hz), 3.24(3H, s), 3.27(3H, s), 3.53–3.69(4H, m), 3.79–3.81(2H, m), 3.98(1H, d, J=5.6Hz), 4.21(1H, d, J=5.6Hz), 5.26(1H, br s), 5.64(1H, br s), 6.33(1H, d, J=7.2Hz), 6.92(1H, d, J=2.1Hz), 6.97(1H, d, J=6.6Hz), 7.20(1H, dd, J=7.2Hz, 2.1Hz), 7.59–7.69(2H, m). | 399 (M$^+$) | |
| 68 | | non-crystalline solid | 3384, 2927, 2224, 1664, 1578 KBr | DMSO-d$_6$ 2.95(3H, s), 3.22(3H, s), 3.41(2H, t, J=7.0Hz), 3.53–3.69(4H, m), 4.16–4.23(2H, m), 4.82(1H, t, J=8.0Hz), 5.65(1H, d, J=6.0Hz), 6.81(1H, d, J=10.0Hz), 6.96(2H, d, J=8.0Hz), 7.04(1H, d, J=10.0Hz), 7.56–7.59(2H, m). | 478 (M$^+$) | −42.2° (c = 1.09, MeOH) |

TABLE 35

| Ex. No. | Structural formula | m.p. (rec. from soln.) | IR cm$^{-1}$ | $^1$H NMR (δ) ppm | MS | [α]$_D$ |
|---|---|---|---|---|---|---|
| 69 | | non-crystalline solid | 3299, 2924, 2223, 1664, 1578 KBr | DMSO-d$_6$ 2.52(3H, s), 2.93–3.07(2H, m), 3.23(3H, s), 3.29(3H, s), 3.52–3.69(4H, m), 4.13–4.22(2H, m), 4.77(1H, m), 5.63–5.67(1H, m), 6.81(1H, d, J=10.0Hz), 6.94–6.98(2H, m), 7.04(1H, d, J=10.0Hz), 7.56–7.63(2H, m). | 462 (M$^+$) | +25.9° (c = 0.94, MeOH) |
| 70 | | non-crystalline solid | 2224, 1666, 1580 film | DMSO-d$_6$ 2.72–2.88(2H, m), 3.21(3H, s), 3.27(3H, s), 3.52–3.66(4H, m), 3.97–4.20(3H, m), 4.79(1H, t, J=6.0Hz), 5.67(1H, d, J=6.0Hz), 6.82(1H, d, H=9.0Hz), 6.94–7.05(3H, m), 7.56–7.58(2H, m). | 425 (M$^+$) | −80.9° (c = 0.81, MeOH) |

TABLE 36

| Ex. No. | Structural formula | m.p. (rec. from soln.) | IR cm⁻¹ | ¹H NMR (δ) ppm | MS | [α]$_D$ |
|---|---|---|---|---|---|---|
| 71 | | non-crystalline solid | 3316, 2927, 2224, 1737, 1663, 1574 KBr | DMSO-d$_6$<br>2.47–2.64(2H, m),<br>3.21(3H, s), 3.28(3H, s),<br>3.47(3H, s), 3.53–3.66(4H, m),<br>3.98–4.14(3H, m),<br>4.77(1H, t, J=9.0Hz),<br>5.65(1H, d, J=6.0Hz),<br>6.78(1H, d, J=9.0Hz),<br>6.88(1H, d, J=6.0Hz),<br>6.95(1H, d, J=6.0Hz),<br>7.00(1H, d, J=9.0Hz),<br>7.52(1H, br s), 7.57(1H, m). | 458 (M⁺) | −105.8° (c = 0.98, MeOH) |
| 72 | | 117.5–119.5° C. (Et$_2$O) | 3301, 1658, 1580, 1511, 1488 film | DMSO-d$_6$<br>2.82–2.85(2H, m),<br>3.23(3H, s),<br>3.27(3H, s),<br>3.51–3.65(4H, m),<br>3.97–4.16(3H, m),<br>4.73(1H, t, J=7.8Hz),<br>5.44(1H, d, J=5.5Hz),<br>6.78–6.83(2H, m),<br>6.94–6.98(3H, m),<br>7.04(1H, d, J=9.8Hz). | 418 (M⁺) | |

TABLE 37

| Ex. No. | Structural formula | m.p. (rec. from soln.) | IR cm⁻¹ | ¹H NMR (δ) ppm | MS | [α]$_D$ |
|---|---|---|---|---|---|---|
| 73 | | 155.0–156.0° C. (Et$_2$O—AcOEt) | 3300, 2927, 1738, 1664, 1577 film | DMSO-d$_6$<br>2.62–2.67(2H, m),<br>3.24(3H, s), 3.29(3H, s),<br>3.51(3H, s),<br>3.52–3.66(4H, m),<br>3.97–4.14(3H, m(,<br>4.72(1H, t, J=8.1Hz),<br>5.44(1H, d, J=5.5Hz),<br>6.76–6.84(3H, m),<br>6.89–7.01(3H, m ). | 451 (M⁺) | |
| 74 | | non-crystalline solid | 2224, 1672, 1574 film | DMSO-d$_6$<br>2.92(2H, t, J=6.0Hz),<br>3.23(3H, s), 3.26(3H, s),<br>3.51–3.68(4H, m),<br>3.94–4.18(4H, m),<br>5.33(1H, br s),<br>5.63(1H, br s),<br>6.38(1H, d, J=9.0Hz),<br>6.96(1H, d, J=9.0Hz),<br>7.00(1H, d, J=3.0Hz),<br>7.25(1H, dd, J=9.0Hz, 3.0Hz ),<br>7.57–7.64(2H, m). | 424 (M⁺) | |

TABLE 38

| Ex. No. | Structural formula | m.p. (rec. from soln.) | IR cm⁻¹ | ¹H NMR (δ) ppm | MS | [α]$_D$ |
|---|---|---|---|---|---|---|
| 75 | (structure) | non-crystalline solid | 2224, 1738, 1667, 1574 film | DMSO-d$_6$ 2.70(2H, t, J=6.0Hz), 3.23(3H, s), 3.25(3H, s), 3.51–3.69(7H, m), 3.94–4.05(3H, m), 4.16(1H, br s), 5.28(1H, br s), 5.63(1H, br s), 6.33(1H, d, J=9.0Hz), 6.93–6.97(2H, m), 7.21(1H, dd, J=9.0Hz, 3.0Hz), 7.58–7.65(2H, m). | 457 (M⁺) | |
| 76 | (structure) | non-crystalline solid | 3375, 2927, 2224, 1664, 1578, 1560 KBr | DMSO-d$_6$ 3.22(3H, s), 3.28(3H, s), 3.60(4H, q, J=9.0Hz), 4.07(1H, dd, J=9.0Hz, 6.0Hz), 4.37–4.47(2H, m), 4.70–4.84(3H, m), 5.62(1H, d, J=9.0Hz), 6.81(1H, d, J=9.0Hz), 6.95(2H, d, J=9.0Hz), 7.02(1H, d, J=9.0Hz), 7.47(1H, br s), 7.57(1H, m). | 445 (M⁺) | −115.3° (c = 1.08, MeOH) |

TABLE 39

| Ex. No. | Structural formula | m.p. (rec. from soln.) | IR cm⁻¹ | ¹H NMR (δ) ppm | MS | [α]$_D$ |
|---|---|---|---|---|---|---|
| 77 | (structure) | non-crystalline solid | 2224, 1665, 1577 film | CDCl$_3$ 1.06(6H, t, J=6.0Hz), 2.60(4H, q, J=6.0Hz), 3.37(3H, s), 3.43(3H, s), 3.68–3.82(4H, m), 4.22(1H, d, J=9.0Hz), 4.59–4.94(3H, m), 5.10(1H, t, J=6.0Hz), 6.83–6.98(3H, m), 7.44–7.47(1H, m), 7.66(1H, br s). | 495 (M⁺) | −113.11° (c = 0.768, MeOH) |
| 78 | (structure) | 138~142° C. (−) | 3354, 2930, 2226, 1728, 1666, 1574, 1556 film | DMSO-d$_6$ 3.21(3H, s), 3.27(3H, s), 3.51–3.65(4H, m), 4.04–4.10(1H, m), 4.38–4.60(2H, m), 4.78(1H, t, J=9.0Hz), 5.67(1H, d, J=6.0Hz), 6.83(1H, d, J=9.0Hz), 6.88(1H, d, J=6.0Hz), 6.96(1H, d, J=9.0Hz), 7.06(1H, d, J=9.0Hz), 7.56–7.58(2H, m). | 430 (M⁺) | −115° (c = 0.44, MeOH) |

TABLE 40

| Ex. No. | Structural formula | m.p. (rec. from soln.) | IR cm⁻¹ | ¹H NMR (δ) ppm | MS | [α]_D |
|---|---|---|---|---|---|---|
| 79 | (structure: 4-fluorophenyl-NH, chromane with CN, OH, CH₂OMe, CH₂OMe) | non-crystalline solid | 2224 KBr | CDCl₃ 3.35(3H, s), 3.41(3H, s), 3.46(1H, s), 3.60–3.90(4H, m), 3.90–4.30(1H, br s), 4.12(1H, dd, J=3.0Hz, 9.0Hz), 4.57(1H, d, J=9.0Hz), 6.60–6.70(2H, m), 6.85–7.00(3H, m), 7.42(1H, d, J=8.4Hz), 7.64(1H, s). | 372 (M⁺) | −49.8° (c = 0.78, MeOH) |
| 80 | (structure: 4-fluoro-3-methylphenyl-NH, chromane with CN, OH, CH₂OMe, CH₂OMe) | non-crystalline solid | 2224 KBr | CDCl₃ 2.23(3H, s), 3.33(1H, d, J=4.5Hz), 3.37(3H, s), 3.43(3H, s), 3.60–3.85(5H, m), 4.10(1H, dd, J=4.5Hz, 9.2Hz), 4.57(1H, d, J=9.2Hz), 6.40–6.60(1H, m), 6.80–6.90(1H, m), 6.96(1H, d, J=8.5Hz), 7.45(1H, d, J=8.5Hz), 7.66(1H, s). | 386 (M⁺) | −51.1° (c = 0.99, MeOH) |

TABLE 41

| Ex. No. | Structural formula | m.p. (rec. from soln.) | IR cm⁻¹ | ¹H NMR (δ) ppm | MS | [α]_D |
|---|---|---|---|---|---|---|
| 81 | (structure: pyridine-N-oxide-NH, chromane with CN, OH, CH₂OMe, CH₂OMe) | non-crystalline solid | 2223 KBr | CDCl₃ 3.32(3H, s), 3.36(3H, s), 3.63(1H, d, J=4.0Hz), 3.65(1H, d, J=4.0Hz), 3.71(1H, d, J=7.9Hz), 3.92(1H, d, J=7.9Hz), 4.22(1H, d, J=6.9Hz), 4.95–5.05(1H, m), 6.50–6.60 (1H, m), 6.86(1H, d, J=6.3Hz), 6.97(1H, d, J=6.3Hz), 7.15–7.45(3H, m), 7.55(1H, s), 7.99(1H, d, J=4.6Hz). | 371 (M⁺) | +71.1° (c = 0.81, MeOH) |
| 82 | (structure: pyridine-N-oxide-NH, chromane with CN, OH, CH₂OMe, CH₂OMe) | non-crystalline solid | 2223 KBr | DMSO-d₆ 3.23(3H, s), 3.26(3H, s), 3.50–3.65(3H, m), 3.73(1H, d, J=10.6Hz), 3.95–4.02(1H, m), 4.50–4.60(1H, m), 5.86(1H, d, J=5.5Hz), 6.61(1H, d, J=8.5Hz), 6.71(1H, d, J=8.5Hz), 6.98(1H, d, J=8.8Hz), 7.05–7.15(1H, m), 7.49(1H, d, J=6.0Hz), 7.55–7.70(2H, m), 7.76(1H, s). | 371 (M⁺) | +21.1° (c = 0.61, MeOH) |

TABLE 42

| Ex. No. | Structural formula | m.p. (rec. from soln.) | IR cm⁻¹ | ¹H NMR (δ) ppm | MS | [α]_D |
|---|---|---|---|---|---|---|
| 83 | | 147.0~149.2° C. (AcOEt-n-Hexane) | 2226, 1655, 1624, 1600, 1490 KBr | CDCl₃ 3.40(3H, s), 3.48(3H, s), 3.40–3.60(1H, m), 3.70–3.95(4H, m), 4.30–4.42(1H, m), 6.58(1H, d, J=6.0Hz), 6.65–6.80(2H, m), 7.04(1H, d, J=6.0Hz), 7.40–7.75(4H, m), 8.49(1H, d, J=6.0Hz). | 406 (M⁺) | −74.7° (c = 0.95, CHCl₃) |
| 84 | | 133.9~135.0° C. (EtOH) | 2224, 1631, 1591, 1577 KBr | CDCl₃ 3.30(3H, s), 3.47(3H, s), 3.75(1H, d, J=9.0Hz), 3.78(2H, s), 3.96(1H, d, J=9.0Hz), 4.45(1H, d, J=9.0Hz), 6.06(1H, d, J=9.0Hz), 6.33(1H, s), 7.02(1H, d, J=9.0Hz), 7.34(1H, s), 7.40–8.00(6H, m), 8.95(1H, s). | 406 (M⁺) | +23.9° (c = 1.04, CHCl₃) |

TABLE 43

| Ex. No. | Structural formula | m.p. (rec. from soln.) | IR cm⁻¹ | ¹H NMR (δ) ppm | MS | [α]_D |
|---|---|---|---|---|---|---|
| 85 | | non-crystalline solid | 2225, 1641, 1585, 1490 KBr | CDCl₃ 3.37(3H, s), 3.41(3H, s) 3.70–4.00(4H, m), 3.78(3H, s), 4.42(1H, s), 4.50–4.60(1H, m), 6.21(1H, d, J=6.0Hz), 7.04(1H, d, J=9.0Hz), 7.53(1H, d, J=9.0Hz), 7.66(1H, s), 7.75–7.85(2H, m), 7.90–7.95(1H, m). 8.40–8.45(1H, m). | 437 (M⁺) | −57.2° (c = 1.01, MeOH) |
| 86 | | non-crystalline solid | 2225, 1647, 1588 KBr | CDCl₃ 2.12(3H, s), 2.20(3H, s), 3.39(3H, s), 3.41(3H, s), 3.65–3.95(7H, m), 4.22–4.24(1H, m), 4.40–4.44(1H, m), 6.02(1H, d, J=9.0Hz), 7.01(1H, d, J=9.0Hz), 7.50(1H, d, J=9.0Hz), 7.59(1H, s). | 415 (M⁺) | −104.6° (c = 0.98, MeOH) |

TABLE 44

| Ex. No. | Structural formula | m.p. (rec. from soln.) | IR cm⁻¹ | ¹H NMR (δ) ppm | MS | [α]$_D$ |
|---|---|---|---|---|---|---|
| 87 | | non-crystalline solid | 1654, 1578 KBr | CDCl$_3$ 3.35(3H, s), 3.42(3H, s), 3.60–4.00(5H, m), 3.77(3H, s), 4.35–4.45(1H, m), 5.89(1H, d, J=6.0Hz), 6.83(1H, d, J=9.0Hz), 6.97(2H, s), 7.30–7.35(2H, m). | 440 (M⁺) 442 (M⁺) | −71.2° (c = 0.59, MeOH) |
| 88 | | non-crystalline solid | 1662, 1585, 1436 KBr | CDCl$_3$ 3.37(3H, s), 3.41(3H, s), 3.6–4.1(5H, m), 3.72(3H, s), 4.45–4.55(1H, m), 5.99(1H, d, J=6.0Hz), 7.00(2H, s), 7.03(1H, d, J=9.0Hz), 8.14(1H, d, J=9.0Hz), 8.25(1H, s). | 407 (M⁺) | −102.3° (c = 1.0, CHCl$_3$) |

FORMULATION EXAMPLE 1: TABLET

| | |
|---|---|
| Compound of Example 28 | 1 g |
| Lactose | 3 kg |
| Hydroxypropyl cellulose | 200 g |
| Starch | 1 kg |
| Talc | 10 g |
| Magnesium stearate | 10 g |

The above ingredients were compressed by a conventional method to give tablets containing 0.1 mg of an active substance per tablet.

FORMULATION EXAMPLE 2: CAPSULE

| | |
|---|---|
| Compound of Example 28 | 1 g |
| Lactose | 2 kg |
| Magnesium stearate | 10 g |

The above ingredients were filled in hard gelatin capsules by a conventional method to give capsules containing 0.1 mg of an active substance per capsule.

What is claimed is:

1. A chroman compound of the formula [I]

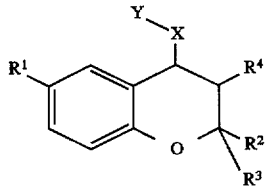

[I]

wherein

R$^1$ is a cyano, a nitro, a trihalomethyl, a trihalomethoxy or a halogen atom;

R$^2$ is a lower alkoxyalkyl wherein the total carbon number of the alkoxy moiety and alkyl moiety is 2 to 6, a phenyloxy C$_1$–C$_5$ alkyl or a dialkoxyalkyl having 3 to 8 carbon atoms;

R$^3$ is a lower alkoxyalkyl wherein the total carbon number of the alkoxy moiety and alkyl moiety is 2 to 6 or a phenyloxy C$_1$–C$_5$ alkyl;

R$^4$ is a hydroxy, a formyloxy or a lower alkanoyloxy;

X is N—H, an oxygen atom or a sulfur atom; and

Y is a dihydrooxopyridazinyl or dihydrothioxopyridazinyl optionally substituted by 1 to 3 substituents selected from the group consisting of lower alkyl having 1 to 7 carbon atoms optionally monosubstituted by a substituent selected from the group consisting of nitro, halogen atom, cyano, lower alkoxy having 1 to 4 carbon atoms, cycloalkyl having 3 to 6 carbon atoms, lower alkylsulfonyl having 1 to 4 carbon atoms, lower alkylsulfinyl having 1 to 4 carbon atoms, carboxyl, di-lower alkylamino having 1 to 6 carbon atoms, alkylthio having 1 to 4 carbon atoms, benzyloxycarbonyl and lower alkoxycarboxyl having 2 to 5 carbon atoms:

lower alkenyl having 2 to 4 carbon atoms:

phenyl optionally mono-substituted by nitro and benzyl, or a pharmaceutically acceptable salt thereof.

2. The chroman compound of claim 1, wherein R$^1$ is a cyano, a nitro or a halogen atom, R$^2$ is a lower alkoxyalkyl wherein the total carbon number of the alkoxy moiety and alkyl moiety is 2 to 6, R$^3$ is a lower alkoxyalkyl wherein the total carbon number of the alkoxy moiety and alkyl moiety is 2 to 6, R$^4$ is a hydroxy and X is N—H or an oxygen atom, or a pharmaceutically acceptable salt thereof.

3. The chroman compound of claim 2, wherein X is N—H, R$^1$ is a cyano, R$^2$ is a methoxymethyl and R$^3$ is a methoxymethyl, or a pharmaceutically acceptable salt thereof.

4. The chroman compound of claim 3, wherein X is N—H and Y is 1,6-dihydro-1-$C_1$–$C_5$ alkyl-6-oxo-3-pyridazinyl or 1,6-dihydro-1-substituted $C_1$–$C_5$ alkyl-6-oxo-3-pyridazinyl, or a pharmaceutically acceptable salt thereof.

5. The chroman compound of claim 1, which is a member selected from the group consisting of (−)-(3S,4R)-6-cyano-3,4-dihydro-4-[(1,6-dihydro-1-methyl-6-oxo-3-pyridazinyl)amino]-2,2-bis(methoxymethyl)-2H-1-benzopyran-3-ol, (−)-(3S,4R)-6-cyano-4-[(1-ethyl-1,6-dihydro-6-oxo-3-pyridazinyl)amino]-3,4-dihydro-2,2-bis(methoxymethyl)-2H-1-benzopyran-3-ol, (−)-(3S,4R)-6-cyano-3,4-dihydro-4-[(1,6-dihydro-1-isopropyl-6-oxo-3-pyridazinyl)amino]-2,2-bis(methoxymethyl)-2H-1-benzopyran-3-ol, (−)-(3S,4R)-6-cyano-3,4-dihydro-4-[(1,6-dihydro-1-methyl-6-oxo-3-pyridazinyl)amino]-2,2-bis(methoxymethyl)-2H-1-benzopyran-3-ol hydrate and (−)-(3S,4R)-6-cyano-4-[(1-cyclopropylmethyl-1,6-dihydro-6-oxo-3-pyridazinyl)amino]-3,4-dihydro-2,2-bis(methoxymethyl)-2H-1-benzopyran-3-ol, or a pharmaceutically acceptable salt thereof.

6. A pharmaceutical composition comprising the chroman compound of claim 1 or a pharmaceutically acceptable salt thereof and a pharmaceutically acceptable carrier.

7. A pharmaceutical composition comprising the chroman compound of claim 5 or a pharmaceutically acceptable salt thereof and a pharmaceutically acceptable carrier.

8. A method of preventing or treating cardiovascular disorders which comprises administering to a patient in need of treatment an effective amount of a compound of claim 1, or a pharmaceutically acceptable salt thereof.

9. A method of preventing or treating cardiovascular disorders which comprises administering to a patient in need of treatment an effective amount of a compound of claim 5, or a pharmaceutically acceptable salt thereof.

* * * * *